(12) United States Patent
Marc

(10) Patent No.: US 9,901,742 B2
(45) Date of Patent: *Feb. 27, 2018

(54) APPARATUS AND METHOD FOR HEATING A TREATMENT REGION WITH AN ALTERNATING ELECTRIC FIELD

(75) Inventor: Michel Marc, Lenexa, KS (US)

(73) Assignee: INNOVOLINK, LLC, Lenexa, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/103,638

(22) Filed: May 9, 2011

(65) Prior Publication Data

US 2012/0290048 A1 Nov. 15, 2012

(51) Int. Cl.
*A61N 1/40* (2006.01)

(52) U.S. Cl.
CPC .............. *A61N 1/403* (2013.01); *A61N 1/406* (2013.01)

(58) Field of Classification Search
USPC ............... 607/98–102, 148, 152; 606/32–52; 219/764–780
See application file for complete search history.

(56) References Cited

U.S. PATENT DOCUMENTS

| | | | |
|---|---|---|---|
| 3,118,040 A * | 1/1964 | Stanley | 219/778 |
| 4,140,130 A | 2/1979 | Storm, III | |
| 4,237,898 A | 12/1980 | Whalley | |
| 4,282,887 A * | 8/1981 | Sterzer | 607/101 |
| 4,303,636 A | 12/1981 | Gordon | |
| 4,462,412 A | 7/1984 | Turner | |
| 4,589,423 A | 5/1986 | Turner | |
| 4,846,196 A | 7/1989 | Wiksell | |
| 4,934,365 A | 6/1990 | Morgenthaler | |
| 5,010,897 A | 4/1991 | Leveen | |
| 5,224,492 A | 7/1993 | Takahashi et al. | |
| 5,295,955 A | 3/1994 | Rosen et al. | |
| 5,441,746 A | 8/1995 | Chagnon | |
| 5,582,609 A | 12/1996 | Swanson et al. | |
| 5,704,355 A | 1/1998 | Bridges | |

(Continued)

OTHER PUBLICATIONS

Harrison et al., A comparison of Deep-Heating Electrode Concepts fo Hyperthermia, 1985, J. Microwave Power, vol. 20, pp. 1-8.*

(Continued)

*Primary Examiner* — Joseph Stoklosa
*Assistant Examiner* — Adam Avigan
(74) *Attorney, Agent, or Firm* — Stinson Leonard Street LLP

(57) ABSTRACT

An apparatus and method for heating a treatment region of a subject via the application of an alternating electric field is disclosed. The method includes positioning a treatment region of a subject between a first electrode and a second electrode sized to extend across the treatment region. The first and second electrodes are connected to a generator operable to apply an alternating electric field between the electrodes at a frequency in the range of 1 MHz to 100 MHz. The method also includes activating the generator to apply the alternating electric field between the first and second electrodes and across the treatment region. The alternating electric field causes movement of polar molecules in the treatment region whereby friction resulting from this molecular movement translates into heat throughout the treatment region.

17 Claims, 8 Drawing Sheets

(56) References Cited

U.S. PATENT DOCUMENTS

| | | | |
|---|---|---|---|
| 6,190,657 | B1 | 2/2001 | Pawelek et al. |
| 6,208,903 | B1 | 3/2001 | Richards et al. |
| 6,480,746 | B1* | 11/2002 | Ingle ................. A61B 18/1485 128/898 |
| 7,113,832 | B2* | 9/2006 | Longo ........................... 607/101 |
| 7,133,725 | B2 | 11/2006 | Stirbl et al. |
| 7,329,638 | B2 | 2/2008 | Yang et al. |
| 7,510,555 | B2* | 3/2009 | Kanzius ........................ 606/33 |
| 7,630,774 | B2* | 12/2009 | Karni et al. ................. 607/101 |
| 7,668,603 | B2 | 2/2010 | Stirbl et al. |
| 7,754,230 | B2 | 7/2010 | Kolodney et al. |
| 7,805,201 | B2* | 9/2010 | Palti ............................... 607/76 |
| 2002/0193832 | A1 | 12/2002 | Gray |
| 2003/0032995 | A1 | 2/2003 | Handy et al. |
| 2005/0251233 | A1 | 11/2005 | Kanzius |
| 2005/0251234 | A1 | 11/2005 | Kanzius et al. |
| 2005/0273143 | A1 | 12/2005 | Kanzius et al. |
| 2006/0012082 | A1 | 1/2006 | Marc |
| 2006/0012083 | A1 | 1/2006 | Marc |
| 2006/0019146 | A1 | 1/2006 | Yoshitake et al. |
| 2006/0036300 | A1 | 2/2006 | Kreindel |
| 2006/0190063 | A1 | 8/2006 | Kanzius |
| 2007/0248537 | A1 | 10/2007 | Yang et al. |
| 2007/0250139 | A1 | 10/2007 | Kanzius |
| 2008/0228063 | A1 | 9/2008 | Turner et al. |
| 2008/0269851 | A1 | 10/2008 | Deem et al. |
| 2010/0168727 | A1 | 7/2010 | Hancock et al. |
| 2011/0106226 | A1 | 5/2011 | Szasz et al. |
| 2011/0269855 | A1 | 11/2011 | Marc |

OTHER PUBLICATIONS

Gannon et al., *Carbon Nanotube-enhanced Thermal Destruction of Cancer Cells in a Noninvasive Radiofrequency Field*, Amer Cancer Soc 2654-2665 (2007).

Curley et al., *Noninvasive radiofrequency field-induced hyperthermic cytotoxicity in human cancer cells using cetuximab-targeted gold nanoparticles*, Jour of Experimental Therapeutics and Oncology 7 313-326 (2008).

Gannon et al., *Intracellular gold nanoparticles enhance noninvasive radiofrequency thermal destruction of human gastrointestinal cancer cells*, Jour of Nanobiotechnology 6:2 (2008).

Moran et al., *Size-Dependent Joule Heating of Gold Nanoparticles Using Capacityively Coupled Radiofrequency Fields*, Nano Res 2 400-405 (2009).

Glazer et al.., *Radiofrequency Field-Induced Thermal Cytotoxicity in Cancer Cells Treated With Fluorescent Nanoparticles*, Cancer 3285-3293 (Jul. 2010).

Li et al., *A novel functional CT contrast agent for molecular imaging of cancer*, Phys Med Biol 55 4389-4397(2010).

International Search Report and Written Opinion dated Aug. 17, 2012 for corresponding PCT application, PCT/US2012/036934, international filing date, May 8, 2012.

U.S. Appl. No. 13/103,668, filed May 9, 2011, Marc.
U.S. Appl. No. 13/103,692, filed May 9, 2011, Marc.
U.S. Appl. No. 13/103,715, filed May 9, 2011, Marc.
U.S. Appl. No. 13/103,739, filed May 9, 2011, Marc.

Kuphaldt, Tony R. "Section 14.7: Impedance Transformation" Lessons in Electric Circuits: vol. II—AC. 2007. All About Circuits. Web. Apr. 11, 2013, pp. 523-529, http://www.allaboutcircuits.com.

Harrison et al., "A Comparison of Deep-Heating Electrode Concepts for Hyperthermia." Journal of microwave power and electromagnetic energy. 20.1 (1985): 1-8. Web. Dec. 9, 2013. http://www.jmpee.org/JMPEE_PDFs/20-1_bl/JMPEE-Vol20-Pg1-Harrison.pdf.

Tomimatsu et al. "Refinement of Circulating Liquid of Overlay Bolus in Hyperthermia Using an 8MHz RF Capacitive Heating Device" Thermal Medicine (Japanese Journal of Hyperthermic Oncology). 15.2 (1999): 71-77. Web. Dec. 27, 2013. <https://www.jstage.jst.go.jp/article/thermalmedicine 1985/15/2/15_2_71/_pdf>.

* cited by examiner

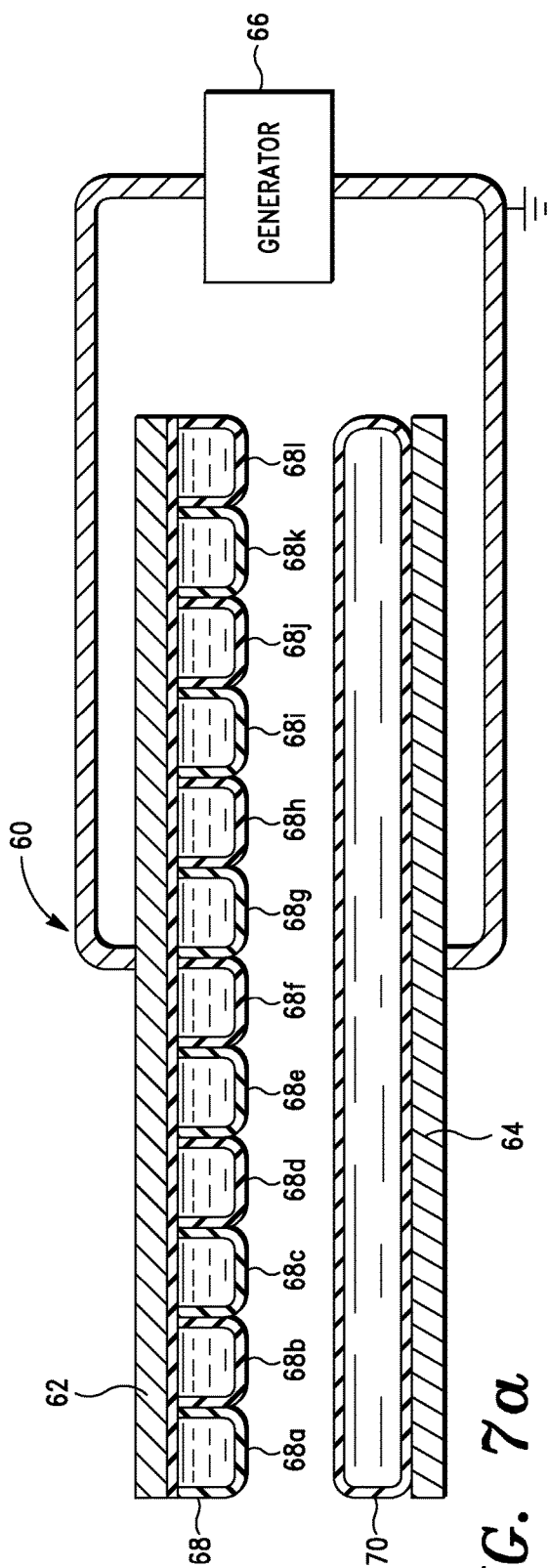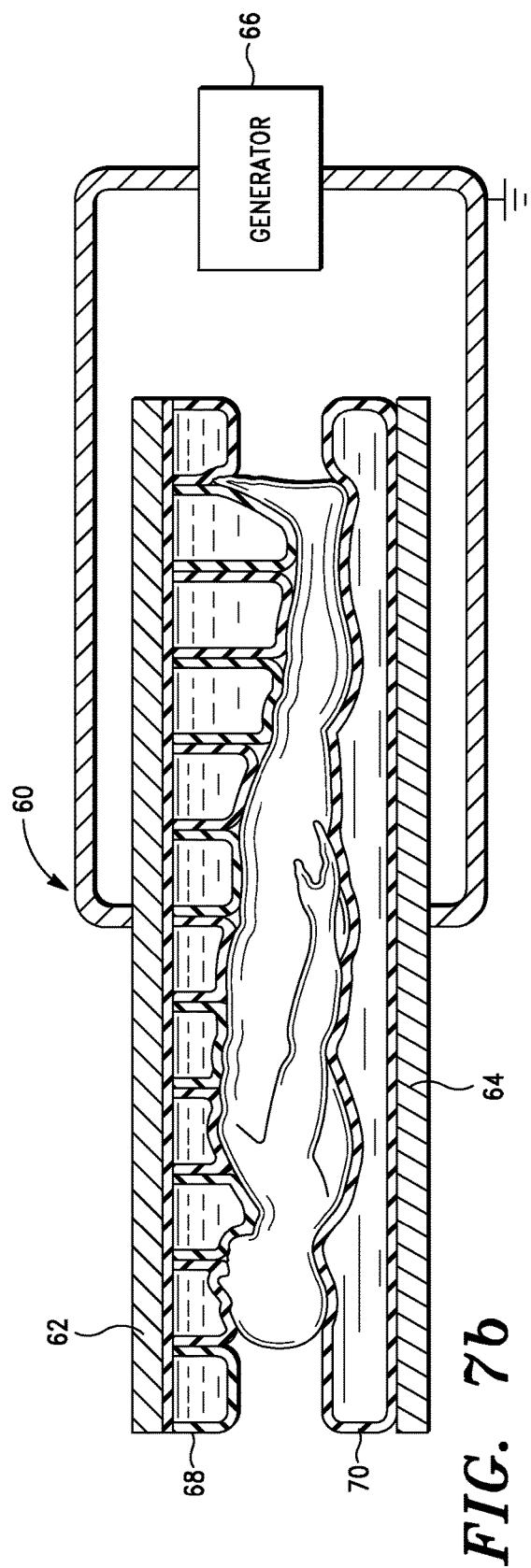
FIG. 7a
FIG. 7b

APPARATUS AND METHOD FOR HEATING A TREATMENT REGION WITH AN ALTERNATING ELECTRIC FIELD

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Various devices have been used in the past to heat a treatment region of an animal body for therapeutic purposes. In particular, it is known in the art to use a radio frequency (RF) or microwave electromagnetic field to induce hyperthermia in an animal body for the purpose of transforming or killing certain cells of the animal body. For example, focused microwave thermotherapy has been used for breast cancer treatment, in which a woman's breast is placed between two compression plates and a microwave unit positioned on each side of the breast applies an electromagnetic field across the breast. The amplitude of the electromagnetic field decreases as it penetrates further into the breast and, as such, the electromagnetic field is not constant throughout the thickness of the breast. Devices that utilize an electromagnetic field—whether operating at RF or microwave frequencies—do not evenly heat the entire thickness of a treatment region and, as a result, have not been able to achieve the desired therapeutic outcomes.

BRIEF SUMMARY OF THE INVENTION

The present invention is directed to an apparatus and method for heating a treatment region of a subject via the application of an alternating electric field that provides substantially even heating throughout the thickness of the treatment region. The method includes positioning the treatment region, which comprises all or a portion of the subject, between a first electrode and a second electrode sized to extend across the treatment region. The first and second electrodes are connected to a generator operable to apply an alternating electric field between the electrodes at a frequency in the range of 1 MHz to 100 MHz, and preferably at 27.12 MHz or 40.68 MHz. The method also includes activating the generator to apply the alternating electric field between the first and second electrodes and across the treatment region. The alternating electric field causes movement of polar molecules in the treatment region whereby friction resulting from this molecular movement translates into heat throughout the thickness of the treatment region such that the same cell type in different sub-regions of the treatment region heats at substantially the same rate.

BRIEF DESCRIPTION OF THE DRAWINGS

FIG. 7a is a diagram of an exemplary apparatus for generating an alternating electric field between a top electrode and a bottom electrode, wherein a compartmentalized top bladder and a continuous bottom bladder are attached to the top and bottom electrodes, respectively.

FIG. 7b is a diagram of the apparatus of FIG. 7a, wherein the top bladder compartments and the bottom bladder are filled with various flowable materials such that the bladders conform to the contours of the subject and allow a substantially constant current to be obtained across the treatment region of the subject.

DETAILED DESCRIPTION OF EXEMPLARY EMBODIMENTS

Figure 1:
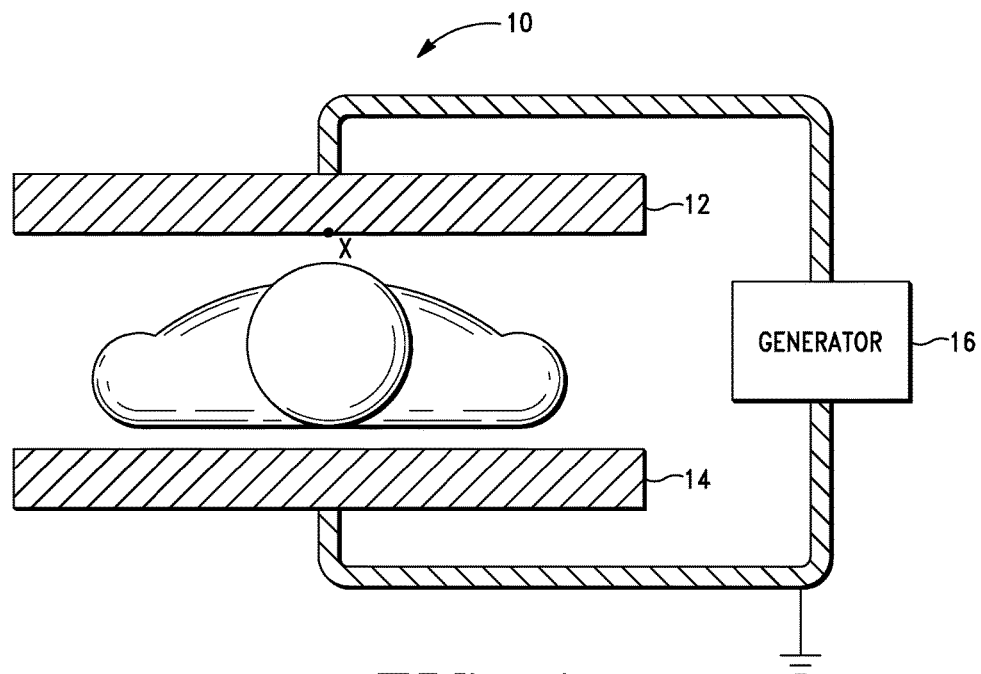
FIG. 1 is a diagram of an exemplary apparatus for generating an alternating electric field between a single-plate top electrode and a single-plate bottom electrode, wherein the voltage between the top and bottom electrodes is substantially constant.

The present invention is directed to an apparatus and method for heating biological targets of a subject through the use of dielectric heating. As used herein, the term "biological target" refers to any prokaryotic or eukaryotic cell, unicellular or multicellular microorganism, parasite, or pathogen found in a subject, including, but not limited to, bacteria, viruses, fungus, or protozoa. As used herein, the term "subject" or "body" refers to an animal such as a vertebrate, preferably a mammal (including, but not limited to, humans, murines, simians, bovines, cervids, equines, porcines, canines, and felines), and more preferably a human. As used herein, the term "dielectric heating" refers to heating via the application of an alternating electric field (referred to herein as a "dielectric field"), preferably in the radio frequency (RF) range. While the invention will be described in detail below with reference to various exemplary embodiments, it should be understood that the invention is not limited to the specific configuration or methodology of these embodiments. In addition, although the exemplary embodiments are described as embodying several different inventive features, one skilled in the art will appreciate that any one of these features could be implemented without the others in accordance with the invention.

In general terms, the present invention involves placing a treatment region of a subject between two electrodes such that the treatment region effectively becomes the dielectric of a capacitor. As used herein, the term "treatment region" refers to all or a portion of a subject to be treated with dielectric heating, and includes the biological targets and may also include non-targets. A dielectric field generated between the electrodes causes polar molecules in the treatment region to be attracted and repelled by the rapidly changing polarity of the dielectric field. The friction resulting from this molecular movement translates into heat throughout the thickness of the treatment region in such a manner as to heat and kill the biological targets. As used herein, the term "kill" in the context of a biological target refers to the killing, removal, or other elimination of the biological target. For example, in the context of a biological target that is a cell, the term "kill" encompasses the programmed and/or unprogrammed dying of the cell by any mechanism, such as by apoptosis, necrosis, aponecrosis, autophagic degeneration, mitophagy, pexophagy, lysis, dislodging, or disruption of cell membrane, and the like.

I. Biological Targets

In general, the biological targets of the present invention include any prokaryotic or eukaryotic cell, microorganism, parasite, or pathogen found in a subject, including, but not limited to, bacteria, viruses, fungus, or protozoa. Thus, the present invention may be used to selectively kill many different types of biological targets within a treatment region. Among other things, the present invention finds use with normal cells, cancerous cells, pre-cancerous cells, diseased cells, and virus-infected cells.

Thus, in one aspect, the biological targets are any of those cells found within the human body, including, but not limited to, the following types of cells: (1) circulatory system cells such as heart cells (myocardial cells); cells of the blood and lymph including erythropoietin-sensitive stem cells, erythrocytes, leukocytes (e.g., eosinophils, basophils, neutrophils (granular cells), lymphocytes, and monocytes (agranular cells)), thrombocytes, tissue macrophages (histiocytes), organ-specific phagocytes (e.g., Kupffer cells, alveolar macrophages, and microglia), β-lymphocytes, T-lymphocytes (e.g., cytotoxic T cells, helper T cells, and suppressor T cells), megaloblasts, monoblasts, myeloblasts, lymphoblasts, proerythroblasts, megakaryoblasts, promonocytes, promyelocytes, prolymphocytes, early normoblasts, megakaryocytes, intermediate normoblasts, metamyelocytes (e.g., juvenile metamyelocytes, segmented metamyelocytes, and polymorphonuclear granulocytes), late normoblasts, reticulocytes, and bone marrow cells; (2) muscle cells such as myofibrils, intrafusal fibers, and extrafusal fibers; (3) skeletal system cells such as osteoblasts, osteocytes, osteoclasts and their progenitor cells; (4) respiratory system cells such as capillary endothelial cells and alveolar cells; (5) urinary system cells such as nephrons, capillary endothelial cells, granular cells, tubule endothelial cells, and podocytes; (6) digestive system cells such as simple columnar epithelial cells, mucosal cells, acinar cells, parietal cells, chief cells, zymogen cells, peptic cells, enterochromaffin cells, goblet cells, Argentaffen cells, and G cells; (7) sensory cells such as auditory system cells (hair cells), olfactory system cells (olfactory receptor cells and columnar epithelial cells), equilibrium/vestibular apparatus cells (hair cells and supporting cells), visual system cells (pigment cells), epithelial cells, photoreceptor neurons (rods and cones), ganglion cells, amacrine cells, bipolar cells and horizontal cells; (8) mesenchymal cells, stromal cells, hair cells/follicles, and adipose (fat) cells; (9) cells of simple epithelial tissues (squamous epithelium, cuboidal epithelium, columnar epithelium, ciliated columnar epithelium, and pseudostratified ciliated columnar epithelium), cells of stratified epithelial tissues (stratified squamous epithelium (keratinized and non-keratinized), stratified cuboidal epithelium, and transitional epithelium), goblet cells, endothelial cells of the mesentery, endothelial cells of the small intestine, endothelial cells of the large intestine, endothelial cells of the vasculature capillaries, endothelial cells of the microvasculature, endothelial cells of the arteries, endothelial cells of the arterioles, endothelial cells of the veins, endothelial cells of the venules, and endothelial cells of the bladder; (10) cells of connective tissue such as loose connective (areolar) tissue including the dermis, dense fibrous connective tissue, elastic connective tissue, reticular connective tissue, adipose connective tissue, chondrocytes, adipose cells, periosteal cells, endosteal cells, odontoblasts, osteoblasts, osteoclasts, and osteocytes; and (11) epithelial cells such as sebocytes, hair follicles, hepatocytes, type II pneumocytes, mucin-producing goblet cells, and other epithelial cells and their progenitors contained within the skin, lung, liver, and gastrointestinal tract. In a preferred aspect, the biological targets are adipose cells.

In another aspect, the biological targets are neoplastic cells. The term "neoplastic cells" as used herein refers to cells that result from abnormal new growth. Neoplastic cells further include transformed cells, malignant cells or cancer cells, including blood cancers and a solid tumor (benign and malignant). As used herein, the term "tumor" refers to an abnormal mass or population of cells that result from excessive cell division, whether malignant or benign, and all pre-cancerous and cancerous cells and tissues. A "tumor" is further defined as two or more neoplastic cells. A "malignant tumor" is distinguished from a benign growth or tumor in that, in addition to uncontrolled cellular proliferation, it will invade surrounding tissues and may additionally metastasize. The terms "transformed cells," "malignant cells" and "cancer cells" are interchangeable and refer to cells that have undergone malignant transformation, but may also include lymphocyte cells that have undergone blast transformation. Malignant transformation is a conversion of normal cells to malignant cells. Transformed cells have a greater ability to cause tumors when injected into animals. Transformation can be recognized by changes in growth characteristics, particularly in requirements for macromolecular growth factors, and often also by changes in morphology. Transformed cells usually proliferate without requiring adhesion to a substratum and usually lack cell to cell inhibition and pile up after forming a monolayer in cell culture. In a preferred aspect, the biological targets are cancer cells in either solid tumor or non-solid form, including, but not limited to, those involving the following types of cancer: (1) cardiac including sarcoma (angiosarcoma, fibrosarcoma, rhabdomyosarcoma, liposarcoma), myxoma, rhabdomyoma, fibroma, lipoma and teratoma; (2) lung including bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; (3) gastrointestinal including esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), and other colorectal cancers; (4) genitourinary tract including kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) liver including hepatoma (hepatocellular carcinoma), cholangiocarcinoma, hepatoblastoma, angiosarcoma, hepatocellular adenoma, hemangioma; (6) bone including osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors; (7) nervous system including skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord (neurofibroma, meningioma, glioma, sarcoma); (8) gynecological including uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma)), fallopian tubes (carcinoma), breast (adenocarcinoma, lobular (small cell) carcinoma, intraductal carcinoma, medullary breast cancer, mucinous breast cancer, tubular breast cancer, papillary breast cancer, Paget's disease, and inflammatory breast cancer); (9) hematologic including, blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma): (10) skin including malignant melanoma, basal cell carcinoma, squamous cell carcinoma, Karposi's sarcoma, moles dysplastic nevi, lipoma, angioma, dermatofibroma, keloids, psoriasis; and (11) adrenal glands including neuroblastoma. Thus, the term "cancer cells" as used herein includes cells afflicted by any one of the above-identified conditions.

In another aspect, the biological targets are of a pathogenic origin. As used herein, the term "pathogen" refers to disease-causing organisms, microorganisms or agents, including, but not limited to, bacteria, viruses, or parasites. Thus, the term "biological targets" embraces bacterial cells, viruses, virally-infected cells, and parasites.

In another aspect, the biological targets are bacterium located within the subject. As used herein, the term "bacteria" or "bacterium" refers to all prokaryotic organisms, including those within all of the phyla in the Kingdom Procaryotae, and is intended to encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this definition are prokaryotic organisms that are gram negative or gram positive. Thus, bacterial infections or diseases that can be treated by the methods of the present invention include mycobacteria (e.g., *Mycobacteria tuberculosis, M. bovis, M. avium, M. leprae*, or *M. africanum*), rickettsia, mycoplasma, chlamydia, and *legionella*. Other examples of bacterial infections contemplated include, but are not limited to, infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species. Specific examples of infectious bacteria include, but are not limited to, *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pncumoniae, Haemophilus influenzae, Bacillus antracis, corynebacterium diphtheriae, Erysipelothrix rhusiopathiae, Clostridium perfringers, Clostridium tetani, Entcrobacter acrogenes, Klebsiella pneumoniae, Pasturella multocida, Fusobacterium nucleatum, Streptobacillus moniliformis, Treponema pallidium, Treponema pertenue, Leptospira, Rickettsia*, and *Actinomyces israelli*.

In another aspect, the biological targets are viruses located within the subject. As used herein, the term "virus" refers to infectious agents, which with certain exceptions, are not observable by light microscopy, lack independent metabolism, and are able to replicate only within a host cell. The individual particles (i.e., virions) consist of nucleic acid and a protein shell or coat; some virions also have a lipid containing membrane.

In another aspect, the biological targets are fungal cells located within the subject. Exemplary fungal diseases that can be treated by the methods of the present invention include, but are not limited to, aspergilliosis, crytococcosis, sporotrichosis, coccidioidomycosis, paracoccidioidomycosis, histoplasmosis, blastomycosis, zygomycosis, and candidiasis.

In another aspect, the biological targets are parasites located within the subject. As used herein, the term "parasite" refers to any organism that obtains substance or means for reproduction from an organism, whether it lives with that organism in a parasitic or symbiotic relationship. Exemplary parasitic diseases that can be treated or prevented by the methods of the present invention include, but are not limited to, amebiasis, malaria, *leishmania*, coccidia, giardiasis, cryptosporidiosis, toxoplasmosis, and trypanosomiasis. Also encompassed are infections by various worms, including, but not limited to, *ascariasis*, ancylostomiasis, trichuriasis, strongyloidiasis, toxoccariasis, trichinosis, onchocerciasis, filaria, and dirofilariasis. Also encompassed are infections by various flukes, including, but not limited to, schistosomiasis, paragonimiasis, and clonorchiasis. Examples of human intracellular parasites include *Leishmania* spp.; *Plasmodium* spp., *Trypanosoma cruzi, Toxoplasma gondii, Babesia* spp., and *Trichinella spiralis*. Examples of human extracellular parasites include *Entamoeba histolytica, Giardia lamblia, Enterocytozoon bieneusi, Naegleria* and *Acanthamoeba*, as well as most helminths. Examples of obligate intracellular parasites include *Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

II. Selective Killing of Biological Targets

The present invention is directed to the selective killing of biological targets within a treatment region of a subject, preferably without substantially killing any non-targeted, cells or organisms (collectively "non-targets") within the subject. In order to selectively kill the biological targets within a treatment region without substantially killing the non-targets, the biological targets are heated at a faster rate than the non-targets so that the biological targets reach higher temperatures than the non-targets at the end of the dielectric heating treatment. The manner in which this is accomplished varies depending on the type of the biological targets that are desired to be killed and/or the location of the biological targets in the body. For exemplary purposes, the following discussion involves embodiments in which the biological targets are target cells and the non-targets are non-target cells. As used herein, the term "target cells" refers to the cells within a treatment region that are targeted to be killed with dielectric heating, and the term "non-target cells" refers to the cells within a treatment region that are not targeted to be killed with dielectric heating. In an exemplary embodiment, the "target cells" are neoplastic cells (cancer cells), while the non-targets cells are the non-neoplastic cells (non-cancerous cells) in the treatment region.

A. Target Cells Naturally Heat at Faster Rate Relative to Non-Target Cells

When a treatment region is subjected to a dielectric field, the rate of heating will vary depending on the nature of the different cell types within the treatment region. As will be described in greater detail below, the ratio of the increase in temperature of the target cells to the increase in temperature of the non-target cells is dependent on the dielectric constant, dissipation factor, specific heat and density of the cell types (assuming that the current is substantially constant across the treatment region). As a result, in cases where the target cells and non-target cells have dissimilar dielectric constants, dissipation factors, specific heats, and densities, or combinations thereof, the target cells and non-target cells naturally heat at different rates. For example, adipose cells naturally heat at a faster rate than the other cells in the human body upon application of a dielectric field. Thus, the adipose cells reach higher temperatures than the other cells in the human body at the end of the dielectric heating treatment such that the adipose cells may be selectively killed compared to non-adipose cell types that heat at much lower rates.

Thus, the present invention may be used for the non-surgical removal of fat from a subject such that the target cells are adipose cells. This may involve, for example, prominent and undesired fat deposits on the abdomen, buttocks, thighs, arms, and/or chin. Such local accumulations of body fat (alternatively known as fat maldistribution) may result from disease, hormonal status, or as side effects of medication or other substances. Even in the absence of disease, cosmetic considerations apply to individuals who nevertheless perceive an excess or maldistribution of fat and wish to have it corrected.

It is contemplated that the present invention will reduce the abnormal accumulation of adipose cells in the abdomen, specifically in the visceral adipose tissue compartment in subjects that have this symptom. The present invention may also be used to treat fat deposits in the dorsocervical area ("buffalo hump"), the submandibilar area ("horse collar"); the pectoral, mammary, and/or supraclavicular areas, and/or with subcutaneous lipomas (encapsulated benign fatty tumors, single or multiple).

Further, a dielectric heating modulator may optionally be administered to the subject in order to further increase the rate at which the adipose cells heat compared to the non-target cells. Suitable dielectric heating modulators are discussed below. The dielectric heating modulator may or may not have a targeting moiety specific for the target cells (i.e. the adipose cells) associated therewith. The targeting moiety may comprise an antibody or antibody fragment that selectively binds to a target antigen found on adipocytes. The targeting moiety specific for the target cells is attached to the dielectric heating modulator, and thus the targeting moiety permits the selectively binding of the dielectric heating modulator to the target cells which are adipose cells.

B. Heating Rate of Target Cells Increased Relative to Non-Target Cells

In cases where the target cells and non-target cells have similar dielectric constants, dissipation factors, specific heats, and densities, or combinations thereof, the target cells and non-target cells naturally heat at substantially the same or similar rates. In accordance with the present invention, the heating rate of the target cells relative to the non-target cells can be increased by introducing into the treatment region a dielectric heating modulator (which may be or may not be associated with a targeting moiety) prior to the application of the dielectric field.

In one aspect, the net effect of the dielectric heating modulator is to increase the heating rate of the target cells by increasing the heat generated within and/or transferred to the target cells. In essence, the dielectric heating modulator provides the target cells with a new higher "effective dissipation factor" by virtue of the dielectric heating modulator being associated with the target cells (for example, by specific binding of the targeting moiety to a cell surface receptor, internalization, or local administration of the dielectric heating modulator to the target cells). If the effective dissipation factor of the target cells (having the dielectric heating modulator associated therewith) is greater than the dissipation factor of the non-target cells (having no dielectric heating modulator associated therewith) by a factor of X, then the heating rate of the target cells will also increase by a factor of X compared to the heating rate of the non-target cells. As such, upon application of the dielectric field, the target cells heat at a faster rate than the non-target cells such that the target cells may be selectively killed.

The dielectric heating modulator may be administered to the subject in any manner known to those skilled in the art. Exemplary delivery methods include, but are not limited to, oral, intravenous, intraperitoneal, intramuscular, rectal, intravaginal, subcutaneous, or topical. Thus, the dielectric heating modulator may be administered locally or systemically, although the use of a targeting moiety associated with the dielectric heating, modulator is preferred for systemic administration. Regardless of the delivery method, the dielectric heating modulator (with or without a targeting moiety associated therewith) is preferably administered in a pharmaceutically acceptable carrier, such as a solution, dispersion, or emulsion, as discussed in further detail below.

Thus, in one aspect, the dielectric heating modulator is locally administered to the treatment region containing the target cells. For example, an aqueous solution containing suspended particles of the dielectric heating modulator may be injected into the treatment region containing the target cells (e.g., a cancerous tumor) by means of a needle and syringe. In such a case, the dielectric heating modulator is dispersed, suspended within, or otherwise absorbed or internalized by the target cells (e.g., the cancer cells). The dielectric field is then applied to the treatment region containing the target cells, whereby the target cells heat at a faster rate than the non-target cells such that the target cells may be selectively killed.

In another aspect, the dielectric heating modulator is associated with a targeting moiety for systematic administration. In general, the targeting moiety selectively binds to a target structure on or within the target cells, thereby selectively associating with or otherwise delivering the dielectric heating modulator to the target cells. Once a high enough concentration of the dielectric heating modulator is associated with the target cells (typically by being attached to the target cells or internalized therein), the dielectric field is applied to the treatment region containing the target cells, whereby the target cells heat at a faster rate than the non-target cells such that the target cells may be selectively killed. One skilled in the art will appreciate that the use of a dielectric heating modulator having a targeting moiety associated therewith may be especially useful for killing target cells that do not manifest themselves in a localized region (e.g., blood cancers such as lymphoma, leukemia, and multiple myeloma).

1. Dielectric Heating Modulator

As used herein, the term "dielectric heating modulator" refers to a substance that, when associated with a biological target, is capable of increasing, the heating rate of the biological target when subjected to a dielectric field. Exemplary dielectric heating modulators that increase the heating rate of a biological target include, but are not limited to, electrically conductive materials, polar materials, ionic materials, and combinations thereof. It will also be appreciated that the dielectric heating modulator may be classified as one or more of the foregoing e.g., a polar molecule that is also electrically conductive). Of course, one skilled in the art will understand that other dielectric heating modulators may also be used in accordance with the present invention.

The size of the dielectric heating modulator is preferably in the micron to nanometer range. In most instances, the dielectric heating modulator comprises a nanoparticle. As used herein, the term, "nanoparticle" means a particle having at least one dimension that is less than about 1 micron. Preferably, the dielectric heating modulator has a particle size less than about 1 micron (e.g., about 900, 800, 700, 600, 500, 400, 300, 200, 100 nm or less, or some range therebetween). In another aspect, the particle size is about 1, 5, 10, 15, 20, 30, 40, 50, 60, 70, 80, 90 100 nm, or some range therebetween. Preferably, the dielectric heating modulator is biologically compatible, non-immunogenic, and non-toxic to the human body when delivered in effective amounts. The dielectric heating modulator particles may comprise spheres, rods, flakes, fibrils, discs, bars, tubes, or have an irregular shape, such as a starfish shape.

In general, it is anticipated that for a given dielectric heating modulator, particles of smaller size and increased surface area are preferred. For example, for a given mass of dielectric heating modulator administered to a subject, it is anticipated that smaller particles (e.g., 10 nm) are preferable to larger particles (e.g., 100 nm). Further, it is anticipated that particle shapes affect the dissipation factor of the dielectric heating modulator.

The effective amount of dielectric heating modulator that is administered to a subject may readily be determined by one skilled in the art by using the teachings discussed herein. Those skilled in the art will appreciate that the quantity of dielectric heating modulator will be limited by toxic or other adverse effects. However, it is anticipated that synergistic arcing effects may be observed with some dielectric heating modulators. For example, if the dielectric heating modulator is concentrated on a cell surface, within a cellular compartment, or inside discrete locations of an organism (for example, in the case of a parasite that, has ingested several particles of the dielectric heating modulator), current may arc between adjacent particles or particles that are otherwise proximate to one another during application of the dielectric field.

Further, it will be appreciated to those skilled in the art that there may be some time delay between administration of the dielectric heating modulator (with or without a targeting moiety associated therewith) and the application of the alternating electric field. For example, after administration of an effective amount of the dielectric heating modulator, a time delay of seconds up to hours may occur prior to application of the alternating electric field, for example about 5, 10, 30, 46, 60 seconds, 1, 2, 5, 10, 15, 25, 30, 35, 40, 45, 50, 55, 60 minutes, 1, 1.5, 2, 2.5, 3, 3.5, 4, 4.5, 5, 5.5, 6 hours. The time delay will generally depend on the nature of the dielectric heating modulator, the nature of the targeting moiety, the amount of the dielectric heating modulator, and the route of administration.

In one aspect, the dielectric heating modulator comprises an electrically conductive material. As used herein, the term "electrically conductive material" refers to any material that is capable of conducting electrical current. For example, the electrically conductive material may comprise electroconductive metal particles, such as particles of nickel, iron, copper, zinc, chromium, cobalt, aluminum, silver, gold, iridium, platinum, palladium, zirconium, tin, and the like, as well as particles of alloys of at least two of such metals which exhibit electroconductivity. The metal particles can be in the form of powders, fibers, or flakes. The electrically conductive material may also comprise one or more metal salts, metal oxides, metal colloids, or other metal complexes. Inorganic metal salts include, for example, chlorides, sulfates, and nitrates of these metals (e.g., iron sulfate, copper sulfate, and/or magnesium sulfate). Organic metal salts include, for example, acetates and formates of these metals. Metal complexes include those with bidentate, tridentate, or tetradentate ligand. Exemplary ligands include organic molecules, such as salens, metalloporphyrin, phthalocyanine, macrocyclic teraaza, and cyclam-type ligand systems.

For example, suitable iron salts include, but are not limited to, ferric hypophosphite, ferric albuminate, ferric chloride, ferric citrate, ferric oxide saccharate, ferric ammonium citrate, ferrous chloride, ferrous gluconate, ferrous iodide, ferrous sulfate, ferrous lactate, ferrous fumarate, heme, ferric trisglycinate, ferrous bisglycinate, ferric nitrate, ferrous hydroxide saccharate, ferric sulfate, ferric gluconate, ferric aspartate, ferrous sulfate heptahydrate, ferrous phosphate, ferric ascorbate, ferrous formate, ferrous acetate, ferrous, malate, ferrous glutamate, ferrous cholinisocitrate, ferroglycine sulfate, ferric oxide hydrate, ferric pyrophosphate soluble, ferric hydroxide saccharate, ferric manganese saccharate, ferric subsulfate, ferric ammonium sulfate, ferrous ammonium sulfate, ferric sesquichloride, ferric choline citrate, ferric manganese citrate, ferric quinine citrate, ferric sodium citrate, ferric sodium edetate, ferric formate, ferric ammonium oxalate, ferric potassium oxalate, ferric sodium oxalate, ferric peptonate, ferric manganese peptonate, ferric acetate, ferric fluoride, ferric phosphate, ferric pyrophosphate, ferrous pyrophosphate, ferrous carbonate saccharated, ferrous carbonate mass, ferrous succinate, ferrous citrate, ferrous tartrate, ferric fumarate, ferric succinate, ferrous hydroxide, ferrous nitrate, ferrous carbonate, ferric sodium pyrophosphate, ferric tartrate, ferric potassium tartrate, ferric subcarbonate, ferric glycerophosphate, ferric saccharate, ferric hydroxide saccharate, ferric manganese saccharate, and ferrous ammonium sulfate, ferric sodium pyrophosphate, ferrous carbonate, ferric hydroxide, ferrous oxide, ferric oxyhydroxide, and ferrous oxalate.

Examples of suitable iron complexes include, but are not limited to, polysaccharide-iron complex, methylidine-iron complex, ethylenediaminetetraacetic acid (EDTA)-iron complex, phenanthrolene iron complex, p-toluidine iron complex, ferrous saccharate complex, ferrlecit, ferrous gluconate complex, ferrum vitis, ferrous hydroxide saccharate complex, iron-arene sandwich complexes, acetylacetone iron complex salt, iron-dextran complex, iron-dextrin complex, iron-sorbitol-citric acid complex, saccharated iron oxide, ferrous fumarate complex, iron porphyrin complex, iron phtalocyamine complex, iron cyclam complex, dithiocarboxy-iron complex, desferrioxamine-iron complex, bleomycin-iron complex, ferrozine-iron complex, iron perhaloporphyrin complex, alkylenediamine-N,N-disuccinic acid iron(III) complex, hydroxypyridone-iron(III) complex, aminoglycoside-iron complex, transferrin-iron complex, iron thiocyanate complex, iron complex cyanides, porphyrinato iron(III) complex, polyaminopolycarbonate iron complexes, dithiocarbamate iron complex, adriamycin iron complex, anthracycline-iron complex, N-methyl-D-glucamine dithiocarbamate (MGD)-iron complex, ferrioxamine B, ferrous citrate complex, ferrous sulfate complex, ferric gluconate complex, ferrous succinate complex, polyglucopyranosyl iron complex, polyaminodisuccinic acid iron complex, biliverdin-iron complex, deferiprone iron complex, ferric oxyhydride-dextran complex, dinitrosyl dithiolato iron complex, iron lactoferrin complexes, 1,3-ethylenediaminetetraacetic acid (EDTA) ferric complex salts, diethylenetriaminepentaacetic acid iron complex salts, cyclohexanediaminetetraacetic acid iron complex salts, methyliminodiacetic acid iron complex salts, glycol ether diaminetetraacetic acid iron complex salts, ferric hydroxypyrone complexes, ferric succinate complex, ferric chloride complex, ferric glycine sulfate complex, ferric aspartate complex, sodium ferrous gluconate complex, and ferrous hydroxide polymaltose complex.

Examples of suitable copper salts and complexes include, but are not limited to, copper sulfate (cupric sulfate), copper nitrate, copper phosphate, copper fluoride, copper gluconate, copper chelate, copper histadyl chelate, copper peptide chelate, copper EDTA, copper EGTA, cupric acetate, cupric borate, cupric bromide, cupric butyrate, cupric carbonate, cupric chlorate, cupric chloride, cupric chromate, cupric citrate, cupric formate, cupric glycinate, cupric hydroxide, cupric nitrate, cupric oleate, cupric oxalate, cupric oxide, cupric perchlorate, cupric phosphate, cupric salicylate, cupric selenate, cupric stearate, cupric sulfide, cupric tartrate, cuprous acetate, cuprous borate, cuprous bromide, cuprous butyrate, cuprous carbonate, cuprous chlorate, cuprous chloride, cuprous chromate, cuprous citrate, cuprous formate, cuprous glycinate, cuprous hydroxide, cuprous iodide, cuprous nitrate, cuprous oleate, cuprous oxalate, cuprous oxide, cuprous perchlorate, cuprous phosphate, cuprous salicylate, cuprous selenate, cuprous stearate, cuprous-sulfide, and cuprous tartrate.

Examples of suitable silver salts include, but are not limited to, silver agetate, silver borate, silver bromide, silver butyrate, silver carbonate, silver chlorate, silver chloride, silver chromate, silver citrate, silver formate, silver glycinate, silver hydroxide, silver iodide, silver nitrate, silver oleate, silver oxalate, silver oxide, silver perchlorate, silver phosphate, silver salicylate, silver selenate, silver stearate, silver sulfide, and silver tartrate.

Examples of suitable gold salts include, but are not limited to, gold acetate, gold borate, gold bromide, gold butyrate, gold carbonate, gold chlorate, gold chloride, gold chromate, gold citrate, gold formate, gold glycinate, gold hydroxide, gold iodide, gold nitrate, gold oleate, gold oxalate, gold oxide, gold perchlorate, gold phosphate, gold salicylate, gold selenate, gold stearate, gold sulfide, and gold tartrate.

Examples of suitable aluminum salts include, but are not limited to, aluminum acetate, aluminum borate, aluminum bromide, aluminum butyrate, aluminum carbonate, aluminum chlorate, aluminum chloride, aluminum chromate, aluminum citrate, aluminum formate, aluminum glycinate, aluminum hydroxide, aluminum iodide, aluminum nitrate, aluminum oleate, aluminum oxalate, aluminum oxide, aluminum perchlorate, aluminum phosphate, aluminum salicylate, aluminum selenate, aluminum stearate, aluminum sulfide, and, aluminum tartrate.

The dielectric heating modulator may also comprise an electrically conductive material that is an electrocatalyst nanoparticle. In general, the electrocatalyst is comprised of a metallic catalytic material and a carbon particle. The carbon particle is comprised of a material that supports the metallic catalytic material, such as acetylene black (Denka Black® available from Denki Kagaku Kogyo K.K.), Vulcan XC72 (available from Cabot Corporation), ketjen black, amorphous carbon, carbon nanotube, and carbon nanohorn. A preferred electrocatalyst is the Dynalyst family of electrocatalysts (available from Cabot Corporation), particularly Dynalyst 50KR1 which is 50% Pt/ketjen black.

Non-metallic electrically conductive materials are also suitable for use in accordance with the present invention, such as Black pearl 2000 (available from Cabot Corporation) which has a large surface area and those described in carbon particles described above, as well as Gannon et al., *Carbon nanotube-enhanced thermal destruction of cancer cells in a noninvasive radiofrequency field*, Cancer. December 15, 110(12) 2654-65: (2007); Gannon et al., *Intracellular gold nanoparticles enhance non-invasive radiofrequency thermal destruction of human gastrointestinal cancer cells*, Nanobiotechnology, January 30, 6:2 (2008); and U.S. Pat. No. 4,303,636. Thus, electrically conductive materials comprising carbon include all types of conductive carbon blacks, many of which are known in the art. Carbon nanofibers and nanotubes are also suitable for use and can have any suitable surface area or aspect ratio, but typically will have an aspect ratio of about 25 or more (e.g., about 25 to about 250, or about 50 to about 150).

In another aspect, the dielectric heating modulator comprises a polar material. As used herein, the terms "polar molecule" or "polar material" refer to an electrically neutral molecule that exhibits non-zero electric dipole moment caused by significant electron shift in at least one covalent bond related to the same molecule. Exemplary polar materials have functional groups selected from carboxyl, hydroxyl, ester, carbonyl, ether, nitrile, amine, amide, and halogen groups. Exemplary polar molecules include water-soluble polymers such as polyvinylpyrrolidone, polyethylene oxide, polyalkylene glycol (especially polyethylene glycol), and the like, as well as water-soluble polydextrose, saccharides and polysaccharides, such as pullulan, dextran, sucrose, glucose, lactose, maltose, xylose, arabiniose, ribose, fructose, mannitol, mannose, galactose, sorbitol and the like. Other examples of polar materials include monohydric and polyhydric alcohols and amines, such as ethanol and triethanol amine. The polar material may have a lactam group, preferably substituted and unsubstituted 4 to 7 membered lactam rings. Suitable substituents include C1-3 alkyl groups and aryl groups. Preferred lactams include substituted and unsubstituted 4 to 6 membered lactams and most preferably unsubstituted 4 to 6 membered lactams. Examples of suitable lactams include N-vinyllactams such as N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, N-vinylmaleimide, vinylsuccinimide, mixtures thereof and the like. Preferred lactams include heterocyclic monomers containing 4 carbon atoms in the heterocyclic ring. A highly preferred vinyllactam is N-vinyl-2-pyrrolidone.

Preferred polar molecules are those that are naturally occurring molecules in the body or mimics thereof, such as glucose, glucose mimics, and their metabolites. A preferred polar molecule is 2-deoxyglucose and its derivatives. Such compounds are preferentially taken up by cancer cells, and thus are well-suited for use in the present invention when the biological targets are cancer cells.

In another aspect, the dielectric heating-modulator comprises an ionic material. The term "ionic material" refers to those materials with at least one charge on the molecule, for example anionic (negatively charged), cationic (positively charged), or zwitterionic (both positively and negatively charged) compounds. Ionic materials include acids, bases, and salts. Exemplary ionic materials include amino acids, proteins, and nucleic acids. Exemplary acids comprise at least one carboxylic acid, phosphoric acid or sulphonic acid functional group. Exemplary bases include sodium hydroxide and potassium hydroxide. Exemplary salts include metal salts, such as aluminum oxidelithium carbonate, sodium chloride, sodium bromide, potassium chloride, potassium sulfate, potassium phosphate, sodium acetate, sodium citrate, and the like.

2. Targeting Moiety

The dielectric heating modulator may also be associated with a targeting moiety. As used herein, the term "targeting moiety" refers to a substance, means, or technique of selectively delivering the dielectric heating modulator to the biological targets (compared to the non-targets). The targeting moiety may be directly linked or indirectly associated with the dielectric heating modulator. In most instances, the dielectric heating modulator is conjugated to the targeting moiety, for example by a covalent bond. The targeting moiety could also be indirectly associated with the dielectric heating modulator, for example if the targeting moiety forms part of a liposome or other carrier for the dielectric heating modulator. Preferably, the targeting moiety is biologically compatible and non-toxic to the human body.

In one aspect, the targeting moiety interacts with a target structure on or within the biological target. In general, target structures contemplated by the present invention that interact with and/or selectively bind to the targeting moiety include, but are not limited to, cell surface proteins, cell surface receptors, cell surface polysaccharides, extracellular matrix proteins, intracellular proteins, intracellular nucleic acids, and the like. In some cases, the target structure is located on the surface of a cell (e.g., cancer cells). In other cases, the target structure is located within the cell (e.g., nucleic acids). The range of target structures is virtually unlimited. Indeed, any inter-biological or intra-biological feature (e.g., glycoprotein) of a cell or tissue is encompassed as a target structure within the present invention. For example, target structures may include epitopes selected from a viral coat protein, a bacterial cell wall protein, or a viral or bacterial polysaccharide.

In another aspect, the targeting moiety selectively binds to a target structure that is a tumor-associated antigen on the cancer cell. Tumor associated antigens include, but are not limited to, products of mutated oncogenes and tumor suppressor genes, products of other mutated genes, overexpressed or aberrantly expressed cellular proteins, tumor antigens produced by oncogenic viruses, oncofetal antigens, altered cell surface glycolipids and glycoproteins, and cell type-specific differentiation antigens. In one example, the tumor associated antigen is selected from the group consisting of tumor associated glycoprotein-72 (TAG-72, a pan-carcinoma antigen, Kjeldsen et al., *Preparation and Characterization of Monoclonal Antibodies Directed to the Tumor-associated O-linked Sialosyl-2→6' α-N-Acetylgalactosaminyl (Sialosyl-Tn) Epitope*, Cancer Res. 48 2214-2220 (1988); U.S. Pat. No. 5,892,020; U.S. Pat. No. 5,892,019; and U.S. Pat. No. 5,512,443), tumor associated antigens human carcinoma antigen (U.S. Pat. No. 5,693,763; U.S. Pat. No. 5,545,530; and U.S. Pat. No. 5,808,005); TP1 and TP3 antigens from osteocarinoma cells (U.S. Pat. No. 5,855,866); Thomsen-Friedenreich (TF) antigen from adenocarcinoma cells (U.S. Pat. No. 5,110,911); KC-4 antigen from human prostrate adenocarcinoma (U.S. Pat. No. 4,708,930 and U.S. Pat. No. 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. No. 4,963,484 and U.S. Pat. No. 5,053,489); a human breast tumor antigen (U.S. Pat. No. 4,939,240); p97 antigen of human melanoma (U.S. Pat. No. 4,918,164); carcinoma or orosomucoid-related antigen (CORA) (U.S. Pat. No. 4,914,021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., *Blood group Tn-active macromolecules from human carcinomas and erythrocytes: Characterization of and specific reactivity with mono-and poly-clonal anti-Tn antibodies induced by various immunogens*, Carbohydr. Res. 178 271-292 (1988)), MSA breast carcinoma glycoprotein (Tjandra et al., *Application of mammary serum antigen assay in the management of breast cancer: A preliminary report*, British J. Surgery 75 811-817 (1988)); MFGM breast carcinoma antigen (Ishida et al., *Related Glycoproteins from Normal Secretory and Malignant Breast Cells: Purification and Initial Comparative Characterizations*, Tumor Biol., 10 12-22. (1989)); DU-PAN-2 pancreatic carcinoma antigen (Lan et al., *Isolation and Properties of a Human Pancreatic Adenocarcinoma-associated Antigen, DU-PAN-21*, Cancer Res. 45 305-310 (1985)); CA-125 ovarian carcinoma antigen (Hanisch et al., *Structural studies on oncofetal carbohydrate antigens (Ca 19-9, Ca 50, and Ca 125) carried by O-linked sialyl-oligosaccharides on human amniotic mucins*, Carbohydr. Res. 178 29-47 (1988)); YH206 lung carcinoma antigen (Hinoda et al., *Immunochemical characterization of adenocarcinoma-associated antigen yh206*, Cancer J. 42 653-658: (1988), alphafetoprotein (AFP), carcioembryonic antigen (CEA), MUC-1 (breast cancer), melanoma-associate antigens (MAGE), carbohydrate antigen 19-9 (CA19.9), prostate specific antigen (PSA), and B melanoma antigen (BAGE). The targeting moiety may also target the products of oncogenes or tumor suppressors. Oncogene products include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc, and bcl-2 and family members. Thus, examples of oncogene products include, but are not limited to, as ras, src, abl, fgr, rel, yes, fes, net, mos, raf, erb B, erb A, fins, neu, ros, kit, sea, sis, myc, myb, fos, ski, jun and ets. Examples of tumor suppressors include, but are not limited to, Muc 1, CCAM, RB, APC, DCC, MEN-I, MEN-II, zac1, MMAC1, FCC, MCC p16, p21, p27, p53, p73, zac1, MMAC1, Rb, Wilms tumor (WT-1), DCC, neurofibromatosis type 1 (NF-1), NF-2, von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, CD63, R2, CD81, CO029, TI-1, L6 and SAS. Of course, these are merely exemplary oncogene products and tumor suppressors and it is envisioned that the present invention may be used in conjunction with other types of agents that are known to those skilled in the art.

The present invention is not limited to any particular targeting moiety. Indeed, a variety of targeting moieties are contemplated by the invention. Examples of targeting moieties include, but are not limited to, nucleic acids (e.g., RNA and DNA), polypeptides (e.g., receptor ligands, signal peptides, avidin, Protein A, antigen binding proteins fusion proteins, etc.), polysaccharides, biotin, hydrophobic groups, hydrophilic groups, drugs, and any organic molecules that bind to receptors. Exemplary targeting moieties are also described in U.S. Patent Application No. 2007/0248537, U.S. Pat. No. 7,329,638, and U.S. Pat. No. 7,5210,555.

In one aspect, the targeting moiety is an antibody or antibody fragment. In general, the term "antibody" refers to immunoglobulin molecules and immunologically active portions of immunoglobulin molecules (molecules that contain an antigen binding, site that specifically binds an antigen), including monoclonal antibodies (e.g., full length monoclonal antibodies), polyclonal antibodies, multispecific antibodies (e.g., bispecific antibodies), chimeric antibodies, CDR-grafted antibodies, humanized antibodies, human antibodies, and single chain antibodies (scFvs). The term "monoclonal antibody" or "monoclonal antibody composition" refers to a population of antibody molecules that contain only one species of an antigen binding site capable of recognizing and binding to a particular epitope of a target antigen. A monoclonal antibody composition typically displays a single binding specificity and affinity for a particular target antigen with which it immunoreacts. The term "single-chain antibody" refers to a protein having a two-polypeptide chain structure consisting of a heavy and a light chain, said chains being stabilized, for example, by interchain peptide linkers, which has the ability to specifically bind antigen. Techniques for producing single chain antibodies specific to target antigen are described, for example, in U.S. Pat. No. 4,946,778.

The term "antibody fragment" refers to F(ab')2 fragments, Fab fragments, Fab' fragments, Fd fragments, Fv fragments, and single domain antibody fragments (DAbs). Immunologically active portions of immunoglobulins include, for example, F(ab) and F(ab')2 fragments. Methods for the construction of Fab fragments are described, for example, in Huse, et al., *Generation of a large combinatorial library of the immunoglobulin repertoire in phage lambda*, Science 246 1275-1281 (1989). Other antibody fragments may be produced by techniques known in the art, including, but not limited to: (1) an F(ab')2 fragment produced by pepsin digestion of an antibody molecule; (2) a Fab fragment generated by reducing the disulfide bridges of an F(ab')2 fragment; (3) a Fab' fragment generated by the treatment of the antibody molecule with papain and a reducing agent; and (4) Fv fragments. Various antibody fragments can also be produced by art-recognized recombinant engineering techniques. Non-human antibodies can be "humanized" by techniques described, for example, in U.S. Pat. No. 5,225,539. In one method, the non-human CDRs are inserted into a human antibody or consensus antibody framework sequence. Further changes can then be introduced into the antibody framework to modulate affinity or immunogenicity.

As discussed above, in one aspect, the targeting moiety recognizes a target structure which is a tumor-associated antigen that is found specifically on neoplastic cells and not on normal cells. In a preferred example, the targeting moiety is an antibody or antibody fragment that specifically recognizes cancer cells but does not recognize normal, non-cancerous cells. As a specific example, the targeting moiety may selectively bind to Ep-CAM (Epithelial Cell Adhesion Molecule), also known as 17-1A, KSA, EGP-2, and GA733-2. Ep-CAM is a transmembrane protein that is highly expressed in many solid tumors, including carcinomas of the lung, breast, ovary, colorectum, and squamous cell carcinoma of the head and neck, but weakly expressed in most normal epithelial tissues. Accordingly, the invention provides for a targeting moiety associated with a dielectric heating modulator in which the targeting moiety selectively binds to Ep-CAM on the cancer cell. In a specific example, the targeting moiety comprises an antibody or antibody fragment that binds to the extracellular domain of human Ep-CAM. The targeting moiety may be joined directly to the dielectric heating modulator or through a linker. In one embodiment, the linker is a peptide linker or a chemical linker. Methods for linking a dielectric heating modulator, such as gold nanoparticles, to a targeting moiety, such as antibodies, are known in the literature. See generally Glazer et al., *Radiofrequency field-induced thermal cytotoxicity in cancer cells treated with fluorescent nanoparticle*, Cancer. 116(13) 3285-3293 (2010); Curley et al., *Noninvasive radiofrequency field-induced hyperthermic cytotoxicity in human cancer cells using cetuximab-targeted gold nanoparticles*, J Exp Ther. Oncol. 7(4) 313-326 (2008). Methods for linking gold nanoparticles to 2-deoxyglucose are described in Aydogan et al., *AuNP-DG: Deoxyglucose-Labeled Gold Nanoparticles as X-ray Computed Tomography Contrast Agents for Cancer Imaging*, Mol Imaging Biol. 2010 October; 12(5):463-7 and Li et al., *A novel functional CT contrast agent for molecular imaging of cancer*, Phs. Med. Biol, 55, 4389-4397 (2010). It will be appreciated to those skilled in the art that other targeting moiety-dielectric heating modulator conjugates may be produced in which the anti-Ep-CAM antibody is replaced with another antibody or antibody fragment specific for another tumor associated antigen.

In yet another example, the targeting moiety comprises peptides that bind specifically to the target cells, such as tumor blood vessels (see e.g., Arap et al., *Cancer treatment by targeted drug delivery to tumor vasculature in a mouse model*, Science 279 377-80 (1998)). These peptides include, but are not limited to, peptides containing the RGD (Arg-Gly-Asp) motif, the NGR (Asn-Gly-Arg) motif, or the GSL (Gly-Ser-Leu) motif. These peptides and conjugates containing these peptides selectively bind to various tumors, including, but not limited to breast carcinomas, Karposi's sarcoma, and melanoma. It is not intended that the present invention be limited to a particular mechanism of action. Indeed, an understanding of the mechanism is not necessary to make and use the present invention. However, it is believed that these peptides are ligands for integrins and growth factor receptors that are absent or barely detectable in established blood vessels.

The targeting moiety may also be a "disease receptor targeting ligand," which includes agents exploited for their ability to bind to certain cellular receptors that are overexpressed in disease states, such as cancer, neurological diseases, and cardiovascular diseases. Examples of such receptors which are targeted include estrogen receptors, amino acid transporters, androgen receptors, pituitary receptors, transferrin receptors, progesterone receptors, and glucose transporters. Non-limiting examples of agents that can be applied as disease-receptor targeting ligands include androgen, estrogen, somatostatin, progesterone, transferrin, luteinizing hormone, and luteinizing hormone antibody. Disease receptor targeting ligands (e.g., pentetreotide, octreotide, transferrin, and pituitary peptide) bind to cell receptors, some of which are overexpressed on certain cells.

In another example, the targeting moiety comprises glucose or a glucose mimic. Glucose transporters are overexpressed in various diseased cells such as certain cancerous cells. Tetraacetate mannose, deoxyglucose, certain polysaccharides (e.g., neomycin, kanamycin, tobramycin), and monosaccharides (e.g., glucosamine) also bind the glucose transporter and may be used as disease receptor targeting ligands. Thus, the targeting moiety may be a mimic glucose selected from the group consisting of deoxyglucose, glucosamine, tetraacetylated glucosamine, neomycin, kanamycin, gentamycin, paromycin, amikacin, tobramycin, netilmicin, ribostamycin, sisomicin, micromicin, lividomycin, dibekacin, isepamicin, astromicin, and aminoglycoside. Similarly, amino acid transporters are also overexpressed in various diseased cells such as certain cancerous cells. As such, amino acids and/or amino acid derivatives (e.g., serine, tyrosine, alpha methyltyrosine) may be used as targeting moieties.

The folate receptor is included herein as another example of a disease receptor. Folate receptors (FRs) are overexposed on many neoplastic cell types (e.g., lung, breast, ovarian, cervical, colorectal, nasopharyngeal, renal adenocarcinomas, malignant melanoma, and ependymomas), but primarily express several normal differentiated tissues (e.g., choroid plexus, placenta, thyroid, and kidney) (Weitman et al., *Distribution of the folate receptor GP38 in normal and malignant cell lines and tissues*, Cancer Res. 52 3396-3401 (1992); Campbell et al., *Folate-binding protein is a marker for ovarian cancer"* Cancer Res. 51 5329-5338 (1991); Weitman et al. *Cellular localization of the folate receptor: potential role in drug toxicity and folate homeostasis*, Cancer Res. 52 6708-6711 (1992); Holm et al., *Folate receptor of human mammary adenocarcinonma*, APMIS 102 413-419 (1994); Ross et al., *Differential regulation of folate receptor isoforms in normal and malignant tissue in vivo and in established cell lines*, Cancer 73 2432-2443 (1994); Franklin et al., *New anti-lung-cancer antibody cluster 12 reacts with human folate receptors present on adenocarcinoma*, Int. J. Cancer-Supplement 8 89-95, (1994); Weitman et al., *The folate receptor in central nervous system malignancies of childhood*, J. Neuro-Oncology 21 107-112 (1994)). Folate receptors have been used to deliver folate-conjugated protein toxins, drug/antisense oligonucleotides and liposomes into tumor cells overexpressing the folate receptors (Ginobbi et al., *Folic acid-polylysine carrier improves efficacy of c-myc antisense oligodeoxynucleotides on human melanoma (M14) cells*, Anticancer Res. 17 29-35 (1997); Leamon et al., *Delivery of macromolecules into living cells: a method that exploits folate receptor endocytosis*, Proc. Natl. Acad. Sci. 88 5572-5576 (1991); Leamon et. al., *Cytotoxicity of momordin-folate conjugates, in cultured human cells*, Biol. Chem. 267 2496.6-24971 (1992); Leamon et al., *Cytotoxicity of folate-pseudomonas exotoxin conjugates toward tumor cells*, J. Biol. Chem. 268 24847-24854 (1993); Lee et al., *Delivery of liposomes into cultured KB cells via folate receptor-mediated endocytosis*, J. Biol. Chem. 269 3198-3204 (1994)). Further, bispecific antibodies that contain anti-FR antibodies linked to anti-T cell receptor antibodies have been used to target T cells to FR-positive tumor cells and are currently in clinical trials for ovarian carcinomas (Canevari et al., *Ovarian carcinoma therapy with monoclonal antibodies*, Hybridoma 12 501-507 (1993); Bolhuis et al., *Adoptive immunotherapy of ovarian carcinoma with Bs-MAb targeted lymphocytes. A multicenter study*, Int. J. Cancer 7 78-81 (1992); Patrick et al., *Folate receptors as potendal therapeutic targets in choroid plexus tumors of SV/40 transgenic mice*, J. Neurooncol. 32 111-123, (1.997); Coney et. al., *Chimeric murine-human antibodies directed against folate binding receptor are efficient mediators of ovarian carcinoma cell killing*, Cancer Res. 54 2448-2455 (1994); Kranz et al., *Conjugates of folate and anti-T-cell-receptor antibodies specifically target folate-receptor-positive tumor cells for lysis*, Proc. Natl. Acad. Sci. 92 9057-9061 (1995)).

Thus, in another aspect, the targeting moieties comprise folate receptor targeting ligands, such as folic acid and analogs of folic acid. In certain embodiments, a folate receptor targeting ligand is selected from the group consisting of folate, folic acid, methotrexate, and tomudex. Folic acid as well as antifolates such as methotrexate enter into cells via high affinity folate receptors (glycosylphosphatidylinositol-linked membrane folate-binding protein) in addition to classical reduced-folate carrier system (Westerhof et al., *Membrane transport of natural folates and antifolate compounds in murine L*1210 *leukemia cells: Role of carrier- and receptor-mediated transport systems*, Cancer Res. 51 5507-5513 (1991); Orr et al., *Similarity of folate receptor expression in UMSCC* 38 *cells to squamous cell carcinoma differentiation markers*, J. Natl. Cancer Inst. 87 299-303 (1995); Hsuch et al., *Altered folate-binding protein mRNA stability in KB cells grown in folate-deficient medium,"* Biochem. Pharmacol. 45 2537-2545 (1993)).

In addition, the present invention contemplates that vitamins (both fat soluble and non-fat soluble vitamins) may be used as targeting moieties to target biological targets that have receptors for, or otherwise take up, these vitamins. Particularly preferred for this aspect of the invention are the fat soluble vitamins, such as vitamin D and its analogues, vitamin E, Vitamin A, and the like or water soluble vitamins such as Vitamin C, and the like.

In another example, the targeting moiety is a signal peptide. These peptides are chemically synthesized or cloned, expressed and purified as known in the art. Signal peptides are used to target an electrically conductive material to a discrete region within a cell. In still other embodiments, a signal peptide is provided in addition to a targeting moiety that is responsible for targeting the drug delivery component to a target cell or tissue (e.g., a cancer cell). In some embodiments, specific amino acid sequences in proteins are responsible for targeting the dielectric heating modulator into cellular organelles and compartments.

In another aspect, the targeting moiety is an anaerobic bacteria having the dielectric heating modulator either internalized therein or attached thereto or can be used as a gene delivery vector for the dielectric heating modulator. In this regard, it is known that hypoxic regions are characteristic of solid tumors. In particular, certain species of anaerobic bacteria, including the genera *Clostridium* and *Bifidobacterium*, can selectively germinate and grow in the hypoxic regions of solid tumors.

As another example, the targeting moiety may comprise a magnetic particle. The dielectric heating modulator associated with the magnetic targeting moiety may be steered to specific locations using magnets or magnetic resonant imaging (MRI) machines. Thus, when the targeting moiety comprises a magnetic particle, the dielectric heating-modulator can be directed toward specific target cells using a magnetic force. It will be appreciated that the magnetic force can be either an attracting force or a repelling force. Further, both the targeting moiety and the dielectric heating modulator may be magnetic. For example, the dielectric heating modulator and targeting moiety may comprise a gold nanoparticle partially or wholly coated with ferrous iron. A magnet may then be used to localize the coated particle to the biological targets, such as a localized tumor, prior to or during application of the dielectric heating.

It is also contemplated that the dielectric heating modulator may be associated with multiple targeting moieties. For example, the plurality of molecular recognition elements can be either similar (e.g., monoclonal antibodies) or dissimilar (e.g., distinct idiotypes and/or isotypes of antibodies, or an antibody and a nucleic acid, etc). Utilization of more than one targeting moiety allows multiple biological targets to be targeted or to increase affinity for a particular biological target.

It will be appreciated that in some instances, the dielectric heating modulator itself may have targeting attributes. For example, glucose and glucose mimics are preferentially taken up by cancer cells. That is, like a targeting moiety, glucose and glucose mimics selectively target cancer cells. Such compounds may function as dielectric heating modulators, but also have targeting attributes when the biological targets are cancer cells. As another example, a dielectric heating modulator may be comprised of a magnetic material, in which case-magnets or MRI machines can be used to steer the magnetic dielectric heating modulator toward specific biological targets (e.g., target cells) using an attracting or repelling magnetic force. In these cases, the dielectric heating modulator does not need to be associated with a targeting moiety (wherein the term "targeting moiety" refers to a substance, means, or technique that is distinct from the dielectric heating modulator itself).

3. Carrier

The dielectric heating modulator, without or without a targeting moiety associated therewith, may be administered to the subject in a carrier. Exemplary carriers are described in U.S. Patent Application No. 2007/0248537, U.S. Pat. No. 7,329,638, and U.S. Pat. No. 7,5210,555. Carriers are also detailed in Remington's Pharmaceutical Sciences, latest edition; (Mack Publishing). Preferably, the carrier is a pharmaceutically acceptable carrier, which is generally a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Each carrier must be "acceptable" in the sense of being compatible with the other ingredients of the formulation and not injurious to the subject. In addition, it is preferable that the carrier not substantially interfere with the heating of the dielectric heating modulator. The carrier preferably has properties similar to that of the human body. The carrier may be associated with both a dielectric heating modulator and a targeting moiety. For example, the targeting moiety may be attached or otherwise coupled to a liposome, in which the dielectric heating modulator is encapsulated therein.

III. Application of Dielectric Field to Treatment Region of a Subject

As discussed above, the present invention involves placing a treatment region of a subject between two electrodes such that the treatment region effectively becomes the dielectric of a capacitor. A dielectric field generated between the electrodes causes polar molecules in the treatment region to be attracted and repelled by the rapidly changing polarity of the dielectric field. The friction resulting from this molecular movement translates into heat throughout the thickness of each treatment region in such a manner as to provide substantially even heating of the treatment region. By contrast, it will be appreciated that an electromagnetic field utilizes a standing wave whose amplitude decreases as it penetrates into a treatment region and, thus, provides uneven heating of the treatment region. Accordingly, the present invention relies on the use of a dielectric field for its ability to provide substantially even heating throughout the thickness of the treatment region.

Importantly, if a substantially constant current passes between the electrodes and through a treatment region, then the same cell type throughout the treatment region heats at substantially the same rate. In order to obtain a substantially constant current, it is also necessary to obtain a substantially constant, voltage between the electrodes. Accordingly, various exemplary embodiments of apparatuses and methods for generating a dielectric field between two electrodes in accordance with the present invention are described below, wherein the voltage between the electrodes is substantially constant (as described in Section III.A below) and/or the current passing between the electrodes and through the treatment region is substantially constant (as described in Section III.B below). Of course, one-skilled in the art will understand that other apparatuses and methods may also be implemented in accordance with the present invention.

A. Substantially Constant Voltage

Examples are provided below of apparatuses for generating a dielectric field between two electrodes wherein the voltage between the electrodes is substantially constant. It should be noted that these examples are provided to explain the principles that are used to obtain a substantially constant voltage between the electrodes, which is necessary to obtain a substantially constant current between the electrodes and across the treatment region. It will be seen that the examples provided in Section III.B below (which are the preferred embodiments insofar as a substantially constant current is obtained) rely on the principles discussed herein. Also, as used herein, the term "substantially constant voltage" between electrodes i.e., a high voltage electrode and a ground electrode, means that the difference between the voltage provided at a point on the high voltage electrode compared to the voltage provided at each other point on the high voltage electrode is preferably less than ±10%, more preferably less than ±8%, more preferably less than ±6%, more preferably less than ±4%, and most preferably less than ±2%.

Referring to FIG. 1, a diagram of an exemplary apparatus that may be used to generate a dielectric field between two electrodes is designated as reference numeral 10. Apparatus 10 includes a top electrode 12 and a bottom electrode 14 each of which comprises a plate formed of any conductive material. Top and bottom electrodes 12, 14 are connected to an energy source or generator 16 operable to generate a dielectric field between the electrodes. In this example, top electrode 12 is the high voltage electrode while bottom electrode 14 is the ground electrode (although this could be reversed such that the top electrode is the ground electrode and the bottom electrode is the high voltage electrode). The voltage between the electrodes is adjustable and varies between different applications. Typically, the voltage between the electrodes is in the range of 100 volts to 10,000 volts, preferably in the range of 200 volts to 2,000 volts, and more preferably in the range of 300 volts to 500 volts. The dielectric field is generated at frequencies ranging from about 1 MHz to 100 MHz, and is preferably generated at either 27.12 MHz or 40.68 MHz (both of which are allowed center frequencies for industrial, scientific, and medical (ISM) applications). As can be seen, in the illustrated embodiment, the treatment region comprises the entire human body such that top electrode 12 and bottom electrode 14 are positioned proximate to and on either side of body and are sized to extend across the surface area of the body. Of course, the size of the electrodes will vary depending on the surface area of the treatment region.

Generator 16 contains a power tube and LC circuit, or may alternatively contain solid-state technology. Preferably, generator 16 is tuned to resonate at the selected frequency, which occurs when the inductive reactance balances the capacitive reactance at the selected frequency, as follows:

$$f = \frac{1}{2\pi\sqrt{LC}} \quad (1)$$

where
f=frequency of dielectric field in hertz
L=inductance in henries
C=capacitance in farads.

Figure 2:
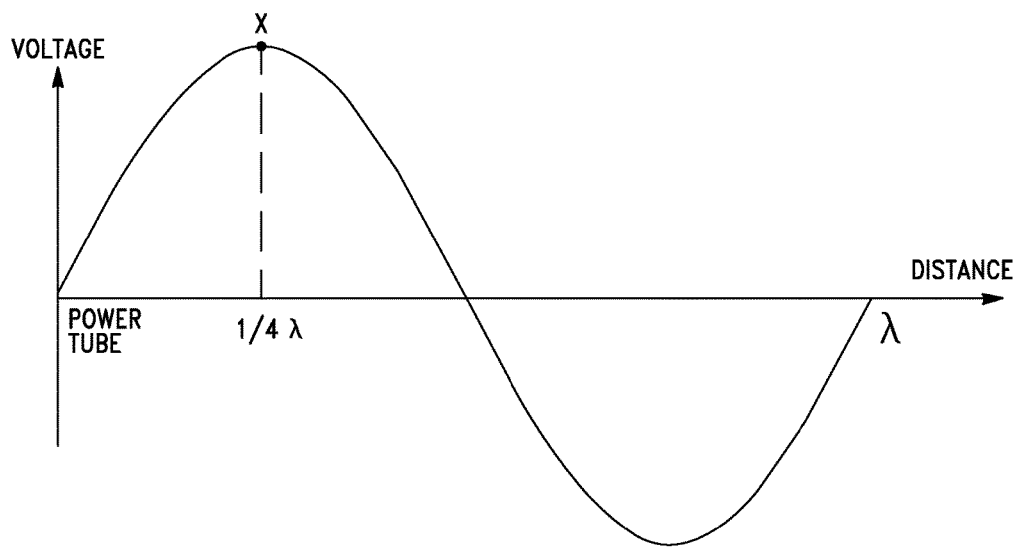
FIG. 2 shows the signal generated by the apparatus of FIG. 1, wherein the signal is substantially a sinusoid having a wavelength λ and wherein a single point (designated as point X) is located at the ¼ wavelength position.

As shown in FIG. 2, the signal generated by the apparatus of FIG. 1 is substantially a sinusoid having a wavelength λ. Preferably, the treatment region is placed between top electrode 12 and bottom electrode 14 and generally centered at a position that is ¼λ or, alternatively, ¼λ plus a multiple of ½λ (e.g., ¾λ, 1¼λ, etc.), from the power tube of generator 16. It can be seen that the peak of the sinusoid is located at these positions, which provides the most constant voltage (i.e., the lowest voltage change) on the sinusoid.

The wavelength of the sinusoid is expressed as follows:

$$\lambda = \frac{c}{f} \quad (2)$$

where
λ=wavelength of sinusoid in meters
c=speed of light (3×10⁸ m/sec)
f=frequency of dielectric field in hertz.

Using this equation, the wavelength of a sinusoid for a dielectric field generated at 27.12 MHz is as follows:

$$\lambda = \frac{3 \times 10^8}{27.12 \times 10^6} = 11.1 \text{ meters} = 36.3 \text{ feet} \quad (3)$$

Thus, the ¼λ position is located 9.1 feet from the power tube of generator 16.

Similarly, the wavelength of a sinusoid for a dielectric field generated at 40.68 MHz is as follows:

$$\lambda = \frac{3 \times 10^8}{40.68 \times 10^6} = 7.5 \text{ meters} = 24.6 \text{ feet} \quad (4)$$

Thus, the ¼λ position is located 6.15 feet from the power tube of generator 16.

One skilled in the art will understand that the use of a lower frequency (e.g., 27.12 MHz) will provide more consistent voltages between electrodes 12 and 14 due to the longer wavelength λ of the generated signal. However, the use of a higher frequency (e.g., 40.68 MHz) will heat the treatment region at a faster rate. Thus, for any given application, the desired frequency may be selected with these considerations in mind. Of course, the surface area of the treatment region may dictate the desired frequency. For example, if a treatment region has, a surface area of 18 inches by 24 inches, it is possible to use a higher frequency (e.g. 40.68 MHz). However, if the treatment region comprises the entire human body, as in the illustrated embodiment, it would be preferable to use a lower frequency (e.g., 27.12 MHz).

As discussed above, apparatus 10 shown in FIG. 1 may be used to apply substantially constant voltages between electrodes 12 and 14 if the treatment region is placed at or near the ¼λ position (or, alternatively, A ¼λ plus a multiple of ½λ). With this electrode configuration, a single point (designated as point X in FIGS. 1 and 2) is located at the ¼ wavelength position (or, alternatively, ¼λ plus a multiple of ½λ), which corresponds to the highest voltage on the sinusoid. In order to apply even more consistent voltages between the electrodes, top electrode 12 may be replaced with a top electrode in which a plurality of points are located at the ¼ wavelength position (or, alternatively, ¼λ plus a multiple of ½λ), as will be described below.

Figure 3:
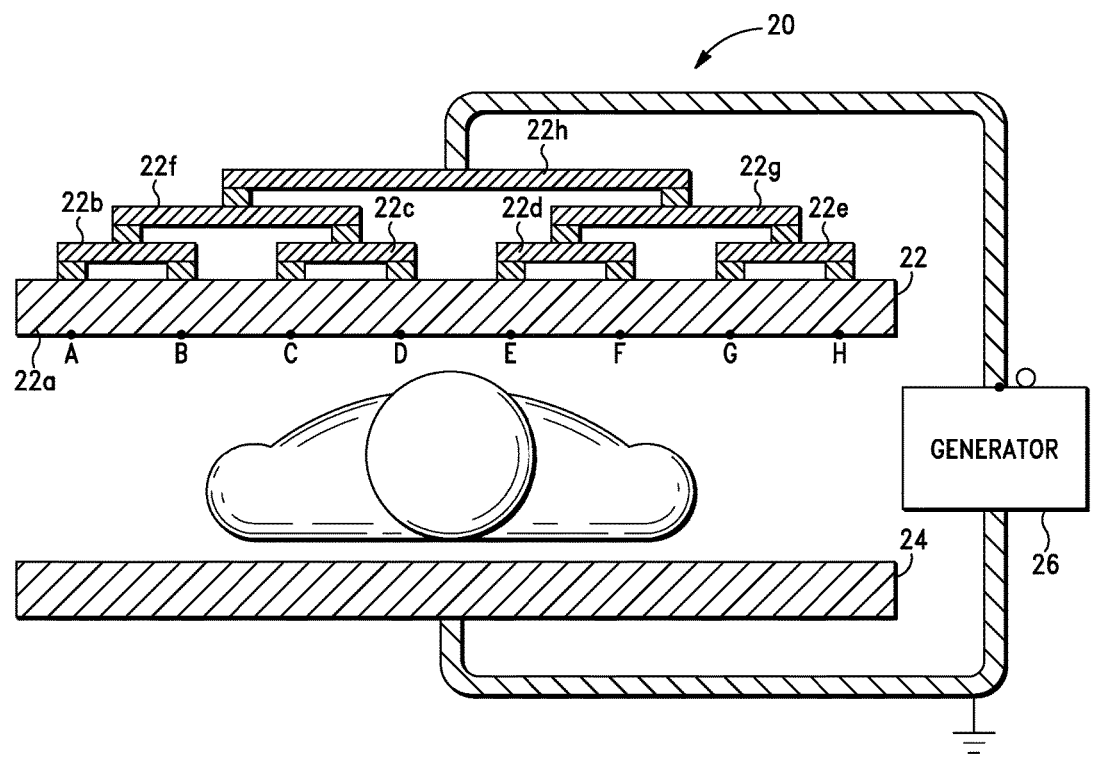
FIG. 3 is a diagram of an exemplary apparatus for generating an alternating electric field between a top electrode comprising a plurality of tiered plates and a single-plate bottom electrode, wherein the voltage between the top and bottom electrodes is substantially constant.

Referring to FIG. 3, a diagram of an exemplary apparatus that may be used to generate a dielectric field between two electrodes is designated as reference numeral 20. Apparatus 20 includes a top electrode 22 and a bottom electrode 24, both of which are connected to an energy source or generator 26 operable to generate a dielectric field between the electrodes. It should be understood that the only difference between apparatus 10 of FIG. 1 and apparatus 20 of FIG. 3 is the configuration of the top electrode. In FIG. 1, top electrode 12 comprises a single plate. However, in FIG. 3, it can be seen that top electrode 22 comprises a plurality of electrically connected plates arranged in a tiered configuration. Specifically, top electrode 22 includes a main plate 22a located adjacent the treatment region, which is electrically connected to plates 22b, 22c, 22d, and 22e. Then, plates 22b and 22c are electrically connected to plate 22f, and plates 22d and 22e are electrically connected to plate 22g. Further, plates 22f and 22g are electrically connected to plate 22h, which is electrically connected to the power tube of the generator (or other solid-state supply). As can be seen, in the illustrated embodiment, the treatment region comprises the entire human body such that main plate 22a of top electrode 22 and bottom electrode 24 are positioned proximate to and on either side of the human-body and are sized to extend across the surface area of the human body. Of course, the size of the electrodes will vary depending on the surface area of the treatment region.

As shown in FIG. 3, points A, B, C, D, E, F, G, and H are evenly spaced along the length of main plate 22a, and the power tube of the generator is designated as point O. The size and positioning of the various plates are chosen such that the distances OA, OB, OC, OD, OE, OF, OG, and OH are the same and, thus, points A, B, C, D, E, F, G, and H are each located at the ¼ wavelength position (or, alternatively, ¼ plus a multiple of ½λ). For example, if the selected frequency is 27.12 MHz or 40.68 MHz, each of points A, B, C, D, E, F, G, and H would be located 9.1 feet or 6.15 feet, respectively, from point O. By contrast, as shown in FIG. 1, only point X is located at the ¼ wavelength position.

Figure 4:
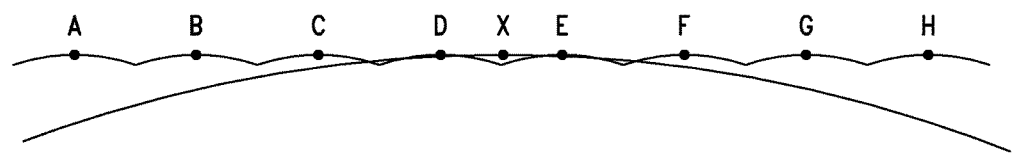
FIG. 4 shows the peak of the signal generated by the apparatus of FIG. 3, wherein eight points (designated as points A-H) are located at the ¼ wavelength position, and wherein the peak of the sinusoid of FIG. 2 is superimposed thereon in order to illustrate the differences between the configurations of the top electrodes of FIGS. 1 and 3.

FIG. 4 shows the peak of the signal generated by the apparatus: of FIG. 3, wherein points A, B, C, D, E, F, G, and H are located at the ¼ wavelength position (or, alternatively, ¼λ plus a multiple of ½λ). The peak of the sinusoid of FIG. 2, along with point X, is superimposed thereon in order to illustrate the differences between the configurations of top electrode 12 (FIG. 1) and top electrode 22 (FIG. 3). As can be seen, point X and points A, B, C, D, E, F, G, and H are each located at the peak of the sinusoid, which corresponds to the highest voltage. In effect, the configuration of top electrode 22 substantially flattens-out the peak of the sinusoid. As such, top electrode 22 may be used to apply more consistent voltages between electrodes 22 and 24 as compared to top electrode 12.

Of course, one skilled in the art will understand that top electrode 22 is merely an example of an electrode that may be used to provide more consistent voltages between the electrodes. Other configurations may also be used in which multiple points (i.e., more or fewer points than the eight points shown in FIG. 3) are located at the ¼ wavelength position (or, alternatively, ¼λ plus a multiple of ¼λ). Stated another way, the top electrode may comprise any configuration of electrically connected plates that are sized and positioned such that each of a plurality of points are located the same distance from the power tube of the generator.

B. Substantially Constant Current

The current of a dielectric field is dependent in part on the dielectric constant of the materials placed between the electrodes, wherein the dielectric constant determines how much current goes through a material for an applied voltage. Specifically, if a material with a low dielectric constant is placed between the electrodes, the current passing through the material will be relatively low. By contrast, if a material with a high dielectric constant is placed between the electrodes, the current passing through the material will be relatively high.

In the case of a human body, the material between the electrodes varies between different regions of the body due to the irregular shape of the body. For example, the chest region may be about 8 inches thick and the shoulder region may be about 4 inches thick. As such, if the human body is placed in apparatus 10 of FIG. 1 or apparatus 20 of FIG. 3 and the electrodes are spaced 8 inches apart, the material between the electrodes in the chest region is the human body (i.e., the 8 inch thickness of the chest region) and the material between the electrodes in the shoulder region is a combination of the human body and air (i.e., the 4 inch thickness of the shoulder region and 4 inches of air). For exemplary purposes, assume that: the dielectric constant of the human body is approximately 71 (the dielectric constant actually varies based on the cell type, as discussed more fully below), which is markedly higher than the dielectric constant of air, which is approximately 1. Because of the differences between the dielectric constants, the current in the chest region will be significantly higher than the current in the shoulder region. As such, the chest region will heat at a significantly faster rate than the shoulder region.

In order to alleviate this problem, any air between a treatment region and the electrodes is preferably displaced with one or more flowable materials having a dielectric constant and dissipation factor that allow a substantially constant current to be applied across the treatment region. As used herein, the term "substantially constant current" means that the difference between the current passing through a portion of a treatment region compared to the current passing through each other portion of the treatment region is preferably less than ±25%, more preferably less than ±20%, more preferably less than ±15%, more preferably less than ±10%, and most preferably less than +5%. The selection of a flowable material is virtually non-limiting and may comprise a liquid, gel, paste, putty, slurry, suspension, or other flowable material. Preferably, each flowable material has a relatively low dissipation factor so that the increase in temperature of the flowable material is minimal at the end of the dielectric heating treatment. A suitable flowable material is distilled water, which has a dielectric constant of 76 and a dissipation factor of 0.005, which is optionally mixed with a suitable additive to modify the overall dielectric constant of the flowable material. Each flowable material preferably has a viscosity that allows the material to conform to the contours of the body. For example, materials having a viscosity of 1, 10, 100, 10,000, 100,000, or even 1,000,000 cps may be used.

As just discussed, in one aspect, a flowable material comprises distilled water mixed with an additive, which is preferably miscible in water. Examples of suitable additives are carboxylic acids, esters, ketones, alcohols, amines, and the like. Preferred additives include, but are not limited to, C1 to C6 branched or straight chain carboxylic acids (e.g., acetic acid), C1 to C6 alcohols and polyols e.g., polyalkylene glycols, methanol, ethanol, n-propanol, isopropanol, butanol, isobutyl ethanol, hexylene glycol), C1 to C6 ketones (e.g., acetone, methyl isobutyl ketone), and C1 to C6 esters (e.g., butyl acetate). As other examples, the additive may comprise a salt, such as magnesium chloride, sodium chloride, or potassium chloride. Exemplary amines are cyclic amines, such as 1,8-Diazabicyclo[5.4.0]undec-7-ene ("DBU"). In general, the additive may comprise any compound in which the dissipation factor is relatively low so that the increase in temperature of the flowable material is minimal at the end of the dielectric heating treatment, and, in which the dielectric constant is chosen to allow a substantially constant current to be applied across the treatment region i.e., a relatively low dielectric constant will decrease the current and a relatively high dielectric constant will increase the current).

The types of apparatuses and methodologies that may be used to apply a dielectric field having a substantially constant current across a treatment region will vary depending on the amount of adipose tissue (referred to herein as "fat"). located within the treatment region in view of the fact that fat heats at a substantially faster rate than other cell types in the body. Examples are provided below for cases in which (1) the treatment region contains a substantially constant amount of fat (Example 1 below) and (2) the treatment region does not contain a substantially constant amount of fat, i.e., different sub-regions contain different amounts of fat (Examples 2 and 3 below). As used herein, the term "substantially constant amount of fat" means that the difference between the amount of fat in a cross-sectional area of a treatment region or sub-region compared to the amount of fat in each other cross-sectional area of the treatment region or sub-region is preferably less than ±5%, more preferably less than ±4%, more preferably less than ±3%, more preferably less than ±2%, and most preferably less than ±1%. It should be understood that a treatment, region or sub-region may contain a substantially constant amount of fat even if the treatment region or sub-region is substantially fat-free. As used herein, the term "substantially fat-free" means that a treatment region or sub-region contains an amount of fat that is preferably less than 15% of the volume of the treatment region or sub-region, more preferably less than 10% of the volume of the treatment region or sub-region, and most preferably less than 5% of the volume of the treatment region or sub-region.

As will be apparent from the description below, the appropriate methodology will depend on the amount of fat located within the treatment region and sub-regions of the body. Of course, one skilled in the art will understand that the apparatuses and methodologies described below are merely examples that can be used to obtain a substantially constant current, across the treatment region, and that other apparatuses and methodologies may be used in accordance with the present invention.

1. Treatment Region Contains a Substantially Constant Amount of Fat
  a. Exemplary Apparatuses
  Referring to FIG. 5, a diagram of an exemplary apparatus that may be used to generate a dielectric field between two electrodes and across a treatment region that contains a substantially constant amount of fat is designated as reference numeral 30. Apparatus 30 includes a top electrode 32 and a bottom electrode 34, both of which are connected to an energy source or generator 36 operable to generate a dielectric field between the electrodes. Preferably, the voltage between top electrode 32 and bottom electrode 34 is substantially constant, which is accomplished by centering the treatment region at a position that is ¼λ or, alternatively, ¼λ plus a multiple of ½λ, from the power tube of generator 36 (as discussed above in connection with FIG. 1) or providing multiple points at this position (as discussed above in connection with FIG. 3). As can be seen, top electrode 32 comprises a plate and bottom electrode 34 has a generally U-shaped configuration so as to define a bath cavity 34a therein.

Figure 5:
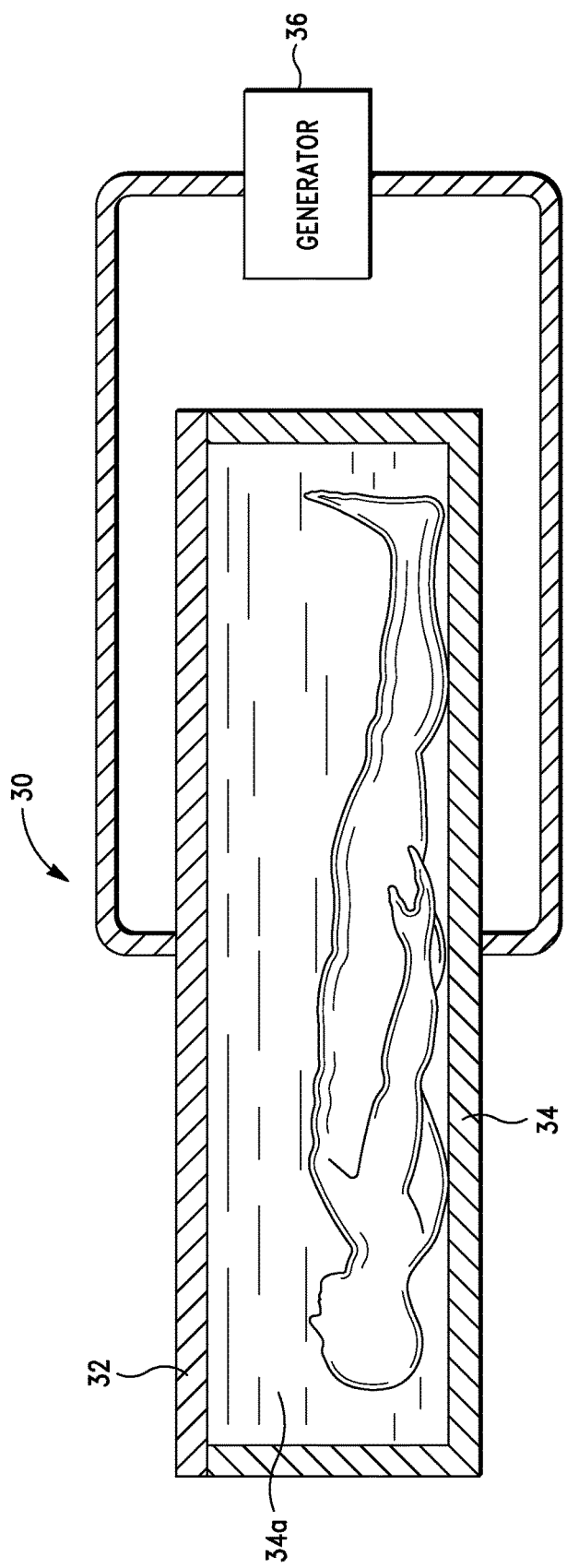
FIG. 5 is a diagram of an exemplary apparatus for generating an alternating electric field between a top electrode and a bottom electrode, wherein the bottom electrode forms a bath cavity that is filled with a flowable material that allows a substantially constant current to be obtained across a treatment region of the subject.

Referring still to FIG. 5, the treatment region in the illustrated embodiment comprises a human body that contains a substantially constant amount of fat. The body is placed within bath cavity 34a, and a flowable material is disposed therein so as to displace the air between the body and electrodes. In accordance with the present invention, the flowable material has a dielectric constant and dissipation factor that allows a substantially constant current to be obtained across the body. Of course, apparatus 30 may be configured such that the head or any other region of the body is positioned outside of bath cavity 34a so as not to form a part of the treatment region. One skilled in the art will appreciate that apparatus 30 may have a variety of different structural configurations that are encompassed by the present invention.

Figure 6A:
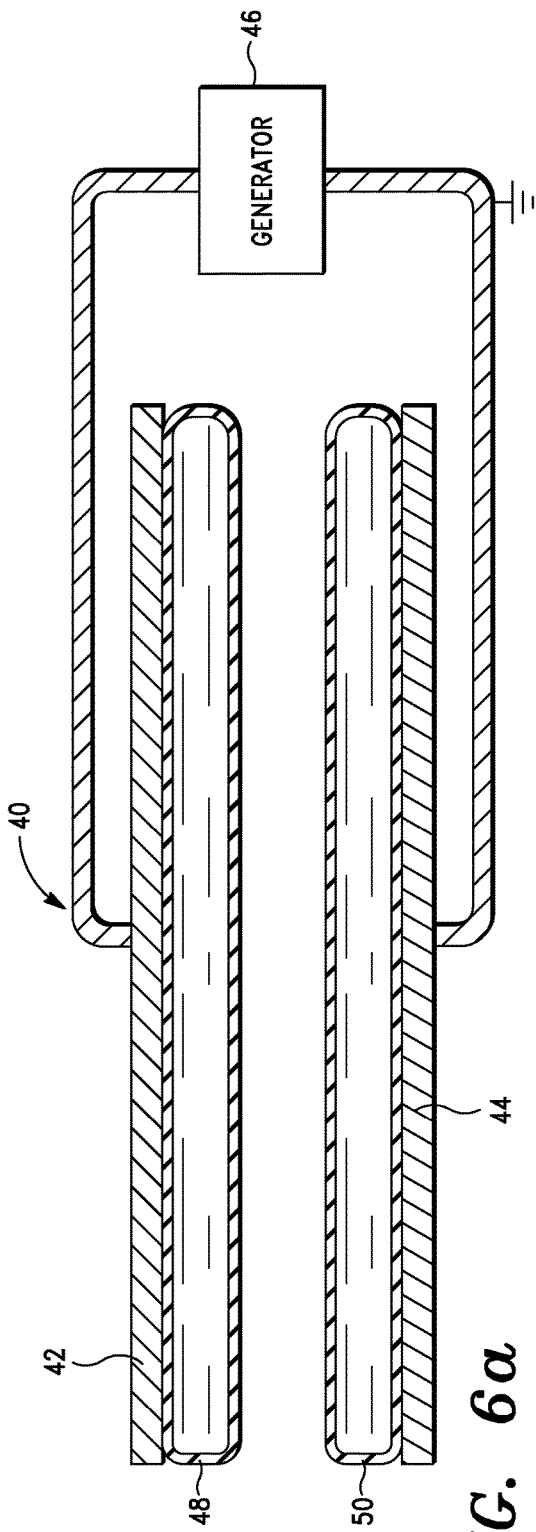
FIG. 6a is a diagram of an exemplary apparatus for generating an alternating electric field between a top electrode and a bottom electrode, wherein a continuous top bladder and a continuous bottom bladder are attached to the top and bottom electrodes, respectively.
Figure 6B:
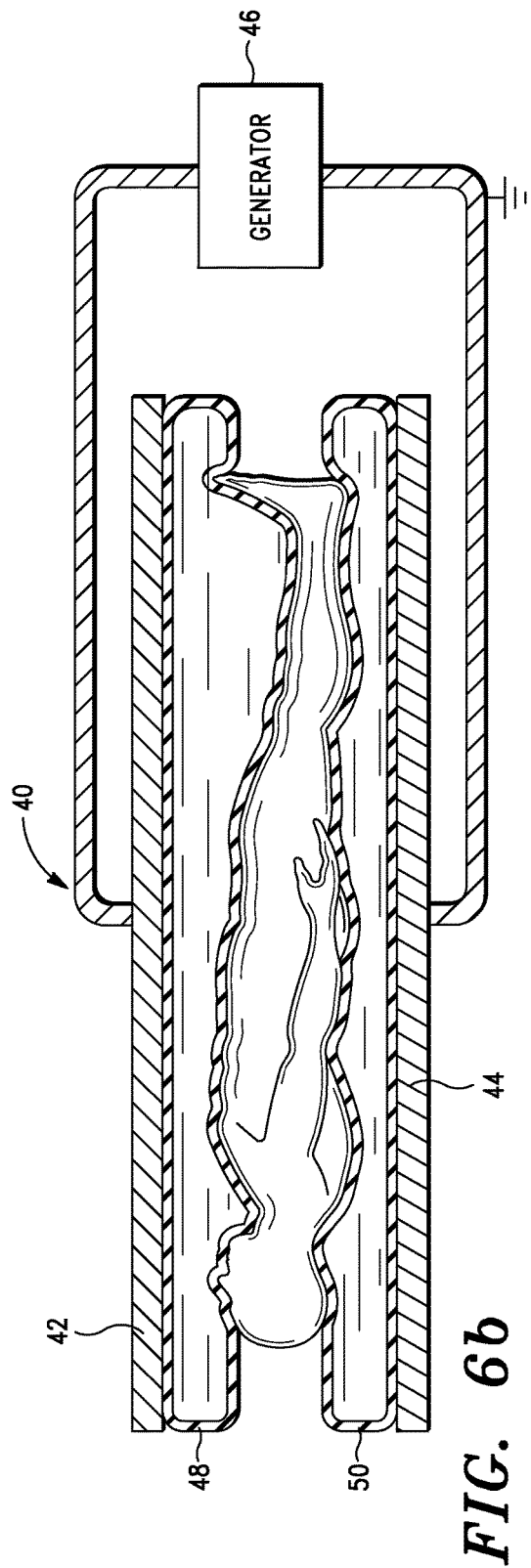
FIG. 6b is a diagram of the apparatus of FIG. 6a, wherein the top and bottom bladders are filled with a flowable material such that the bladders conform to the contours of the subject and allow a substantially constant current to be obtained across the treatment region of the subject.

Referring to FIGS. 6a and 6b, a diagram of an exemplary apparatus that may be used to generate a dielectric field between two electrodes and across a treatment region that contains a substantially constant amount of fat is, designated as reference numeral 40. Apparatus includes a top electrode 42 and a bottom electrode 44, both of which are connected to an energy source or generator 46 operable to generate a dielectric field between the electrodes. Preferably, the voltage between top electrode 42 and bottom electrode 44 is substantially constant, which is accomplished by centering the treatment region at a position that is ¼λ or, alternatively, ¼λ plus a multiple of ¼λ, from the power tube of generator 46 (as discussed above in connection with FIG. 1) or providing multiple points at this position (as discussed above in connection with FIG. 3). As can be seen, top electrode 42 and bottom electrode 44 each comprise a plate, and disposed between the electrodes is a top bladder 48 (attached to top electrode 42) and a bottom bladder 50 (attached to bottom electrode 44). Top and bottom bladders 48, 50 may be made of any flexible and stretchable material, such as silicone rubber or liquid silicone rubber sold by Rhodia Silicones, so that the bladders are able to stretch when filled with a flowable material. Top and bottom bladders 48, 50 are continuous in the sense that a single top bladder extends across the surface area of top electrode 42 and a single bottom bladder extends across the surface area of bottom electrode 44 so as to define a cavity therebetween.

As shown in FIG. 6b, the treatment region in the illustrated embodiment comprises a human body that contains a substantially constant amount of fat. The body is placed within the cavity between top and bottom bladders 48, 50, and a flowable material is injected into each of top and bottom bladders 48, 50 so as to displace the air between the body and electrodes. As such, the top of the body is in contact with top bladder 48 and the bottom of the body is in contact with bottom bladder 50. In accordance with the present invention, the flowable material injected into top and bottom bladders 48, 50 has a dielectric constant and dissipation factor that allows a substantially constant current to be obtained across the body. Preferably, the same flowable material is injected into top and bottom bladders 48, 50, although the use of different flowable materials is also contemplated. One skilled in the art will appreciate that apparatus 40 may have a variety of different structural configurations that are encompassed by the present invention. It should also be understood that the treatment region need not comprise the entire human body, and that only a portion of a body may be positioned between the electrodes of apparatus 40.

b. General Methodology I

For cases in which a treatment region of a body contains a substantially constant amount of fat, the treatment region is placed in apparatus 30 shown in FIG. 5, and a flowable material is disposed within bath cavity 34a so as to displace the air between the treatment region and electrodes. Alternatively, the treatment region is placed in apparatus 40 shown in FIG. 6a, and a flowable material is injected into top bladder 48 and bottom bladder 50. In either case, the composition of the flowable material is chosen so as to obtain a substantially, constant current across the treatment region so that the same cell type in different sub-regions of the treatment region heats at substantially the same rate. This is accomplished by utilizing a flowable material that "simulates the body," as discussed below.

In one aspect, the flowable material simulates the body if it has a dissipation factor and dielectric constant that are substantially the same as the body. For example, if the body is a human body and the dielectric field has a frequency of 40 MHz, the flowable material preferably has a dissipation factor of about 1.8 and a dielectric constant of about 71 (i.e., the dissipation factor and dielectric constant of many cell types in the human body). In this case, the current passing through the treatment region is the same regardless of the different thickness sections of the treatment region. Because the flowable material will heat at substantially the same rate as the treatment region, it is preferable to chill the flowable material prior to, during and/or after the dielectric heating treatment so as to provide a cooling effect on the skin of the body.

In another aspect, the flowable material has a dissipation factor and dielectric constant that are different than those of the body; however, the relationship between the dissipation factor and dielectric constant are such that the flowable material simulates the body. Preferably, the flowable material has a lower dissipation factor than the body so that the flowable material heats at a slower rate than the body. As such, the flowable material has a dissipation factor that is preferably less than 1.0, more preferably less than 0.5, and most preferably less than 0.3. In this case, the required values of the dissipation factor and dielectric constant of the flowable material are calculated so as to obtain a substantially constant current across the treatment region and, then, such values are used to determine the composition of the flowable material. For example, it will be seen in Example 1 below that an acceptable flowable material is comprised of a mixture of 83.42% distilled water and 16.58% acetic acid, which has a dissipation factor of 0.02003 and a dielectric constant of 26.5. With this flowable material, there is a minor difference between the current passing through the different thickness sections of the treatment region. However, the current difference is small and nonetheless results in the application of a substantially constant current across the treatment region.

Example 1

An example using this general methodology is provided below in which a human body is placed in apparatus 40 shown in FIG. 6a, wherein the treatment region includes the chest and shoulder regions of the body. The chest region has a thickness of 8 inches and the shoulder region has a thickness of 4 inches. In this example, it is assumed that the chest and shoulder regions of the body are substantially fat-free. The top and bottom electrodes 42 and 44 are spaced 8 inches apart, and the voltage between the electrodes is 1,000 volts. A flowable material comprising distilled water mixed with acetic acid (in volumes to be calculated below) is injected into top bladder 48 and bottom bladder 50. Accordingly, the material between the electrodes in the chest region is the human body (i.e., the 8 inch chest region abuts against both electrodes) and the material between the electrodes in the shoulder region is the human body and the distilled water/acetic acid mixture (i.e., the 4 inch shoulder region and 4 inches of the distilled water/acetic acid mixture).

The following table identifies the dielectric constant, dissipation factor, specific heat and density of each of the materials between the electrodes, assuming that the frequency of the dielectric field is 40 MHz:

|  | Dielectric Constant | Dissipation Factor | Specific Heat (J/g ° C.) | Density (g/cm$^3$) |
| --- | --- | --- | --- | --- |
| Human Body (Chest and Shoulder Regions) | 71 | 1.8 | 3.47 | 1.027 |
| Distilled Water | 76 | 0.005 | 4.18 | 1 |
| Acetic Acid | 6.20 | 0.0262 | 2.18 | 1.05 |

In order to obtain a substantially constant current across the chest and shoulder regions of the body so that the same cell type in both regions heats at substantially the same rate, the current passing through the shoulder region and surrounding distilled water/acetic acid mixture must be substantially the same as the current passing through the chest region. The following calculations are performed to determine the volume of distilled water and the volume of acetic acid that will result in a substantially constant current across the chest and shoulder regions of the body. In the following equations, the subscript 1 denotes the chest region of the body, the subscript 2 denotes the shoulder region of the body, and the subscript 3 denotes the distilled water/acetic acid mixture (wherein the subscript dw denotes the distilled water and the subscript aa denotes the acetic acid in certain equations).

Calculations for Chest Region

The capacitance of the chest region is expressed by the following equation:

$$C_1 = \frac{\varepsilon_1 \times \varepsilon_0 \times A}{d_1} \tag{5}$$

where
  $C_1$=capacitance of chest region in farads
  $\varepsilon_1$=dielectric constant of chest region
  $\varepsilon_0$=electric constant (8.854×10$^{-12}$ farad/meter)
  A=area of chest region in meters$^2$
  $d_1$=thickness of chest region in meters.

Equation (5) may be simplified and rewritten so that the thickness of the chest region is expressed in inches (noting that 1 meter=39.37 inches), as follows:

$$C_1 = \frac{\varepsilon_1 \times A \times 0.2249}{d_1} \quad (6)$$

where
$C_1$=capacitance of chest region in picofarads
$\varepsilon_1$=dielectric constant of chest region
A=area of chest region in inches$^2$
$d_1$=thickness of chest region in inches.

It should be noted that equation (6) (rather than equation (5)) will be used throughout the specification to refer to the capacitance of a treatment region, sub-region or other material.

Assuming that the dielectric constant of the chest region is 71 and that the unit area is 1 inch$^2$, the capacitance of the chest region is:

$$C_1 = \frac{71 \times 1 \times 0.2249}{8} = 1.9932 \text{ pF} \quad (7)$$

The capacitive reactance of the chest region is given by the following equation:

$$X_{C1} = \frac{1}{2 \times \pi \times f \times C_1} \quad (8)$$

where
$X_{C1}$=capacitive reactance of chest region in ohms
f=frequency of dielectric field in hertz
$C_1$=capacitance of chest region in farads.

Using the capacitance of the chest region derived above and assuming that the frequency of the dielectric field is 40 MHz, the capacitive reactance of the chest region is:

$$X_{C1} = \frac{1}{2 \times \pi \times 40 \times 10^6 \times 1.9932 \times 10^{-12}} = 1,996.2 \text{ ohms} \quad (9)$$

The resistance of the chest region is equal to the product of the dissipation factor of the chest region and the capacitive reactance of the chest region, as follows:

$$R_1 = df_1 \times X_{C1} \quad (10)$$

where
$R_1$=resistance of chest region in ohms
$df_1$=dissipation factor of chest region
$X_{c1}$=capacitive reactance of chest region in ohms.

Using the capacitive reactance of the chest region derived above and assuming that the dissipation factor of the chest region is 1.8, the resistance of the chest region is expressed as follows:

$$R_1 = 1.8 \times 1,996.2 = 3,593.2 \text{ ohms} \quad (11)$$

Next, the current passing between the electrodes through the chest region is represented by the following equation:

$$I = \frac{V}{\sqrt{X_{C1}^2 + R_1^2}} \quad (12)$$

where
I=current in amperes.
V=voltage between the electrodes in volts.
$X_{C1}$=capacitive reactance of chest region in ohms
$R_1$=resistance of chest region in ohms.

Using the capacitive reactance and resistance of the chest region-derived above and assuming that the voltage between the electrodes is 1,000 volts, the current passing between the electrodes through the chest region is:

$$I = \frac{1,000}{\sqrt{1,996.2^2 + 3,593.2^2}} = 0.24328 \text{ amps} \quad (13)$$

The power that is dissipated in the chest region due to the application of the dielectric field (over an area of 1 inch$^2$) is expressed by the following equation:

$$P_1 = R_1 \times I^2 \quad (14)$$

where
$P_1$=power in chest region in watts due to the dielectric field (over an area of 1 inch$^2$)
$R_1$=resistance of chest region in ohms
I=current in amperes.

Using the resistance of the chest region and the current derived above; the power dissipated in the chest region due to the dielectric field (over an area of 1 inch$^2$) is:

$$P_1 = 3,593.2 \times (0.24328)^2 = 212267 \text{ watts} \quad (15)$$

The increase in temperature of the chest region during the application of the dielectric field is represented by the following equation:

$$\Delta T_1 = \frac{P_1 \times t_1}{h_1 \times \rho_1 \times d_1} \quad (16)$$

where
$\Delta T_1$=increase in temperature of chest region in ° C.
$P_1$=power in chest region in watts due to the dielectric field (over an area of 1 inch$^2$)
$t_1$=heating time of chest region in seconds
$h_1$=specific heat of chest region in J/g ° C.
$\rho_1$=density of chest region in g/inches$^3$
$d_1$=thickness of chest region in inches.

Equation (16) may be rewritten so that the density of the chest region is expressed in g/cm$^3$ (noting that 1 inch=2.54 cm), as follows:

$$\Delta T_1 = \frac{P_1 \times t_1}{16.387 \times h_1 \times \rho_1 \times d_1} \quad (17)$$

where
$\Delta T_1$=increase in temperature of chest region in ° C.
$P_1$=power in chest region in watts due to the dielectric-field (over an area of 1 inch$^2$)
$t_1$=heating time of chest region in seconds
$h_1$=specific heat of chest region in J/g ° C.
$\rho_1$=density of chest region in g/cm$^3$
$d_1$=thickness of chest region in inches.

It should be noted that equation (17) (rather than equation (16)) will be used throughout the specification to refer to the increase in temperature of a treatment region, sub-region or other material.

Using the power in the chest region derived above and assuming that the specific heat and density of the chest region are 3.47 J/g ° C. and 1.027 g/cm³, respectively, the increase in temperature of the chest region during the application of the dielectric field is expressed as follows:

$$\Delta T_1 = \frac{212.67 \times t_1}{16.387 \times 3.47 \times 1.027 \times 8} = 0.4552 \times t_1 \text{ ° C.} \quad (18)$$

Calculations for Shoulder Region and Distilled Water/Acetic Acid Mixture

The capacitance of the shoulder region is expressed by the following equation:

$$C_2 = \frac{\varepsilon_2 \times A \times 0.2249}{d_2} \quad (19)$$

where
$C_2$=capacitance of shoulder region in picofarads
$C_2$=dielectric constant of shoulder region
A=area of shoulder region in inches²
$d_2$=thickness of shoulder region in inches.

Assuming that the dielectric constant of the shoulder region is 71 and that the unit area is 1 inch², the capacitance of the shoulder region is:

$$C_2 = \frac{71 \times 1 \times 0.2249}{4} = 3.9864 \text{ pF} \quad (20)$$

The capacitive reactance of the shoulder region is then given by the following equation:

$$X_{C2} = \frac{1}{2 \times \pi \times f \times C_2} \quad (21)$$

where
$X_{C2}$=capacitive reactance of shoulder region in ohms
f=frequency of dielectric field in hertz
$C_2$=capacitance of shoulder region in farads.

Using the capacitance of the shoulder region derived above and assuming that the frequency of the dielectric field is 40 MHz, the capacitive reactance of the shoulder region is:

$$X_{C2} = \frac{1}{2 \times \pi \times 40 \times 10^6 \times 3.9864 \times 10^{-12}} = 998.112 \text{ ohms} \quad (22)$$

The resistance of the shoulder region is equal to the product of the dissipation factor of the shoulder region and the capacitive reactance of the shoulder region, as follows:

$$R_2 = df_2 \times X_{C2} \quad (23)$$

where
$R_2$=resistance of shoulder region in ohms
$df_2$=dissipation factor of shoulder region
$X_{C2}$=capacitive reactance of shoulder region in ohms.

Using the capacitive reactance of the shoulder region derived above and assuming that the dissipation factor of the shoulder region is 1.8, the resistance of the shoulder region is expressed as follows:

$$R_2 = 1.8 \times 998.112 = 1,796.6 \text{ ohms} \quad (24)$$

The increase in temperature of the shoulder region during the application of the dielectric field is represented by the following equation:

$$\Delta T_2 = \frac{P_2 \times t_2}{16.387 \times h_2 \times \rho_2 \times d_2} \quad (25)$$

where
$\Delta T_2$=increase in temperature of shoulder region in ° C.
$P_2$=power in shoulder region in watts due to the dielectric field
$t_2$=heating time of shoulder region in seconds
$h_2$=specific heat of shoulder region in J/g ° C.
$\rho_2$=density of shoulder region in g/cm³
$d_2$=thickness of shoulder region in inches.

Assuming that the specific heat and density of the shoulder region are 3.47 J/g ° C. and 1.027 g/cm³, respectively, the increase in temperature of the shoulder region during the application of the dielectric field is expressed as follows:

$$\Delta T_2 = \frac{P_2 \times t_2}{16.387 \times 3.47 \times 1.027 \times 4} = 0.00428 \times P_2 \times t_2 \text{ ° C.} \quad (26)$$

In order for the shoulder region to heat at the same rate as the chest region, the increase in temperature of the shoulder region ($\Delta T_2$) must be equal to the increase in temperature of the chest region ($\Delta T_1$), and, the heating time of the shoulder region ($t_2$) must be equal to the heating time of the chest region ($t_1$). In this case, equations (18) and (26) may be combined and simplified as follows:

$$P_2 = \frac{0.4552}{0.00428} = 106.335 \text{ watts.} \quad (27)$$

The power that is dissipated in the shoulder region due to the application of the dielectric field is expressed by the following equation:

$$P_2 = R_2 \times I^2 \quad (28)$$

where
$P_2$=power in shoulder region in watts due to the dielectric field
$R_2$=resistance of shoulder region in ohms
I=current in amperes.

Using the power dissipated in the shoulder region and the resistance of the shoulder region derived above, the power dissipated in the shoulder region due to the dielectric field is expressed as:

$$106.335 = 1,796.6 \times I^2 \quad (29)$$

By solving equation (29) for I, it can be seen that the current passing between the electrodes through the shoulder region is:

$$I = \sqrt{\frac{106.335}{1,796.6}} = 0.24328 \text{ amps} \quad (30)$$

Thus, the current passing between the electrodes through the shoulder region (see equation (30)) is equal to the current passing between the electrodes through the chest region (see equation (13)).

Now, the capacitance of the distilled water/acetic acid mixture adjacent the shoulder region is expressed by the following equation:

$$C_3 = \frac{\varepsilon_3 \times A \times 0.2249}{d_3} \quad (31)$$

where
$C_3$=capacitance of mixture in picofarads.
$\varepsilon_3$=dielectric constant of mixture
A=area of mixture in inches$^2$
$d_3$=thickness of mixture in inches.

For a unit area of 1 inch$^2$, the capacitance of the distilled, water/acetic acid mixture is:

$$C_3 = \frac{\varepsilon_3 \times 1 \times 0.2249}{4} = \varepsilon_3 \times 0.05617 \text{ pF.} \quad (32)$$

The capacitive reactance of the distilled water/acetic acid mixture is then given by the following equation:

$$X_{C3} = \frac{1}{2 \times \pi \times f \times C_3} \quad (33)$$

where
$X_{C3}$=capacitive reactance of mixture in ohms
f=frequency of dielectric field in hertz
$C_3$=capacitance of mixture in farads.

Using the capacitance of the distilled water/acetic acid mixture derived above and assuming that the frequency of the dielectric field is 40 MHz, the capacitive reactance of the distilled water/acetic acid mixture is:

$$X_{C3} = \frac{1}{2 \times \pi \times 40 \times 10^6 \times \varepsilon_3 \times 0.05617 \times 10^{-12}} \quad (34)$$

$$= \frac{70,836}{\varepsilon_3} \text{ ohms}$$

The resistance of the distilled water/acetic acid mixture is equal to the product of the dissipation factor of the distilled water/acetic acid mixture and the capacitive reactance of the distilled water/acetic acid mixture, as follows:

$$R_3 = df_3 \times X_{C3} \quad (35)$$

where
$R_3$=resistance of mixture in ohms
$df_3$=dissipation factor of mixture
$X_{C3}$=capacitive reactance of mixture in ohms.

Using the capacitive reactance of the distilled water/acetic acid mixture derived above, the resistance of the distilled water/acetic acid mixture is:

$$R_3 = df_3 \times \frac{70,836}{\varepsilon_3} \text{ ohms} \quad (36)$$

Next, the current passing between the electrodes through the distilled water/acetic acid mixture and shoulder region is represented by the following equation:

$$I = \frac{V}{\sqrt{(X_{C2} + X_{C3})^2 + (R_2 + R_3)^2}} \quad (37)$$

where
I=current in amperes
V=voltage between the electrodes in volts
$X_{C2}$=capacitive reactance of shoulder region in ohms.
$X_{C3}$=capacitive reactance of mixture in ohms
$R_2$=resistance of shoulder region in ohms
$R_3$=resistance of mixture in ohms.

Using the current passing between the electrodes through the shoulder region derived above (which is the same as the current passing through the distilled water/acetic acid mixture and shoulder region), using the capacitive reactance and resistance of each of the shoulder region and distilled water/acetic acid, mixture derived above, and assuming that the voltage between the electrodes is 1,000 volts, the current passing between the electrodes through the distilled water/acetic acid mixture and shoulder region is:

$$0.24328 = \frac{1,000}{\sqrt{\left(998.112 + \frac{70,836}{\varepsilon_3}\right)^2 + \left(1,796.6 + \frac{df_3 \times 70,836}{\varepsilon_3}\right)^2}} \text{ amps} \quad (38)$$

Now, assume that the distilled water/acetic acid mixture consists of a volume of distilled water represented by x and a volume of acetic acid represented by 1−x. It is desired to find the value of x such that the dielectric constant of the distilled water/acetic acid mixture ($\varepsilon_3$) and the dissipation factor of the distilled water/acetic acid mixture ($df_3$) satisfy equation (38).

The capacitance of the distilled water is expressed by the following equation:

$$C_{dw} = \frac{\varepsilon_{dw} \times A \times 0.2249}{d_{dw}} \quad (39)$$

where
$C_{dw}$=capacitance of distilled water in picofarads
$\varepsilon_{dw}$=dielectric constant of distilled water
A=area of distilled water in inches$^2$
$d_{dw}$=thickness of distilled water in inches.

For a unit area of 1 inch$^2$, the capacitance of the distilled water is:

$$C_{dw} = \frac{76 \times 1 \times 0.2249}{4x} = \frac{4.267}{x} \text{ pF} \quad (40)$$

Similarly, the capacitance of the acetic acid is expressed by the following equation:

$$C_{aa} = \frac{\varepsilon_{aa} \times A \times 0.2249}{d_{aa}} \quad (41)$$

where
$C_{aa}$=capacitance of acetic acid in picofarads
$E_{aa}$=dielectric constant of acetic acid
A=area of acetic acid in inches$^2$
$d_{aa}$=thickness of acetic acid in inches.

For a unit area of 1 inch$^2$, the capacitance of the acetic acid is:

$$C_{aa} = \frac{6.2 \times 1 \times 0.224}{4(1-x)} = \frac{0.3481}{1-x} \text{ pF} \quad (42)$$

The capacitive reactance of the distilled water is then given by the following equation:

$$X_{Cdw} = \frac{1}{2 \times \pi \times f \times C_{dw}} \quad (43)$$

where
$X_{Cdw}$=capacitive reactance of distilled water in ohms
f=frequency of dielectric field in hertz
$C_{dw}$=capacitance of distilled water in farads.

Using the capacitance of the distilled water derived above and assuming that the frequency of the dielectric field is 40 MHz, the capacitive reactance of the distilled water is:

$$X_{Cdw} = \frac{x}{2 \times \pi \times 40 \times 10^6 \times 4.267 \times 10^{-12}} = 932.47x \text{ ohms} \quad (44)$$

Similarly, the capacitive reactance of the acetic acid is given by the following equation:

$$X_{Caa} = \frac{1}{2 \times \pi \times f \times C_{aa}} \quad (45)$$

where
$X_{Caa}$=capacitive reactance of acetic acid in ohms
f=frequency of dielectric field in hertz
$C_{aa}$=capacitance of acetic acid in farads.

Using the capacitance of the acetic acid derived above and assuming that the frequency of the dielectric field is 40 MHz, the capacitive reactance of the acetic acid is:

$$X_{Caa} = \frac{1-x}{2 \times \pi \times 40 \times 10^6 \times 0.3481 \times 10^{-12}} \quad (46)$$
$$= 11,430.26(1-x) \text{ ohms}$$

Now, the total capacitive reactance of the distilled water/acetic acid mixture is expressed as follows:

$$X_{C3} = X_{Cdw} + X_{Caa} \quad (47)$$

where
$X_{C3}$=capacitive reactance of mixture in ohms
$X_{Cdw}$=capacitive reactance of distilled water in ohms
$X_{Caa}$=capacitive reactance of acetic acid in ohms.

Using the capacitive reactance of each of the distilled water and acetic acid derived above, the capacitive reactance of the distilled water/acetic acid mixture is:

$$X_{C3} = (932.47x) + (11,430.26(1-x)) = 11,430.26 - 10,497.8x \text{ ohms} \quad (48)$$

The resistance of the distilled water is equal to the product of the dissipation factor of the distilled water and the capacitive reactance of the distilled water, as follows:

$$R_{dw} = df_{dw} \times X_{Cdw} \quad (49)$$

where
$R_{dw}$=resistance of distilled water in ohms
$df_{dw}$=dissipation factor of distilled water
$X_{Cdw}$=capacitive reactance of distilled water in ohms.

Using the capacitive reactance of the distilled water derived above and assuming that the dissipation factor of distilled water is 0.005, the resistance of the distilled water is:

$$R_{dw} = 0.005 \times 932.47x = 4.66x \text{ ohms} \quad (50)$$

Similarly, the resistance of the acetic acid is equal to the product of the dissipation factor of the acetic acid and the capacitive reactance of the acetic acid, as follows:

$$R_{aa} = df_{aa} \times X_{Caa} \quad (51)$$

where:
$R_{aa}$=resistance of acetic acid in ohms
$df_{aa}$=dissipation factor of acetic acid
$X_{Caa}$=capacitive reactance of acetic acid in ohms.

Using the capacitive reactance of the acetic acid derived above and assuming that the dissipation factor of acetic acid is 0.0262, the resistance of the acetic acid is:

$$R_{aa} = 0.0262 \times 11,430.26(1-x) = 299.47(1-x) \text{ ohms} \quad (52)$$

Now, the total resistance of the distilled water/acetic acid mixture is expressed as follows:

$$R_3 = R_{dw} + R_{aa} \quad (53)$$

where
$R_3$=resistance of mixture in ohms
$R_{dw}$=resistance of distilled water in ohms
$R_{aa}$=resistance of acetic acid in ohms.

Using the resistance of each of the distilled water and acetic acid derived above, the resistance of the distilled water/acetic acid mixture is:

$$R_3 = (4.66x) + (299.47(1-x)) = 299.47 - 294.8x \text{ ohms} \quad (54)$$

Next, the current passing between the electrodes through the distilled water/acetic acid mixture and shoulder region may be represented by the following equation:

$$I = \frac{V}{\sqrt{(X_{C2} + X_{C3})^2 + (R_2 + R_3)^2}} \quad (55)$$

where
I=current in amperes
V=voltage between the electrodes in volts
$X_{C2}$=capacitive reactance of shoulder region in ohms
$X_{C3}$=capacitive reactance of mixture in ohms
$R_2$=resistance of shoulder region in ohms
$R_3$=resistance of mixture in ohms.

Using the current passing between the electrodes through the distilled water/acetic acid mixture and shoulder region derived above, using the capacitive reactance and resistance of the distilled water/acetic acid mixture derived above, and assuming that the voltage between the electrodes is 1,000 volts, the current passing between the electrodes through the distilled water/acetic acid mixture, and shoulder region is:

$$0.24328 = \frac{1,000}{\sqrt{(12,428.372 - 10,497.79x)^2 + (2,096.07 - 294.81x)^2}} \text{ amps} \quad (56)$$

By solving equation (56) for x, it can be seen that the volume of distilled water represented by x is 0.8342 and, thus, the volume of acetic acid represented by (1-x) is 0.1658. In other words, the distilled water/acetic acid mixture is 83.42% distilled water (by volume) and 16.58% acetic acid (by volume).

By combining equations (34) and (48) (with x=0.8342), the capacitive reactance of the distilled water/acetic acid mixture is:

$$X_{C3} = \frac{70,836}{\varepsilon_3} \quad (57)$$
$$= 11,430.26 - (10,497.8 \times 0.8342) \text{ ohms}$$

By solving equation (57) for $\varepsilon_3$, it can be seen that the dielectric constant of the distilled water/acetic acid mixture is 26.5.

The dissipation factor of the distilled water/acetic acid mixture is equal to the resistance of the distilled water/acetic acid mixture divided by the capacitive reactance of the distilled water/acetic acid mixture, as follows:

$$df_3 = \frac{R_3}{X_{C3}} \quad (58)$$

where
$df_3$=dissipation factor of mixture
$R_3$=resistance of mixture in ohms
$X_{C3}$=capacitive reactance of mixture in ohms.

Using the resistance and capacitive reactance of the distilled water/acetic acid mixture derived above (with x=0.8342), the dissipation factor of the distilled water/acetic acid mixture is:

$$df_3 = \frac{299.47 - (294.81 \times 0.8342)}{2,673} = 0.02003 \quad (59)$$

The power that is dissipated in the distilled water/acetic acid mixture due to the application of the dielectric field is expressed by the following equation:

$$P3 = R_3 \times I^2 \quad (60)$$

where
$P_3$=power in mixture in watts due to the dielectric field
$R_3$=resistance of mixture in ohms
I=current in amperes.

Using the resistance of the distilled water/acetic acid mixture and the current derived above, the power dissipated in the distilled water/acetic acid mixture due to the dielectric field is:

$$P_3 = (299.47 - (29481 \times 0.8342)) \times (0.24328)^2 = 3.166 \text{ watts} \quad (61)$$

It can be appreciated that the power dissipated in the distilled water/acetic acid mixture due to the dielectric field i.e., 3.166 watts) is relatively small in comparison to the power dissipated in the chest region (i.e., 212.67 watts) and the shoulder region (i.e., 106:335 watts). Thus, in this example, the power "lost" due to the distilled water/acetic acid mixture is less than 1% of the total power.

The increase in temperature of the distilled water/acetic acid mixture during the application of the dielectric field is represented by the following equation:

$$\Delta T_3 = \frac{P_3 \times t_3}{16.387(h_3 \times \rho_3 \times d_3)} \quad (62)$$

where
$\Delta T_3$=increase in temperature of mixture in ° C.
$P_3$ power in mixture in watts due to the dielectric field
$t_3$=heating time of mixture in seconds
$h_3$=specific heat of mixture in J/g ° C.
$\rho_3$=density of mixture in g/cm$^3$
$d_3$=thickness of mixture in inches.

Using the power in the distilled water/acetic acid mixture derived above and assuming that the specific heat of the distilled water/acetic acid mixture is 3.85 (i.e., (4.18× 0.8342)+(2.18×0.1658)) and that the density of the distilled water/acetic acid mixture is 1.008 (i.e., (1.0×0.8342)+(1.05× 0.1658)), the increase in temperature of the distilled water/acetic acid mixture during the application of the dielectric field is expressed as follows:

$$\Delta T_3 = \frac{3.166 \times t_3}{16.387(3.85 \times 1.008 \times 4)} = 0.01249 \times t_3 \text{ ° C.} \quad (63)$$

Exemplary Change in Temperature after 7 Seconds

As set forth above, the increase in temperature of the chest region, shoulder region and distilled water/acetic acid mixture during the application of the dielectric field are expressed as follows:

$$\Delta T_1 = 0.4552 \times t_1 \text{° C.} \quad (64)$$

$$\Delta T_2 = 0.4552 \times t_2 \text{° C.} \quad (65)$$

$$\Delta T_3 = 0.01249 \times t_3 \text{° C.} \quad (66)$$

If, for example, the heating time is 7 seconds (i.e., the human body is exposed to the dielectric field for 7 seconds), the increase in temperature of the chest and shoulder regions is 3.18° C. (or 5.73° F.) and the increase in temperature of the distilled water/acetic acid mixture is 0.0874° C. (or 0.157° F.). Thus, if the human body starts at 98.6° F. (i.e., body temperature) and the distilled water/acetic acid mixture starts at 77° F., then the temperatures of the chest and shoulder regions and the distilled water/acetic acid mixture are 104.33° F. and 77.157° F., respectively, at the end of the dielectric heating treatment.

In this example, it can be seen that the chest and shoulder regions heat at the same rate. It can also be seen that the temperature of the distilled water/acetic acid mixture is relatively low at the end of the dielectric heating treatment (i.e., 77.157° F.). Accordingly, the distilled water/acetic acid mixture does not heat the skin of the human body during the dielectric heating treatment and also serves to cool the body upon completion of the dielectric heating treatment. Further, the distilled water/acetic acid mixture may be chilled prior to, during and/or after the dielectric heating treatment so as to provide an even greater cooling effect on the human body.

Other Sub-Regions of the Treatment Region

In this case, the current passing through the chest and shoulder regions is the same, i.e., 0.24328 amps. It should be understood that there will be a minor difference between this current and the current passing through other sub-regions of the treatment, regions if those other sub-regions have different thicknesses. For example, using the above equations, it can be calculated that the current passing through a sub-region with a thickness of 6 inches is 0.2544 amps (an increase of 4.57%) and the current passing through a sub-region with a thickness of 2 inches is 0.217 amps (a decrease of 10.8%). These differences are minor and nonetheless result in the application of a substantially constant current across the treatment region. Of course, one skilled in the art will understand that if the current differences are substantial (e.g., if a sub-region is unusually thick), it is possible to apply the above methodology separately to the various sub-regions.

Distilled Water/Acetic Acid Mixture Vs. Air

In the above example, the distilled water/acetic acid mixture injected into the bladders in order to obtain a substantially constant current across the chest and shoulder regions so that the same cell type in both regions heats at substantially the same rate. In order to illustrate the benefits of the distilled water/acetic acid mixture, calculations, similar to those above are performed for a case in which the shoulder region is surrounded by air. It is assumed that air has a dielectric constant of 1 and a dissipation factor of 0. In the following equations, the subscript 2 denotes the shoulder region and the subscript 3' denotes the air surrounding the shoulder region. It should be understood that all of the calculations for the chest region are the same as those in Example 1. It should also be understood that equations (20), (22) and (24) above will not change and, as such, the values of the capacitance, capacitive reactance and resistance of the shoulder region are 3.9864 pF, 998.112 ohms and 1,796.6 ohms, respectively.

The capacitance of the air is expressed by the following equation:

$$C_{3'} = \frac{\varepsilon_{3'} \times A \times 0.2249}{d_{3'}} \quad (67)$$

where
$C_{3'}$=capacitance of air in picofarads
$\varepsilon_{3'}$=dielectric constant of air
A=area of air in inches$^2$
$d_{3'}$=thickness of air in inches.

Assuming that the dielectric constant of air is 1 and that the unit area is 1 inch$^2$, the capacitance of the air is:

$$C_{3'} = \frac{1 \times 1 \times 0.2249}{4} = 0.056 \text{ pF} \quad (68)$$

The capacitive reactance of the air is then given by the following equation:

$$X_{C_{3'}} = \frac{1}{2 \times \pi \times f \times C_{3'}} \quad (69)$$

where
$X_{C_{3'}}$=capacitive reactance of air in ohms
f=frequency of dielectric field in hertz
C3'=capacitance of air in farads.

Using the capacitance of the air derived above and assuming that the frequency of the dielectric field is 40 MHz, the capacitive reactance of the air is:

$$X_{C_{3'}} = \frac{1}{2 \times \pi \times 40 \times 10^6 \times 0.056 \times 10^{-12}} = 70{,}861.5 \text{ ohms} \quad (70)$$

The resistance of the air is equal to the product of the dissipation factor of the air and the capacitive reactance of the air, as follows:

$$R_{3'} = df_{3'} \times X_{C_{3'}} \quad (71)$$

where
$R_{3'}$=resistance of air in ohms
$df_{3'}$=dissipation factor of air
$X_{C_{3'}}$=capacitive reactance of air in ohms.

Using the capacitive reactance of the air derived above and assuming that the dissipation factor of air is 0, the resistance of the air is expressed as follows:

$$R_{3'} = 0 \times 70{,}861.5 = 0 \text{ ohms} \quad (72)$$

Next, the current passing between the electrodes through the air (as well as through the shoulder region) is represented by the following equation:

$$I = \frac{V}{\sqrt{(X_{c2} + X_{c3'})^2 + (R_2 + R_{3'})^2}} \quad (73)$$

where
I=current in amperes
V=voltage between the electrodes in volts
$X_{C2}$=capacitive reactance of shoulder region in ohms
$X_{C3}$=capacitive reactance of air in ohms
$R_2$=resistance of shoulder region in ohms
$R_3$=resistance of air in ohms.

Using the capacitive reactance and resistance of each of the shoulder region and air derived above, and assuming that the voltage between the electrodes is 1,000 volts, the current passing between the electrodes through the air (as well as through the shoulder region) is:

$$I = \frac{1{,}000}{\sqrt{(998.112 + 70{,}861.5)^2 + (1{,}796.6 + 0)^2}} = 0.0139 \text{ amps} \quad (74)$$

Now, the power that is dissipated in the shoulder region due to the application of the dielectric field is expressed by the following equation:

$$P_2 = R_2 \times I^2 \quad (75)$$

where
P₂=power in shoulder region in watts due to the dielectric field
R₂=resistance of shoulder region in ohms
I=current in amperes.

Using the resistance of the shoulder region and the current derived above, the power dissipated in the shoulder region due to the dielectric field is:

$$P_2 = 1{,}796.6 \times (0.0139)^2 = 0.3477 \text{ watts} \tag{76}$$

The increase in temperature of the shoulder region during the application of the dielectric field is represented by the following equation:

$$\Delta T_2 = \frac{P_2 \times t_2}{16.387 \times h_2 \times \rho_2 \times d_2} \tag{77}$$

where
$\Delta T_2$=increase in temperature of shoulder region in ° C.
$P_2$=power in shoulder region in watts due to the dielectric field
$t_2$=heating time of shoulder region in seconds
$h_2$=specific heat of shoulder region in J/g ° C.
$\rho_2$=density of shoulder region in g/cm³
$d_2$=thickness of shoulder region in inches.

Using the power in the shoulder region derived above, and assuming that the specific heat and density of the shoulder region are 3.47 J/g OC and 1.027 g/cm³, respectively, the increase in temperature of the shoulder region during the application of the dielectric field is expressed as follows:

$$\Delta T_2 = \frac{0.3477 \times t_2}{16.387 \times 3.47 \times 1.027 \times 4} = 0.00149 \times t_2 \text{ ° C.} \tag{78}$$

If the heating time is 7 seconds, the increase in temperature of the shoulder region is 0.0104° C. (or 0.0187° F.). Thus, if the human body starts at 98.6° F. (i.e. body temperature), then the temperature of the shoulder, region is 98.6187° F. at the end of the dielectric heating treatment. By contrast, as discussed above, the temperature of the chest region is 104.33° F. at the end of the dielectric heating treatment. Thus, over 300 times more heat is generated in the chest region than the shoulder region and, as a result, the chest region heats at a significantly faster rate than the shoulder region. Accordingly, it can be appreciated that the displacement of the air surrounding the shoulder region with the distilled water/acetic acid mixture is necessary to obtain a substantially constant current across the chest and shoulder regions so that the same cell type in both regions heats at substantially the same rate.

2. Treatment Region Contains Varying Amounts of Fat a. Exemplary Apparatus

Referring to FIGS. 7a and 7b, a diagram of an exemplary apparatus that may be used to generate a dielectric field between two electrodes and across a treatment region that contains varying amounts of fat is designated as reference numeral 60. Apparatus 60 includes a top electrode 62 and a bottom electrode 64, both of which are connected to an energy source or generator 66 operable to generate a dielectric field between the electrodes. Preferably, the voltage between top electrode 62 and bottom electrode 64 is substantially constant, which is accomplished by centering the treatment region at a position that is ¼λ or, alternatively, ¼λ plus a multiple of ½λ, from the power tube of generator 66 (as discussed above in connection with FIG. 1) or providing multiple points at this position (as discussed above in connection with FIG. 3). As can be seen, top electrode 62 and bottom electrode 64 each comprise a plate, and disposed between the electrodes is a top bladder 68 (attached to top electrode 62) and a bottom bladder 70 (attached to bottom electrode 64). Top and bottom bladders 68, 70 may be made of any flexible and stretchable material, such as silicone rubber or liquid silicone rubber sold by Rhodia Silicones, so that the bladders are able to stretch when filled with a flowable material.

Bottom bladder 70 is continuous in the sense that a single bottom bladder extends across the surface area of bottom electrode 64. However, top bladder 68 includes multiple compartments located adjacent to the treatment region. In the illustrated embodiment, top bladder 68 includes forty-eight compartments arranged in a matrix of twelve rows and four columns. Only one of the four columns can be seen in FIGS. 7a and 7b, and the twelve rows have been labeled 68a-68l. Each compartment has a width of 6 inches and a length of 6 inches such that the compartments collectively extend across the surface area of top electrode 62. Of course, one skilled in the art will appreciate that any number of compartments with various dimensions may be used in accordance with the present invention, which will vary depending on the size of the treatment region. One skilled in the art will appreciate that a larger number of compartments with smaller dimensions will enable the body to be broken down into a larger number of sub-regions within the treatment region.

As shown in FIG. 7b, the treatment region in the illustrated embodiment comprises a human body with one or more sub-regions that contain an amount of fat. The body is placed within the cavity between top and bottom bladders 68, 70, and various flowable materials (discussed below) are injected into the compartments of top bladder 68 and into bottom bladder 70 so as to displace the air between the body and electrodes. As such, the top of the body is in contact with top bladder 68 and the bottom of the body is in contact with bottom bladder 70. One skilled in the art will appreciate that apparatus 60 may have a variety of different structural configurations that are encompassed by the present invention. It should also be understood that the treatment region may comprise only a portion of a body that is positioned between the electrodes of apparatus 60.

b. General Methodology II

For cases in which the treatment region includes two or more sub-regions, that contain different amounts of fat, a different methodology is used in order to accommodate for the different amounts of fat. In this case, the treatment region is placed in apparatus 60 shown in FIG. 7a, and various flowable materials (described below) are injected into the compartment(s) of top bladder 68 and into bottom bladder 70. The compositions of the flowable materials, which will vary depending on the amount of fat (if any) located in the various sub-regions, are chosen so as to obtain a substantially constant current across the treatment region so that the same cell type in different sub-regions of the treatment region heats at substantially the same rate.

In accordance with this methodology, a flowable material with a high dielectric constant is injected into the compartment(s) of top bladder 68 adjacent any sub-region that contains an amount of fat (assuming that the amount of fat in the sub-region is constant). Preferably, the flowable material has a dielectric constant greater than 30, more preferably greater than 70, and most preferably greater than 100. The composition of the flowable material is calculated so as to allow a substantially constant current to be applied across the treatment region. For example, it will be seen in Example 2 below that the flowable material comprises a mixture of 77.62% hydrogen peroxide and 22.4% distilled water. It should be understood that a flowable material with a higher dielectric constant will allow this methodology to be used with a greater amount of fat. It should also be understood that if there are multiple sub-regions that contain different amounts of fat, then the composition of the flowable material will be different in the various sub-regions (e.g., the percentages of hydrogen peroxide and distilled water will vary depending on the amount of fat).

Also, the compartment(s) of top bladder 68 adjacent a sub-region that is substantially fat-free are filled with a flowable material that simulates the body, i.e., either (i) a flowable material having a dissipation factor and dielectric constant that are substantially the same as the body (e.g., if the body comprises a human body and the dielectric field has a frequency of 40 MHz, the dissipation factor and dielectric constant of the flowable material are about 1.8 and about 71, respectively) or (ii) a flowable material having a low dissipation factor (i.e., a dissipation factor preferably less than 1.0, more preferably less than 0.5, and most preferably less than 0.3) and a dielectric constant that are selected such that the flowable material simulates the body (e.g., 83.42% distilled water and 16.58% acetic acid, as calculated in Example 1 above). This same flowable material is also injected into bottom bladder 70. Of course, if the thickness of such a sub-region is the same as the spacing between the electrodes (as' in Example 2 below), then there is no need to inject the flowable material into the adjacent compartment(s) of top bladder 68.

In addition, the compartment(s) of top bladder 68 adjacent a region that does not require treatment are filled with air or another flowable material with a very low dielectric constant in order to significantly reduce the current in the region. Preferably, the flowable material has a dielectric constant less than 10, more preferably less than 6, and most preferably less than 4 (e.g., air has a dielectric constant of about 1).

Example 2

An example using this general methodology is provided below in which a human body is placed in apparatus 60 shown in FIG. 7a, wherein the treatment region includes the chest and stomach regions of the body. The chest region (which is substantially fat-free). has a thickness of 8 inches, and the stomach region has a thickness of 6⅜ inches, which includes 6 inches of non-fatty tissue and ⅜ inches of fat. For the sake of clarity, the 6 inches of non-fatty tissue (e.g., epidermal/dermal skin cells, stomach cells, circulatory cells, etc) in the stomach region will be referred to hereinafter as the "stomach region," and the ⅜ inches of fat (e.g., adipose tissue) will be referred to hereinafter as the "stomach fat."

The top and bottom electrodes 62 and 44 are spaced 8 inches apart, and the voltage between the electrodes is 1,000 volts. The compartments of top bladder 68 located adjacent the chest region (i.e., the row of compartments labeled 68d) are empty because the thickness of the chest region is the same as the spacing, between the electrodes. A flowable material comprising hydrogen peroxide mixed with distilled water is injected into the compartments of top bladder 68 adjacent the stomach region/stomach fat (i.e., the two rows of compartments labeled 68e and 68f) and into bottom bladder 70. Accordingly, the material between the electrodes in the chest region is the human body (i.e., the 8 inch chest region) and the material between the electrodes in the stomach region is the human body and the hydrogen peroxide/distilled water mixture (i.e., the 6 inch stomach region, the ⅜ inch stomach fat, and 1⅝ inches of the hydrogen peroxide/distilled water mixture). In this example, air is injected into the remaining compartments of top bladder 68, which will result in minimal heating of the remaining regions of the body.

The following table identifies the dielectric constant, dissipation factor, specific heat and density of each of the materials between the electrodes, assuming that the frequency of the dielectric field is 40 MHz:

|  | Dielectric Constant | Dissipation Factor | Specific Heat (J/g ° C.) | Density (g/cm³) |
|---|---|---|---|---|
| Human Body (Chest and Stomach Regions) | 71 | 1.8 | 3.47 | 1.027 |
| Human Body (Stomach Fat) | 11 | 1.1 | 1.93 | 0.918 |
| Hydrogen Peroxide | 128 | .04 | 2.619 | 1.463 |
| Distilled Water | 76 | .005 | 4.18 | 1 |

In order to obtain a substantially constant current across the chest and stomach regions of the body so that the same cell type in both regions heats at substantially the same rate, the current passing through the stomach region, stomach fat and surrounding hydrogen peroxide/distilled water mixture must be substantially the same as the current passing through the chest region. The following calculations are performed to determine the volume of hydrogen peroxide and the volume of distilled water that will result in a substantially constant current across the chest and stomach regions of the body. In the following equations, the subscript 1 denotes the chest region of the body, the subscript 2 denotes the stomach region of the body, the subscript 3 denotes the stomach fat, and the subscript 4 denotes the hydrogen peroxide/distilled water mixture (wherein the subscript hp denotes the hydrogen peroxide and the subscript dw denotes the distilled water in certain equations).

Calculations for Chest Region

The capacitance, capacitive reactance and resistance of the chest region are the same as those calculated in equations (7), (9) and (11) of Example 1 above, as follows:

$$C_1 = 1.9932 \text{ pF} \tag{79}$$

$$X_{C1} = 1,996.2 \text{ ohms} \tag{80}$$

$$R_1 = 3,593.2 \text{ ohms} \tag{81}$$

Also, the current passing between the electrodes through the chest region and the power dissipated in the chest region due to the application of the dielectric field are the same as those calculated in equations (13) and (15) of Example 1 above as follows:

$$I = 0.24328 \text{ amps} \tag{82}$$

$$P_1 = 212.67 \text{ watts} \tag{83}$$

In addition, the increase in temperature of the chest region during the application of the dielectric field is the same as that calculated in equation (18) of Example 1, as follows:

$$\Delta T_1 = 0.4552 \times t_1 \text{ ° C.} \tag{84}$$

Calculations for Stomach Region, Stomach Fat and Hydrogen Peroxide/Distilled Water Mixture The capacitance of the stomach region is expressed by the following equation:

$$C_2 = \frac{\varepsilon_2 \times A \times 0.2249}{d_2} \tag{85}$$

where
 $C_2$=capacitance of stomach region in picofarads
 $\varepsilon_2$=dielectric constant of stomach region
 A=area of stomach region in inches$^2$
 $d_2$=thickness of stomach region in inches.

Assuming that the dielectric constant of the stomach region is 71 and that the unit area is 1 inch$^2$, the capacitance of the stomach region is:

$$C_2 = \frac{71 \times 1 \times 0.2249}{6} = 2.6576 \text{ pF} \tag{86}$$

The capacitive, reactance of the stomach region is then given by the following equation:

$$X_{C2} = \frac{1}{2 \times \pi \times f \times C_2} \tag{87}$$

where
 $X_{C2}$=capacitive reactance of stomach region in ohms
 f=frequency of dielectric field in hertz
 $C_2$=capacitance of stomach region in farads.

Using the capacitance of the stomach region derived above and assuming that the frequency of the dielectric field is 40 MHz, the capacitive reactance of the stomach region is:

$$X_{C2} = \frac{1}{2 \times \pi \times 40 \times 10^6 \times 2.6576 \times 10^{-12}} = 1{,}497.2 \text{ ohms} \tag{88}$$

The resistance of the stomach region is equal to the product of the dissipation factor of the stomach region and the capacitive reactance of the stomach region, as follows:

$$R_2 = df_2 \times X_{C2} \tag{89}$$

where
 $R_2$=resistance of stomach region in ohms.
 $df_2$=dissipation factor of stomach region
 $X_{C2}$=capacitive reactance of stomach region in ohms.

Using the capacitive reactance of the stomach region derived above and assuming that the dissipation factor of the stomach region is 1.8, the resistance of the stomach region is expressed as follows:

$$R_2 = 1.8 \times 1{,}497.2 = 2{,}694.96 \text{ ohms} \tag{90}$$

Now, the capacitance of the stomach fat is expressed by the following equation:

$$C_3 = \frac{\varepsilon_3 \times A \times 0.2249}{d_3} \tag{91}$$

where
 $C_3$=capacitance of stomach fat in picofards
 $\varepsilon_3$=dielectric constant of stomach fat
 A=area of stomach fat in inches$^2$
 $d_3$=thickness of stomach fat in inches.

For a unit area of 1 inch$^2$, the capacitance of the stomach fat is:

$$C_3 = \frac{11 \times 1 \times 0.2249}{0.375} = 6.588 \text{ pF} \tag{92}$$

The capacitive reactance of the stomach fat is then given by the following equation:

$$X_{C3} = \frac{1}{2 \times \pi \times f \times C_3} \tag{93}$$

where
 $X_{C3}$=capacitive reactance of stomach fat in ohms
 f=frequency of dielectric field in hertz
 $C_3$=capacitance of stomach fat in farads.

Using the capacitance of the stomach fat derived above and assuming, that the frequency of the dielectric field is 40 MHz, the capacitive, reactance of the stomach fat is:

$$X_{C3} = \frac{1}{2 \times \pi \times 40 \times 10^6 \times \varepsilon_3 \times 6.588 \times 10^{-12}} = 603.96 \text{ ohms} \tag{94}$$

The resistance of the stomach fat is equal to the product of the dissipation factor of the stomach fat and the capacitive reactance of the stomach fat, as follows:

$$R_3 = df_3 \times X_{C3} \tag{95}$$

where
 $R_3$=resistance of stomach fat in ohms
 $df_3$=dissipation factor of stomach fat
 $X_{C3}$=capacitive reactance of stomach fat in ohms.

Using the capacitive reactance of the stomach fat derived above, the resistance of the stomach fat is:

$$R_3 = 1.1 \times 603.96 = 664.4 \text{ ohms} \tag{96}$$

Now, assume that the hydrogen peroxide/distilled water mixture consists of a volume of hydrogen peroxide represented by x and a volume of distilled water represented by 1−x. The capacitance of the hydrogen peroxide is expressed by the following equation:

$$C_{hp} = \frac{\varepsilon_{hp} \times A \times 0.2249}{d_{hp}} \tag{97}$$

where
 $C_{hp}$=capacitance of hydrogen peroxide in picofarads.
 $\varepsilon_{hp}$=dielectric constant of hydrogen peroxide
 A=area of hydrogen peroxide in inches$^2$
 $d_{hp}$=thickness of hydrogen peroxide in inches.

For a unit area of 1 inch$^2$, the capacitance of the hydrogen peroxide is:

$$C_{hp} = \frac{128 \times 1 \times 0.224}{1.625 \times x} = \frac{17.69}{x} \text{ pF} \tag{98}$$

Similarly, the capacitance of the distilled water is expressed by the following equation:

$$C_{dw} = \frac{\varepsilon_{dw} \times A \times 0.2249}{d_{dw}} \tag{99}$$

where
- $C_{dw}$=capacitance of distilled water in picofarads
- $\epsilon_{dw}$=dielectric constant of distilled water
- A=area of distilled water in inches$^2$
- $d_{dw}$=thickness of distilled water in inches.

For a unit area of 1 inch$^2$, the capacitance of the distilled water is:

$$C_{dw} = \frac{76 \times 1 \times 0.2249}{1.625(1-x)} = \frac{10.5}{1-x} \text{ pF} \qquad (100)$$

The capacitive reactance of the hydrogen peroxide is given by the following equation:

$$X_{Chp} = \frac{1}{2 \times \pi \times f \times C_{hp}} \qquad (101)$$

where
- $X_{Chp}$=capacitive reactance of hydrogen peroxide in ohms
- f=frequency of dielectric field in hertz
- $C_{hp}$=capacitance of hydrogen peroxide in farads.

Using the capacitance of the hydrogen peroxide derived above and assuming that the frequency of the dielectric field is 40 MHz, the capacitive reactance of the hydrogen peroxide is:

$$X_{Chp} = \frac{x}{2 \times \pi \times 40 \times 10^6 \times 17.69 \times 10^{-12}} = 224.9x \text{ ohms} \qquad (102)$$

Similarly, the capacitive reactance of the distilled water is then given by the following equation:

$$X_{Cdw} = \frac{1}{2 \times \pi \times f \times C_{dw}} \qquad (103)$$

where
- $X_{Cdw}$=capacitive reactance of distilled water in ohms
- f=frequency of dielectric field in hertz
- $C_{dw}$=capacitance of distilled water in farads.

Using the capacitance of the distilled water derived above and assuming that the frequency of the dielectric field is 40 MHz, the capacitive reactance of the distilled water is:

$$X_{Cdw} = \frac{1-x}{2 \times \pi \times 40 \times 10^6 \times 10.5 \times 10^{-12}} = 378.9(1-x) \text{ ohms} \qquad (104)$$

Now, the total capacitive reactance of the hydrogen peroxide/distilled water mixture is expressed as follows:

$$X_{C4} = X_{Chp} + X_{Cdw} \qquad (1.05)$$

where
- $X_{C4}$=capacitive reactance of mixture in ohms
- $X_{Chp}$=capacitive reactance of hydrogen peroxide in ohms
- $X_{Cdw}$=capacitive reactance of distilled water in ohms.

Using the capacitive reactance of each of the hydrogen peroxide and distilled water derived above, the capacitive reactance of the hydrogen peroxide/distilled water mixture is:

$$X_{C4} = (224.9x) + (378.9(1-x)) = 378.9 - 154x \text{ ohms} \qquad (106)$$

The resistance of the hydrogen peroxide is equal to the product of the dissipation factor of the hydrogen peroxide and the capacitive reactance of the hydrogen peroxide, as follows:

$$R_{hp} = df_{hp} \times X_{Chp} \qquad (107)$$

where
- $R_{hp}$=resistance of hydrogen peroxide in ohms
- $df_{hp}$=dissipation factor of hydrogen peroxide
- $X_{Chp}$=capacitive reactance of hydrogen peroxide in ohms.

Using the capacitive reactance of the hydrogen peroxide derived above and assuming that the dissipation factor of hydrogen peroxide is 0.04, the resistance of the hydrogen peroxide is:

$$R_{hp} = 0.04 \times 224.9x = 9x \text{ ohms} \qquad (108)$$

Similarly, the resistance of the distilled water is equal to the product of the dissipation factor of the distilled water and the capacitive reactance of the distilled water, as follows:

$$R_{dw} = df_{dw} \times X_{Cdw} \qquad (109)$$

where
- $R_{dw}$=resistance of distilled water in ohms
- $df_{dw}$=dissipation factor of distilled water
- $X_{Cdw}$=capacitive reactance of distilled water in ohms.

Using the capacitive reactance of the distilled water derived above and assuming that the dissipation factor of distilled water is 0.005, the resistance of the distilled water is:

$$R_{dw} = 0.005 \times 378.9(1-x) = 1.89(1-x) \text{ ohms} \qquad (110)$$

Now, the total resistance of the hydrogen peroxide/distilled water mixture is expressed as follows:

$$R_4 = R_{hp} + R_{dw} \qquad (111)$$

where
- $R_4$=resistance of mixture in ohms
- $R_{hp}$=resistance of hydrogen peroxide in ohms
- $R_{dw}$=resistance of distilled water in ohms.

Using the resistance of each of the hydrogen peroxide and distilled water derived above, the resistance of the hydrogen peroxide/distilled water mixture is:

$$R_4 = (9x) + (0.89(1-x)) = 1.89 - 7.11x \text{ ohms} \qquad (112)$$

Next, the current passing between the electrodes through the hydrogen peroxide/distilled water mixture, stomach fat and stomach region is represented by the following equation:

$$I = \frac{V}{\sqrt{(X_{C2} + X_{C3} + X_{C4})^2 + (R_2 + R_3 + R_4)^2}} \qquad (113)$$

where
- I=current in amperes
- V=voltage between the electrodes in volts
- $X_{C2}$=capacitive reactance of stomach region in ohms
- $X_{C3}$=capacitive reactance of stomach fat in ohms
- $X_{C4}$=capacitive reactance of mixture in ohms
- $R_2$=resistance of stomach region in ohms.
- $R_3$=resistance of stomach fat in ohms
- $R_4$=resistance of mixture in ohms.

The current passing between the electrodes through the hydrogen peroxide/distilled water mixture, stomach fat and stomach region must be substantially the same as the current passing between the electrodes through the chest region. Using the current passing between the electrodes through the chest region derived above, using the capacitive reactance and resistance of each of the stomach region, stomach fat and hydrogen peroxide/distilled mixture derived above, and assuming that the voltage between the electrodes is 1,000 volts, the current passing, between the electrodes through the hydrogen peroxide/distilled water mixture, stomach fat and stomach region is:

$$0.24328 = \frac{1{,}000}{\sqrt{(2{,}480.06 - 154x)^2 + (3{,}361.25 + 7.11x)^2}} \text{ amps} \qquad (114)$$

By solving equation (114) for x, it can be seen that the volume of hydrogen peroxide represented by x is 0.776 and, thus, the volume of distilled water represented by (1−x) is 0.224. In other words, the hydrogen peroxide/distilled water mixture is 77.62% hydrogen peroxide (by volume) and 22.4% distilled water (by volume).

The power that is dissipated in the stomach region due to the application of the dielectric field is expressed by the following equation:

$$P_2 = R_2 \times I^2 \qquad (115)$$

where
$P_2$=power in stomach region in watts due to the dielectric field
$R_2$=resistance of stomach region in ohms
I=current in amperes.

Using the resistance of the stomach region and the current derived above, the power dissipated in the stomach region due to the dielectric field is:

$$P_2 = (2{,}694.96) \times (0.24328)^2 = 159.45 \text{ watts} \qquad (116)$$

The increase in temperature of the stomach region during the application of the dielectric field is represented by the following equation:

$$\Delta T_2 = \frac{P_2 \times t_2}{16.387(h_2 \times \rho_2 \times d_2)} \qquad (117)$$

where
$\Delta T_2$=increase in temperature of stomach region in ° C.
$P_2$=power in stomach region in watts due to the dielectric field
$t_2$=heating time of stomach region in seconds
$h_2$=specific heat of stomach region in J/g ° C.
$\rho_2$=density of stomach region in g/cm$^3$
$d_2$=thickness of stomach region in inches.

Using the power in the stomach region derived above and assuming that the specific heat and density of the stomach region are 3.47 J/g° C. and 1.027 g/cm$^3$, respectively, the increase in temperature of the stomach region during the application of the dielectric field is expressed as follows:

$$\Delta T_2 = \frac{159.45 \times t_2}{16.387(3.47 \times 1.027 \times 6)} = 0.4552 \times t_2 \text{ ° C.} \qquad (118)$$

Similarly, the power that is dissipated in the stomach fat due to the application of the dielectric field is expressed by the following equation:

$$P_3 = R_3 \times I^2 \qquad (119)$$

where
$P_3$=power in stomach fat in watts due to the dielectric field
$R_3$=resistance of stomach fat in ohms
I=current in amperes.

Using the resistance of the stomach fat and the current derived above, the power dissipated in the stomach fat due to the dielectric field is:

$$P_3 = (664.4) \times (0.24328)^2 = 39.32 \text{ watts} \qquad (120)$$

The increase in temperature of the stomach fat during the application of the dielectric field is represented by the following equation:

$$\Delta T_3 = \frac{P_3 \times t_2}{16.387(h_3 \times \rho_3 \times d_3)} \qquad (121)$$

where
$\Delta T_3$=increase in temperature of stomach fat in ° C.
$P_3$=power in stomach fat in watts due to the dielectric field
$t_3$=heating time of stomach fat in seconds
$h_3$=specific heat of stomach fat in J/g ° C.,
$\rho_3$=density of stomach fat in g/cm$^3$
$d_3$=thickness of stomach fat in inches.

Using the power in the stomach fat derived above and assuming that the specific heat and density of the stomach fat are 1.93 J/g ° C. and 0.918 g/cm$^3$, respectively, the increase in temperature of the stomach fat during the application of the dielectric field is expressed as follows:

$$\Delta T_3 = \frac{39.32 \times t_2}{16.387(1.93 \times 0.918 \times 0.375)} = 3.61 \times t_3 \text{ ° C.} \qquad (122)$$

Similarly, the power that is dissipated in, the hydrogen peroxide/distilled water mixture due to the application of the dielectric field is expressed by the following equation:

$$P_4 = R_4 \times I^2 \qquad (123)$$

where
$P_4$=power in mixture in watts due to the dielectric field
$R_4$=resistance of mixture in ohms
I=current in amperes.

Using the resistance of the hydrogen peroxide/distilled water mixture (with x=0.776) and the current derived above, the power dissipated in the hydrogen peroxide/distilled water mixture due to the dielectric field is:

$$P_4 = (2.957) \times (0.24328)^2 = 0.438 \text{ watts} \qquad (124)$$

The increase in temperature of the hydrogen peroxide/distilled water mixture during the application of the dielectric field is represented by the following equation:

$$\Delta T_4 = \frac{P_4 \times t_4}{16.387(h_4 \times \rho_4 \times d_4)} \qquad (125)$$

where
$\Delta T_4$=increase, in temperature of mixture in ° C.
$P_4$=power in mixture in watts due to the dielectric field.
$t_4$=heating time of mixture n in seconds.
$h_4$=specific heat of mixture in J/g ° C.
$\rho_4$=density of mixture in g/cm$^3$
$d_4$=thickness of mixture in inches.

Using the power in the hydrogen peroxide/distilled water mixture derived above and assuming that the specific heat of the hydrogen peroxide/distilled water mixture is 2.969 (i.e., (2.619×0.776)+(4.18×0.224)) and that the density of the hydrogen peroxide/distilled water mixture is 1.359 (i.e., (1.463×0.776)+(1×0.224)), the increase in temperature of the hydrogen peroxide/distilled water mixture during the application of the dielectric field is expressed as follows:

$$\Delta T_4 = \frac{0.438 \times t_4}{16.387(2.969 \times 1.359 \times 1.625)} = 0.004 \times t_4 \; ^\circ C. \quad (126)$$

Exemplary Change in Temperature after 7 Seconds

As set forth above, the increase in temperature of the chest region, stomach region, stomach fat and hydrogen peroxide/distilled water mixture during the application of the dielectric field are expressed as follows:

$\Delta T_1 = 0.4552 \times t_1 \; ^\circ C.$  (127)

$\Delta T_2 = 0.4552 \times t_2 \; ^\circ C.$  (128)

$\Delta T_3 = 3.61 \times t \; ^\circ C.$  (129)

$\Delta T_4 = 0.004 \times t_4 \; ^\circ C.$  (130)

If, for example, the heating time is 7 seconds (i.e., the human body is exposed to the dielectric field for 7 seconds), the increase in temperature of the chest and stomach regions is 3.18° C. (or 5.73° F.), the increase in temperature of the stomach fat is 25.28° C. (or 45.5° F.), and the increase in temperature of the hydrogen peroxide/distilled water mixture is 0.0285° C. (or 0.05° F.). Thus, if the human body starts at 98.6° F. (i.e., body temperature) and the hydrogen peroxide/distilled water mixture starts at 77° F., then the temperatures of the chest and stomach regions, stomach fat and the hydrogen peroxide/distilled water mixture are 104.33° F., 123.88° F. and 77.05° F., respectively, at the end of the dielectric heating treatment.

In this example, it can be seen that the chest and stomach regions heat at the same rate. The stomach fat heats at a much faster rate, and will liquefy during the dielectric heating treatment. Preferably, the liquefied stomach fat is removed from the body through any means known in the art (e.g., syringe or liposuction). It can; also be seen that the temperature of the hydrogen peroxide/distilled water mixture is relatively low at the end of the dielectric heating treatment (i.e., 77.05° F.). Accordingly, the hydrogen peroxide/distilled water mixture does not heat the skin of the human body during the dielectric heating treatment and also serves to cool the body upon completion of the dielectric heating treatment. Further, the hydrogen peroxide/distilled water mixture may be chilled prior to, during and/or after the dielectric heating treatment so as to provide an even greater cooling effect on the human body.

c. General Methodology III

There are cases in which the amount of fat in a sub-region (e.g., the stomach region) is large enough that it would be difficult to obtain a substantially constant current across the treatment region using the general methodology described above. As such, for larger amounts of fat, a different methodology is used in which a treatment region is placed in apparatus 60 shown in FIG. 7a, and a conductive flowable material is injected into the compartment(s) of top bladder 68 adjacent any sub-region with a large amount of fat in order to effectively narrow the gap between the electrodes. Various other flowable materials (described below) are then injected into the other compartment(s) of top bladder 68 and into bottom bladder 70. The compositions of the flowable materials are chosen so as to obtain a substantially constant current across the treatment region so that the same cell type in different sub-regions of the treatment region heats at substantially the same rate.

In accordance with this methodology, the compartment(s) of top bladder 68 adjacent any sub-region region that is substantially fat-free are filled with a flowable material with a low dielectric constant. Preferably, the flowable material has a dielectric constant less than 50, more preferably less than 30, and most preferably less than 10. For example, it will be seen in Example 3 below that the flowable material comprises acetic acid, which has a dielectric constant of 6.2. Of course, other flowable materials may be used including, but not limited to, a mixture of distilled water and acetic acid. The thickness of the flowable material is calculated so as to allow a substantially constant current to be applied across the treatment region. It should be understood that the thickness of the flowable material will depend on the dielectric constant of the flowable material. Specifically, a flowable material with a higher dielectric constant will require a greater thickness of the flowable material, and a flowable material with a lower dielectric constant will require a smaller thickness of the flowable material.

Also, bottom bladder (70) is filled with a flowable material that simulates the body, i.e., either (i) a flowable material having: a dissipation factor and dielectric constant that are substantially the same as the body (e.g., if the body comprises a human body and the dielectric field has a frequency of 40 MHz, the dissipation, factor and dielectric constant of the flowable material are about 1.8 and about 71, respectively) or (ii) a flowable material having a low dissipation factor (i.e., a dissipation factor preferably less than 1.0, more preferably less than 0.5, and most preferably less than 0.3) and a dielectric constant that are selected such that the flowable material simulates the body (e.g., 83.42% distilled water and 16.58% acetic acid, as calculated in Example 1 above).

In addition, the compartment(s) of top bladder 68 adjacent a region that does not require treatment are filled with air or another flowable material with a very low dielectric constant in order to significantly reduce the current in the region. Preferably, the flowable material has a dielectric constant less than 10, more preferably less than 6, and most preferably less than 4 (e.g., air has a dielectric constant of about 1).

Example 3

An example using this general methodology is provided below in which a human body is placed in apparatus 60 shown in FIG. 7a, wherein the treatment region includes the chest and stomach regions of the body. The chest region (which is substantially fat-free) has a thickness of 8 inches, and the stomach region has a thickness of 8 inches, which includes 7 inches of non-fatty tissue and 1 inch of fat. For the sake of clarity, the 7 inches of non-fatty tissue (e.g., epidermal/dermal skin cells, stomach cells, circulatory cells, etc) in the stomach region will be referred to hereinafter as the "stomach region," and the 1 inch of fat (e.g., adipose tissue) will be referred to hereinafter as the "stomach fat."

Acetic acid is injected into the compartments of top bladder 68 adjacent the chest region (e.g., the row of compartments labeled 68d) and into bottom bladder 70. Then, the compartments of top bladder 68 adjacent the stomach region/stomach fat (e.g., the two rows of compartments labeled 68e and 68f) are filled with a liquid conductor to effectively narrow the spacing between the electrodes in this sub-region. In this example, the liquid conductor comprises a eutectic compound consisting of 62.5% gallium, 21.5% indium and 16.0% tin (made by MCP Metal Specialties Inc.). Air is injected into the remaining compartments of top bladder 68, which will result in minimal heating of the remaining regions of the body. In this example, the voltage between the top and bottom electrodes 62 and 64 is 1,000 volts.

The following table identifies the dielectric constant, dissipation factor, specific heat and density of each of the materials between the electrodes, assuming that the frequency of the dielectric field is 40 MHz:

|  | Dielectric Constant | Dissipation Factor | Specific Heat (J/g ° C.) | Density (g/cm$^3$) |
|---|---|---|---|---|
| Human Body (Chest and Stomach Regions) | 71 | 1.8 | 3.47 | 1.027 |
| Human Body (Stomach Fat) | 11 | 1.1 | 1.93 | 0.918 |
| Acetic Acid | 6.2 | 0.0262 | 2.18 | 1.05 |

In order to obtain a substantially constant current across the chest and stomach regions of the body so that the same cell type in both regions heats at substantially the same rate, the current passing through the stomach fat and stomach region must be substantially the same as the current passing through the acetic acid and chest region. The following calculations are performed to determine the thickness of the acetic acid that will result in a substantially constant current across the chest and stomach regions of the body (wherein the same thickness of liquid conductor will also be used). In the following equations, the subscript 1 denotes the acetic acid, the subscript 2 denotes the chest region of the body, the subscript 3 denotes the stomach region of the body, and the subscript 4 denotes the stomach fat.

Calculations for Acetic Acid and Chest Region

First, the capacitance of the acetic acid is expressed by the following equation:

$$C_1 = \frac{\varepsilon_1 \times A \times 0.2249}{d_1} \tag{131}$$

where
$C_1$=capacitance of acetic acid in picofarads
$\varepsilon_1$=dielectric constant of acetic acid
A=area of acetic acid in inches$^2$
$d_1$=thickness of acetic acid in inches.

Assuming that the dielectric constant of the acetic acid is 6.2 and that the unit area is 1 inch$^2$, the capacitance of the acetic acid is:

$$C_1 = \frac{6.2 \times 1 \times 0.2249}{d_1} = \frac{1.39}{d_1} \text{pF} \tag{132}$$

Similarly, the capacitance of the chest region is expressed by the following equation:

$$C_2 = \frac{\varepsilon_2 \times A \times 0.2249}{d_2} \tag{133}$$

where
$C_2$=capacitance of chest region, in picofarads
$\varepsilon_2$=dielectric constant of chest region
A=area of chest region in inches$^2$
$d_2$=thickness of chest region in inches.

Assuming that the dielectric constant of the chest region is 71 and that the unit area is 1 inch$^2$, the capacitance of the chest region is:

$$C_2 = \frac{71 \times 1 \times 0.2249}{8} = 1.993 \text{ pF} \tag{134}$$

The capacitive reactance of the acetic acid is given by the following equation:

$$X_{C1} = \frac{1}{2 \times \pi \times f \times C_1} \tag{135}$$

where
$X_{C1}$=capacitive reactance of acetic acid in ohms
f=frequency of dielectric field in hertz
$C_1$=capacitance of acetic acid in farads.

Using the capacitance of the acetic acid derived above and assuming that the frequency of the dielectric field is 40 MHz, the capacitive reactance of the acetic acid is:

$$X_{C1} = \frac{1}{2 \times \pi \times 40 \times 10^6 \times \frac{1.39 \times 10^{-12}}{d_1}} = 2,857 \times d_1 \text{ ohms} \tag{136}$$

Similarly, the capacitive reactance of the chest region is given by the following equation:

$$X_{C2} = \frac{1}{2 \times \pi \times f \times C_2} \tag{137}$$

where
$X_{C2}$=capacitive reactance of chest region in ohms
f=frequency of dielectric field in hertz
$C_2$=capacitance of chest region in farads.

Using the capacitance of the chest region derived above and assuming that the frequency of the dielectric field is 40 MHz, the capacitive reactance of the chest region is:

$$X_{C2} = \frac{1}{2 \times \pi \times 40 \times 10^6 \times 1.993 \times 10^{-12}} = 1,996.4 \text{ ohms} \tag{138}$$

Then, the total capacitive reactance of the acetic acid and chest region is obtained by adding equations (136) and (138), as follows:

$$X_{C1,C2} = 2,857.6 d_1 + 1,996.4 \text{ ohms} \tag{139}$$

The resistance of the acetic acid is equal to the product of the dissipation factor of the acetic acid and the capacitive reactance of the acetic acid, as follows:

$$R_1 = df_1 \times X_{C1} \quad (140)$$

where
R$_1$=resistance of acetic acid in ohms
df$_1$=dissipation factor of acetic acid
X$_{C1}$=capacitive reactance of acetic acid in ohms.

Using the capacitive reactance of the acetic acid derived above and assuming that the dissipation factor of the acetic acid is 0.0262, the resistance of the acetic acid is expressed as follows:

$$R_1 = 0.0262 \times 2{,}857.6 \times d_1 = 74.87 \times d_1 \text{ ohms} \quad (141)$$

Similarly, the resistance of the chest region is equal to the product of the dissipation factor of the chest region and the capacitive reactance of the chest region, as follows:

$$R_2 = df_2 \times X_{C2} \quad (142)$$

where
R$_2$=resistance of chest region in ohms
df$_2$=dissipation factor of chest region
X$_{C2}$=capacitive reactance of chest region in ohms Using the capacitive reactance of the chest region derived above and assuming that the dissipation factor of the chest region is 1.8, the resistance of the chest region is expressed as follows:

$$R_2 = 1.8 \times 1{,}996.4 = 3{,}593.52 \text{ ohms} \quad (143)$$

Then, the total resistance of the acetic acid and chest region is obtained by adding equations (141) and (143), as follows:

$$R_{1,2} = (74.87 \times d_1) + 3{,}593.52 \text{ ohms} \quad (144)$$

Next, the current passing between the electrodes through the acetic acid and chest region is represented by the following equation:

$$I = \frac{V}{\sqrt{X_{C1,2}^2 + R_{1,2}^2}} \quad (145)$$

where
I=current in amperes
V=voltage between the electrodes in volts
X$_{C1,2}$=total capacitive reactance of acetic acid/chest region in ohms
R$_{1,2}$=total resistance of acetic acid/chest region in ohms.

Using the total capacitive reactance and total resistance of the acetic acid and chest region derived above, and assuming that the voltage between the electrodes is 1,000 volts, the current passing between the electrodes through the acetic acid and chest region is:

$$I = \frac{1{,}000}{\sqrt{(1{,}996.4 + 2{,}857.6 d_1)^2 + (3{,}593.52 + 74.87 d_1)^2}} \text{ amps} \quad (146)$$

Calculations for Stomach Region and Stomach Fat

The capacitance of the stomach region is expressed by the following equation:

$$C_3 = \frac{\varepsilon_3 \times A \times 0.2249}{d_3} \quad (147)$$

where
C$_3$=capacitance of stomach region in picofarads
∈$_3$=dielectric constant of stomach region
A=area of stomach region in inches$^2$
d$_3$=thickness of stomach region in inches.

Assuming that the dielectric constant of the stomach region is 71 and that the unit area is 1 inch$^2$, the capacitance of the stomach region is:

$$C_3 = \frac{71 \times 1 \times 0.2249}{7} = 2.278 \text{ pF} \quad (148)$$

Similarly, the capacitance of the stomach fat is expressed by the following equation:

$$C_4 = \frac{\varepsilon_4 \times A \times 0.2249}{d_4} \quad (149)$$

where
C$_4$=capacitance of stomach fat in picofarads
∈$_4$=dielectric constant of stomach fat
A=area of stomach fat in inches$^2$
d$_4$=thickness of stomach fat in inches.

Assuming that the dielectric constant of the stomach fat is 11 and that the unit area is 1 inch$^2$, the capacitance of the stomach fat is:

$$C_4 = \frac{11 \times 1 \times 0.2249}{1} = 2.47 \text{ pF} \quad (150)$$

The capacitive reactance of the stomach region is given by the following equation:

$$X_{C3} = \frac{1}{2 \times \pi \times f \times C_3} \quad (151)$$

where
X$_{C3}$=capacitive reactance of stomach region in ohms
f=frequency of dielectric field in hertz
C$_3$=capacitance of stomach region in farads.

Using the capacitance of the stomach region derived above; and assuming that the frequency of the dielectric field is 40 MHz, the capacitive reactance of the stomach region is:

$$X_{C3} = \frac{1}{2 \times \pi \times 40 \times 10^6 \times 2.278 \times 10^{-12}} = 1{,}746.7 \text{ ohms} \quad (152)$$

Similarly, the capacitive reactance of the stomach fat is given by the following equation:

$$X_{C4} = \frac{1}{2 \times \pi \times f \times C_4} \quad (153)$$

where
$X_{C4}$=capacitive reactance of stomach fat in ohms
f=frequency of dielectric field in hertz
$C_4$=capacitance of stomach fat in farads.

Using the capacitance of the stomach fat derived above and assuming that the frequency of the dielectric field is 40 MHz, the capacitive reactance of the stomach fat is:

$$X_{C4} = \frac{1}{2 \times \pi \times 40 \times 10^6 \times 2.47 \times 10^{-12}} = 1{,}610.9 \text{ ohms} \qquad (154)$$

Then, the total capacitive reactance of the stomach region and stomach fat is obtained by adding equations (152) and (154), as follows:

$$X_{C3,C4} = 1{,}746.7 + 1{,}610.9 = 3{,}357.6 \text{ ohms} \qquad (155)$$

The resistance of the stomach region is equal to the product of the dissipation factor of the stomach region and the capacitive reactance of the stomach region, as follows:

$$R_3 = df_3 \times X_{C3} \qquad (156)$$

where
$R_3$=resistance of stomach region in ohms
$df_3$=dissipation factor of stomach region
$X_{C3}$=capacitive reactance of stomach region in ohms.

Using the capacitive reactance of the stomach region derived above and assuming that the dissipation factor of the stomach region is 1.8, the resistance of the stomach region is expressed as follows:

$$R_3 = 1.8 \times 1{,}746.7 = 3{,}144.06 \text{ ohms} \qquad (157)$$

Similarly, the resistance of the stomach fat is equal to the product of the dissipation factor of the stomach fat and the capacitive reactance of the stomach fat, as follows:

$$R_4 = df_4 \times X_{C4} \qquad (158)$$

where
$R_4$=resistance of stomach fat in ohms
$df_4$=dissipation factor of stomach fat
$X_{C4}$=capacitive reactance of stomach fat in ohms.

Using the capacitive reactance of the stomach fat derived above and assuming that the dissipation factor of the stomach fat is 1.1, the resistance of the stomach fat is expressed as follows:

$$R_4 = 1.1 \times 1{,}610.9 = 1{,}772 \text{ ohms} \qquad (159)$$

Then, the total resistance of the stomach region and stomach fat is obtained by adding equations (157) and (159), as follows:

$$R_{3,4} = 3{,}144.06 + 1{,}772 = 4{,}916.06 \text{ ohms} \qquad (160)$$

Next, the current passing between the electrodes through the stomach region and stomach fat is represented by the following equation:

$$I = \frac{V}{\sqrt{X_{C3,4}^2 + R_{3,4}^2}} \qquad (161)$$

where
I=current in amperes
V=voltage between the electrodes in volts
$X_{C3,4}$=total capacitive reactance of stomach region/stomach fat in ohms $R_{3,4}$=total resistance of stomach region/stomach fat in ohms.

Using the total capacitive reactance and total resistance of the stomach region and stomach fat derived above, and assuming that the voltage between the electrodes is 1,000 volts, the current passing between the electrodes through the stomach region and stomach fat is:

$$I = \frac{1{,}000}{\sqrt{(3{,}357.6)^2 + (4{,}916.06)^2}} = 0.168 \text{ amps} \qquad (162)$$

Required Thickness of Acetic Acid

In order to obtain a substantially constant current across the chest and stomach regions of the body so that the same cell type in both regions heats at substantially the same rate, the current passing between the electrodes through the acetic acid and chest region (equation 146) must be equal to the current passing between the electrodes through the stomach region and stomach fat (equation 162), as follows:

$$0.168 = \frac{1{,}000}{\sqrt{(1{,}996.4 + 2{,}857.6 d_1)^2 + (3{,}593.52 + 74.87 d_1)^2}} \text{ amps} \qquad (163)$$

By solving equation (163) for $d_1$, it can be seen that the required thickness of the acetic acid is 0.9429 inches. Thus, the compartments of top bladder 68 adjacent the chest region (i.e., the row of compartments labeled 68d) are filled with acetic acid having a thickness of 0.9429 inches. In addition, the compartments of top bladder 68 adjacent the stomach region/stomach fat (i.e., the two rows of compartments labeled 68e and 68f) are filled with a liquid conductor having a thickness of 0.9429 inches to effectively narrow the spacing between the electrodes in this region.

Power and Change in Temperature

The power that is dissipated in the acetic acid due to the application of the dielectric field is expressed by the following equation:

$$P = R_1 \times I^2 \qquad (164)$$

where
$P_1$=power in acetic acid in watts due to the dielectric field
$R_1$=resistance of acetic acid in ohms
I=current in amperes.

Using the resistance of the acetic acid and the current derived above, the power dissipated in the acetic acid due to the dielectric field is:

$$P_1 = (74.87 \times 0.9429) \times (0.168)^2 = 1.99 \text{ watts} \qquad (165)$$

The increase in temperature of the acetic acid during the application of the dielectric field is represented by the following equation:

$$\Delta T_1 = \frac{P_1 \times t_1}{16.387(h_1 \times \rho_1 \times d_1)} \qquad (166)$$

where
$\Delta T_1$=increase in temperature of acetic acid in ° C.
$P_1$=power in acetic acid in watts due to the dielectric field
$t_1$=heating time of acetic acid in seconds $h_1$=specific heat of acetic acid in J/g ° C.
$\rho_1$=density of acetic acid in g/cm$^3$
$d_1$=thickness of acetic acid in inches.

Using the power in the acetic acid derived above and assuming that the specific heat and density of the acetic acid are 2.18 J/g ° C. and 1.05 g/cm$^3$, respectively, the increase in temperature of the acetic acid during the application of the dielectric field is expressed as follows:

$$\Delta T_1 = \frac{1.99 \times t_2}{16.387(2.18 \times 1.05 \times 0.9429)} = 0.056 \times t_1 \text{ ° C.} \quad (167)$$

Similarly, the power that is dissipated in the chest region due to the application of the dielectric field is expressed by the following equation:

$$P_2 = R_2 \times I^2 \quad (168)$$

where
$P_2$=power in chest region in watts due to the dielectric field
$R_2$=resistance of chest region in ohms
I=current in amperes.

Using the resistance of the chest region and the current derived above, the power dissipated in the chest region due to the dielectric field is:

$$P_2 = (3,593.52) \times (0.168)^2 = 101.42 \text{ watts} \quad (169)$$

The increase in temperature of the chest region during the application of the dielectric field is represented by the following equation:

$$\Delta T_2 = \frac{P_2 \times t_2}{16.387(h_2 \times \rho_2 \times d_2)} \quad (170)$$

where
$\Delta T_2$=increase in temperature of chest region in ° C.
$P_2$=power in chest region in watts due to the dielectric field
$t_2$=heating time of chest region in seconds
$h_2$=specific heat of chest region in J/g ° C.
$\rho_2$=density of chest region in g/cm$^3$
$d_2$=thickness of chest region in inches.

Using the power in the chest region derived above and assuming that the specific heat and density of the chest region are 3.47 J/g ° C. and 1.027 g/cm$^3$, respectively, the increase in temperature of the chest region during the application of the dielectric field is expressed as follows:

$$\Delta T_2 = \frac{101.42 \times t_2}{16.387(3.47 \times 1.027 \times 8)} = 0.217 \times t_2 \text{ ° C.} \quad (171)$$

Similarly, the power that is dissipated in the stomach region due to the application of the dielectric field is expressed by the following equation:

$$P_3 = R_3 \times I^2 \quad (172)$$

where
$P_3$=power in stomach region in watts due to the dielectric field
$R_3$=resistance of stomach region in ohms
I=current in amperes.

Using the resistance of the stomach region and the current derived above, the power dissipated in the stomach region due to the dielectric field is:

$$P_3 = (3,144.06) \times (0.168)^2 = 88.74 \text{ watts} \quad (173)$$

The increase in temperature of the stomach region during the application of the dielectric field is represented by the following equation:

$$\Delta T_3 = \frac{P_3 \times t_2}{16.387(h_3 \times \rho_3 \times d_3)} \quad (174)$$

where
$\Delta T_3$=increase in temperature of stomach region in ° C.
$P_3$=power in stomach region in watts due to the dielectric field
$t_3$=heating time of stomach region in seconds
$h_3$=specific heat of stomach region in J/g ° C.
$\rho_3$=density of stomach region in g/cm$^3$
$d_3$=thickness of stomach region in inches.

Using the power in the stomach region derived above and assuming that the specific heat and density of the stomach region are 3.473 μg ° C. and 1.027 g/cm$^3$, respectively, the increase in temperature of the stomach region during the application of the dielectric field is expressed as follows:

$$\Delta T_3 = \frac{88.74 \times t_3}{16.87(3.47 \times 1.027 \times 7)} = 0.217 \times t_3 \text{ ° C.} \quad (175)$$

Similarly, the power that is dissipated in the stomach fat due to the application of the dielectric field is expressed by the following equation:

$$P_4 = R_4 \times I^2 \quad (176)$$

where
$P_4$=power in stomach fat in watts due to the dielectric field
$R_4$=resistance of stomach fat in ohms
I=current in amperes.

Using the resistance of the stomach fat and the current derived above, the power dissipated in the stomach fat due to the dielectric field is:

$$P_4 = (1,772) \times (0.168)^2 = 50.01 \text{ watts} \quad (177)$$

The increase in temperature of the stomach fat during the application of the dielectric field is represented by the following equation:

$$\Delta T_4 = \frac{P_4 \times t_4}{16.387(h_4 \times \rho_4 \times d_4)} \quad (178)$$

where
$\Delta T_4$=increase in temperature of stomach fat in ° C.
$P_4$=power in stomach fat in watts due to the dielectric field
$t_4$=heating time of stomach fat in seconds
$h_4$=specific heat of stomach fat in J/g ° C.
$\rho_4$=density of stomach fat in g/cm$^3$
$d_4$=thickness of stomach fat in inches.

Using the power in the stomach fat derived above and assuming that the specific heat and density of the stomach fat are 1.93 J/g ° C. and 0.918 g/cm$^3$, respectively, the increase in temperature of the stomach fat during the application of the dielectric field is expressed as follows:

$$\Delta T_4 = \frac{50.01 \times t_4}{16.387(1.93 \times 0.918 \times 1)} = 1.72 \times t_4 \text{ °C.} \quad (179)$$

Exemplary Change in Temperature After 15 Seconds

As set forth above, the increase in temperature of the acetic acid, chest region, stomach region and stomach fat during the application of the dielectric field are expressed as follows:

$$\Delta T_1 = 0.056 \times t_1 \text{ °C.} \quad (180)$$

$$\Delta T_2 = 0.217 \times t_2 \text{ °C.} \quad (181)$$

$$\Delta T_3 = 0.217 \times t_3 \text{ °C.} \quad (182)$$

$$\Delta T_4 = 1.72 \times t_4 \text{ °C.} \quad (183)$$

If, for example, the heating time is 15 seconds (i.e., the human body is exposed to the dielectric field for 15 seconds), the increase in temperature of the acetic acid is 0.843° C. (or 1.5° F.), the increase in temperature of the chest and stomach regions is 3.256° C. (or 5.86° F.), and the increase in temperature of the stomach fat is 25.8° C. (or 46.44° F.). Thus, if the human body starts at 98.6° F. (i.e., body temperature) and the acetic acid starts at 77° F., then the temperatures of the acetic acid, chest and stomach regions and stomach fat are 78.5° F., 104.46° F. and 145° F., respectively, at the end of the dielectric heating treatment.

In this example, it can be seen that the chest and stomach regions heat at the same rate. The stomach fat heats at a much faster rate and will liquefy during the dielectric heating treatment. Preferably, the liquefied stomach fat is removed from the body through any means known in the art (e.g., syringe or liposuction). It can also be seen that the temperature of the acetic acid is relatively low at the end of the dielectric heating, treatment (i.e., 78.5° F.). Accordingly, the acetic acid does not heat the skin of the human body during the dielectric heating treatment and also serves to cool the body upon completion of the dielectric heating treatment. Further, the acetic acid may be chilled prior to, during and/or after the dielectric heating treatment so as to provide an even greater cooling effect on the human body.

IV. Dielectric Heating of Biological Targets of a Subject

As discussed in Section III above, the apparatuses and methods of the present invention enable a substantially constant current to be obtained across a treatment region of a subject when subjected to a dielectric field. If the current is substantially constant, then the ratio of the change in temperature of the biological targets (e.g., target cells) to the change in temperature of the non-targets (e.g., non-target cells) is dependent on the dissipation factor, dielectric constant, specific heat and density of the cell types, as follows:

$$\frac{\Delta T_2}{\Delta T_1} = \frac{df_2 \times \varepsilon_1 \times h_1 \times \rho_1}{df_1 \times \varepsilon_2 \times h_2 \times \rho_2} \quad (184)$$

where
$\Delta T_1$=increase in temperature of non-target cells in ° C.
$\Delta T_2$=increase in temperature of target cells in ° C.
$df_1$=dissipation factor of non-target cells
$df_2$=dissipation factor of target cells
$\varepsilon_1$=dielectric constant of non-target cells
$\varepsilon_2$=dielectric-constant of target cells
$h_1$=specific heat of non-target cells in J/g ° C.
$h_2$=specific heat of target cells in J/g ° C.
$\rho_1$=density of non-target cells in g/cm$^3$
$\rho_2$=density of target cells in g/cm$^3$.

As such, if it is desired to heat the target cells X times faster than the non-target cells, then this ratio must be X. In some cases, the ratio of X occurs naturally. In other cases, the ratio of X is achieved by introducing, a dielectric heating modulator into the subject that will bind to the target cells (as described above) in a percentage sufficient to raise the temperature of the target cells to a temperature where the target cells will be killed, without damaging the non-target cells.

It should be understood that the dissipation factor, dielectric, constant, specific heat, and density of the non-target cells and target cells vary with temperature. Therefore, it is preferable to calculate the ratio in equation (184) at regular time intervals (e.g., second time intervals). By doing so, it is possible to use the values for the dissipation factor, dielectric constant, specific heat, and density that correspond to the temperature of the non-target cells and target cells at that particular point in time. Preferably, a computer is programmed to perform these calculations in order to simplify the analysis.

It should also be understood that equation (184) does not consider the effects of thermal conductivity on the temperatures of the non-target cells and target cells at the end of the dielectric heating treatment. In general, it is preferable to utilize a short heating time so as to minimize the effects of thermal conductivity between the non-target cells and target cells (which can be accomplished, for example, by using a higher voltage). A longer heating time has two disadvantages: (1) all or a portion of the non-target cells surrounding the target cells may be heated by thermal conductivity so as to kill the non-target cells; and (2) if a small number of target cells are surrounded by a larger number of non-target cells, the non-target cells may cool the target cells by thermal conductivity to a point where the target cells will not be killed. Thus, if a longer heating time is utilized for a particular application, it is necessary to consider the effects of thermal conductivity on the temperatures of the non-target cells and target cells at the end of the dielectric heating treatment. Accordingly, a short heating time is preferred.

It should further be understood that the application of equation (184) is not limited to a treatment region that includes target cells and a single type of non-target cells. Indeed, equation (184) can be applied to a treatment region that includes any number of cell types. For example, if a treatment region includes n different types of non-target cells, it is only necessary to focus on the non-target cell type that heats at the fastest rate. If the non-target cell type that heats at the fastest rate is not killed, then none of the other non-target cell types will be killed by the dielectric heating. In order to demonstrate this principle, the derivation of equation (184) is provided below for cases in which (1) a treatment region includes two different cell types and (2) a treatment region includes six different cell types.

Two Cell Types

In this analysis, it is assumed that the treatment region includes a first type of non-target cells and a second type of target cells, wherein the subscripts 1 and 2 are used to denote each of these cell types.

The capacitance of the non-target cells is expressed by the following equation:

$$C_1 = \frac{\varepsilon_1 \times A \times 0.2249}{d_1} \tag{185}$$

where
 $C_1$=capacitance of non-target cells in picofarads
 $\varepsilon_1$=dielectric constant of non-target cells
 A=area of non-target cells in inches$^2$
 $d_1$=thickness of non-target cells in inches.

Similarly, the capacitance of the target cells is expressed by the following equation:

$$C_2 = \frac{\varepsilon_2 \times A \times 0.2249}{d_2} \tag{186}$$

where
 $C_2$=capacitance of target cells in picofarads
 $\varepsilon_2$=dielectric constant of target cells.
 A=area of target cells in inches$^2$
 $d_2$=thickness of target cells in inches.

The capacitive reactance of the non-target cells is given by the following equation:

$$X_{C1} = \frac{1}{2 \times \pi \times f \times C_1} \tag{187}$$

where
 $X_{C1}$=capacitive reactance of non-target cells, in ohms
 f=frequency of dielectric field in hertz
 $C_1$=capacitance of non-target cells in farads.

Using the capacitance of the non-target cells derived above, the capacitive reactance of the non-target cells is:

$$X_{C1} = \frac{d_1}{2 \times \pi \times f \times \varepsilon_1 \times A \times 0.2249 \times 10^{-12}} \text{ ohms} \tag{188}$$

Similarly, the capacitive reactance of the target cells is given by the following equation:

$$X_{C2} = \frac{1}{2 \times \pi \times f \times C_2} \tag{189}$$

where
 $X_{C2}$=capacitive reactance of target cells in ohms
 f=frequency of dielectric field in hertz
 $C_2$=capacitance of target cells in farads.

Using the capacitance of the target cells derived above, the capacitive reactance of the target cells is:

$$X_{C2} = \frac{d_2}{2 \times \pi \times f \times \varepsilon_2 \times A \times 0.2249 \times 10^{-12}} \text{ ohms} \tag{190}$$

Then, the total capacitive reactance of the non-target cells and the target cells is obtained by adding equations (188) and (190), as follows:

$$X_C = \frac{\varepsilon_1 d_2 + \varepsilon_2 d_1}{\varepsilon_1 \times \varepsilon_2 \times 2 \times \pi \times f \times A \times 0.2249 \times 10^{-12}} \text{ ohms} \tag{191}$$

The resistance of the non-target cells is equal to the product of the dissipation factor of the non-target cells and the capacitive reactance of the non-target cells, as follows:

$$R_1 = df_1 \times X_{C1} \tag{192}$$

where
 $R_1$=resistance of non-target cells in ohms
 $df_1$=dissipation factor of non-target cells
 $X_{C1}$=capacitive reactance of non-target cells in ohms.

Using the capacitive reactance of the non-target cells derived above, the resistance of the non-target cells is:

$$R_1 = \frac{df_1 \times d_1}{\varepsilon_1 \times A \times 2 \times \pi \times f \times 0.2249 \times 10^{-12}} \text{ ohms} \tag{193}$$

Similarly, the resistance of the target cells is equal to the product of the dissipation factor of the target cells and the capacitive reactance of the target cells, as follows:

$$R_2 = df_2 \times X_{C2} \tag{194}$$

where
 $R_2$=resistance of target cells in ohms
 $df_2$=dissipation factor of target cells
 $X_{C2}$=capacitive reactance of target cells in ohms.

Using the capacitive reactance of the target cells derived above, the resistance of the target cells is:

$$R_2 = \frac{df_2 \times d_2}{\varepsilon_2 \times A \times 2 \times \pi \times f \times 0.2249 \times 10^{-12}} \text{ ohms} \tag{195}$$

Then, the total resistance of the non-target cells and the target cells is obtained by adding equations (193) and (195), as follows:

$$R = \frac{1}{A \times 2 \times \pi \times f \times 0.2249 \times 10^{-12}} \left( \frac{df_1 \times d_1}{\varepsilon_1} + \frac{df_2 \times d_2}{\varepsilon_2} \right) \text{ ohms} \tag{196}$$

The current passing between the electrodes through the non target cells and the target cells is represented by the following equation:

$$I = \frac{V}{\sqrt{X_C^2 + R^2}} \tag{197}$$

where
 I=current in amperes
 V=voltage between the electrodes in volts
 $X_C$=total capacitive reactance of non-target and target cells in ohms
 R=total resistance of non-target and target cells in ohms.

Using the total capacitive reactance and total resistance of the non-target cells and the target cells derived above, the current passing between the electrodes through the non-target cells and the target cells is:

$$I = \frac{V \times A \times 2 \times \pi \times f \times 0.2249 \times 10^{-12} \times \varepsilon_1 \times \varepsilon_2}{\sqrt{(\varepsilon_1 d_2 + \varepsilon_2 d_1)^2 + (df_1 d_1 \varepsilon_2 + df_2 d_2 \varepsilon_1)^2}} \quad (198)$$

The power that is dissipated in the non-target cells due to the application of the dielectric field is expressed by the following equation:

$$P_1 = R_1 \times I^2 \quad (199)$$

where
$P_1$=power in non-target cells in watts due to the dielectric field
$R_1$=resistance of non-target cells in ohms
I=current in amperes.

Using the resistance of the non-target cells and current derived above, the power dissipated in the non-target cells due to the dielectric field is:

$$P_1 = \frac{df_1 \times d_1 \times V^2 \times A \times 2 \times \pi \times f \times 0.2249 \times 10^{-12} \times \varepsilon_1 \times \varepsilon_2^2}{(\varepsilon_1 d_2 + \varepsilon_2 d_1)^2 + (df_1 d_1 \varepsilon_2 + df_2 d_2 \varepsilon_1)^2} \quad (200)$$

Similarly, the power that is dissipated in the target cells due to the application of the dielectric field is expressed by the following equation:

$$P_2 = R_2 \times I^2 \quad (201)$$

where
$P_2$=power in target cells in watts due to the dielectric field
$R_2$=resistance of target cells in ohms
I=current in amperes.

Using the resistance of the target cells and current derived above, the power dissipated in the target cells due to the dielectric field is:

$$P_2 = \frac{df_2 \times d_2 \times V^2 \times A \times 2 \times \pi \times f \times 0.2249 \times 10^{-12} \times \varepsilon_2 \times \varepsilon_1^2}{(\varepsilon_2 d_1 + \varepsilon_1 d_2)^2 + (df_2 d_2 \varepsilon_1 + df_1 d_1 \varepsilon_2)^2} \quad (202)$$

The increase in temperature of the non-target cells during the application of the dielectric field is represented by the following equation:

$$\Delta T_1 = \frac{P_1 \times t_1}{16.387(h_1 \times \rho_1 \times d_1)} \quad (203)$$

where
$\Delta T_1$=increase in temperature of non-target cells in ° C.
$P_1$=power in non-target cells in watts due to the dielectric field
$t_1$=heating time of non-target cells in seconds
$h_1$=specific heat of non-target cells in J/g ° C.
$\rho_1$=density of non-target cells in g/cm$^3$
$d_1$=thickness of non-target cells in inches.

Using the power in the non-target cells derived above, the increase in temperature of the non-target cells during the application of the dielectric field is:

$$\Delta T_1 = \frac{df_1 \times V^2 \times A \times 2 \times \pi \times f \times 0.2249 \times 10^{-12} \times \varepsilon_1 \times \varepsilon_2^2 \times t_1}{16.387 \times h_1 \times \rho_1 ((\varepsilon_1 d_2 + \varepsilon_2 d_1)^2 + (df_1 d_1 \varepsilon_2 + df_2 d_2 \varepsilon_1)^2)} \quad (204)$$

Similarly, the increase in temperature of the target cells during the application of the dielectric field is represented by the following equation:

$$\Delta T_2 = \frac{P_2 \times t_2}{16.387(h_2 \times \rho_2 \times d_2)} \quad (205)$$

where
$\Delta T_2$=increase in temperature of target cells in ° C.
$P_2$=power in target cells in watts due to the dielectric field
$t_2$=heating time of target cells in seconds
$h_2$=specific heat of target cells in J/g ° C.
$\rho_2$=density of target cells in g/cm$^3$
$d_2$=thickness of target cells in inches.

Using the power in the target cells derived above, the increase in temperature of the target cells during the application of the dielectric field is:

$$\Delta T_2 = \frac{df_2 \times V^2 \times A \times 2 \times \pi \times f \times 0.2249 \times 10^{-12} \times \varepsilon_1 \times \varepsilon_2^2 \times t_2}{16.387 \times h_2 \times \rho_2 ((\varepsilon_2 d_1 + \varepsilon_1 d_2)^2 + (df_2 d_2 \varepsilon_1 + df_1 d_1 \varepsilon_2)^2)} \quad (206)$$

The ratio of the change in temperature of the target cells to the change in temperature of the non-target cells is then expressed by dividing equations (206) and (204), as follows:

$$\frac{\Delta T_2}{\Delta T_1} = \frac{df_2 \times \varepsilon_1 \times h_1 \times \rho_1}{df_1 \times \varepsilon_2 \times h_2 \times \rho_2} \quad (207)$$

Thus, it can be seen that equation (207) is the same as equation (184) set forth above.

Six Cell Types

The analysis set forth above becomes more complex as additional cell types are included in the treatment region. In the following analysis, it is assumed that the treatment region includes five different types of non-target cells and a sixth type of target cells, wherein the subscripts 1-6 are used to denote each of these cell types:

The capacitance of each of the cell types is expressed by the following equation:

$$C_i = \frac{\varepsilon_i \times A \times 0.2249}{d_i} \quad (208)$$

where
$C_i$=capacitance of cell type in picofarads
$\varepsilon_i$=dielectric constant of cell type
A=area of cell type in inches$^2$
$d_i$=thickness of cell type in inches.

Looking at the same area A of 1 inch$^2$ for each of the six cell types, the capacitance of each of the cell types is expressed as follows:

$$C_1 = \frac{\varepsilon_1 \times 0.2249}{d_1} \text{pF} \tag{209}$$

$$C_2 = \frac{\varepsilon_2 \times 0.2249}{d_2} \text{pF} \tag{210}$$

$$C_3 = \frac{\varepsilon_3 \times 0.2249}{d_3} \text{pF} \tag{211}$$

$$C_4 = \frac{\varepsilon_4 \times 0.2249}{d_4} \text{pF} \tag{212}$$

$$C_5 = \frac{\varepsilon_5 \times 0.2249}{d_5} \text{pF} \tag{213}$$

$$C_6 = \frac{\varepsilon_6 \times 0.2249}{d_6} \text{pF} \tag{214}$$

The total capacitance of all six cell types is represented by the following equation:

$$C = \frac{C_1 \times C_2 \times C_3 \times C_4 \times C_5 \times C_6}{\begin{array}{c} C_1 C_2 C_3 C_4 C_5 + C_1 C_2 C_3 C_4 C_6 + \\ C_1 C_2 C_3 C_5 C_6 + C_1 C_2 C_4 C_5 C_6 + \\ C_1 C_3 C_4 C_5 C_6 + C_2 C_3 C_4 C_5 C_6 \end{array}} \tag{215}$$

where

C=equivalent capacitance of six cell types in picofarads
$C_1$=capacitance of cell type 1 in picofarads
$C_2$=capacitance of cell type 2, in picofarads
$C_3$=capacitance of cell type 3 in picofarads
$C_4$=capacitance of cell type 4 in picofarads
$C_5$=capacitance of cell type 5 in picofarads
$C_6$=capacitance of cell type 6 in picofarads.

Using the capacitance of each of the cell types derived above, the total capacitance is:

$$C = \frac{.2249 \times 10^{-12} \left( \frac{\varepsilon_1}{d_1} \times \frac{\varepsilon_2}{d_2} \times \frac{\varepsilon_3}{d_3} \times \frac{\varepsilon_4}{d_4} \times \frac{\varepsilon_5}{d_5} \times \frac{\varepsilon_6}{d_6} \right)}{\begin{array}{c} \frac{\varepsilon_1 \times \varepsilon_2 \times \varepsilon_3 \times \varepsilon_4 \times \varepsilon_5}{d_1 \times d_2 \times d_3 \times d_4 \times d_5} + \frac{\varepsilon_1 \times \varepsilon_2 \times \varepsilon_3 \times \varepsilon_4 \times \varepsilon_6}{d_1 \times d_2 \times d_3 \times d_4 \times d_6} + \\ \frac{\varepsilon_1 \times \varepsilon_2 \times \varepsilon_3 \times \varepsilon_5 \times \varepsilon_6}{d_1 \times d_2 \times d_3 \times d_5 \times d_6} + \frac{\varepsilon_1 \times \varepsilon_2 \times \varepsilon_4 \times \varepsilon_5 \times \varepsilon_6}{d_1 \times d_2 \times d_4 \times d_5 \times d_6} + \\ \frac{\varepsilon_1 \times \varepsilon_3 \times \varepsilon_4 \times \varepsilon_5 \times \varepsilon_6}{d_1 \times d_3 \times d_4 \times d_5 \times d_6} + \frac{\varepsilon_2 \times \varepsilon_3 \times \varepsilon_4 \times \varepsilon_5 \times \varepsilon_6}{d_2 \times d_3 \times d_4 \times d_5 \times d_6} \end{array}} \tag{216}$$

The capacitive reactance of each of the cell types is given by the following equation:

$$X_{Ci} = \frac{1}{2 \times \pi \times f \times C_i} \tag{217}$$

where $X_{Ci}$=capacitive reactance of cell type in ohms
f=frequency of dielectric field in hertz
$C_i$=capacitance of cell type in farads.

Using the capacitance of each of the cell types derived above and assuming that the frequency of the dielectric field is 40 MHz, the capacitive reactance of each of the cell types is expressed as follows:

$$X_{C1} = \frac{17,716 \times d_1}{\varepsilon_1} \text{ohms} \tag{218}$$

$$X_{C2} = \frac{17,716 \times d_2}{\varepsilon_2} \text{ohms} \tag{219}$$

$$X_{C3} = \frac{17,716 \times d_3}{\varepsilon_3} \text{ohms} \tag{220}$$

$$X_{C4} = \frac{17,716 \times d_4}{\varepsilon_4} \text{ohms} \tag{221}$$

$$X_{C5} = \frac{17,716 \times d_5}{\varepsilon_5} \text{ohms} \tag{222}$$

$$X_{C6} = \frac{17,716 \times d_6}{\varepsilon_6} \text{ohms} \tag{223}$$

Also, the total capacitive reactance of all six cell types is given by the following equation:

$$X_C = \frac{1}{2 \times \pi \times f \times C} \tag{224}$$

where $X_C$=total capacitive reactance of six cell types in ohms
f=frequency of dielectric field in hertz
C=total capacitance of six cell types in farads.

Using the total capacitance of all six cell types derived above and assuming that the frequency of the dielectric field is 40 MHz, the total capacitive reactance of the six cell types is expressed as follows:

$$X_C = \frac{17,716 \left( \begin{array}{c} \frac{\varepsilon_1 \times \varepsilon_2 \times \varepsilon_3 \times \varepsilon_4 \times \varepsilon_5}{d_1 \times d_2 \times d_3 \times d_4 \times d_5} + \frac{\varepsilon_1 \times \varepsilon_2 \times \varepsilon_3 \times \varepsilon_4 \times \varepsilon_6}{d_1 \times d_2 \times d_3 \times d_4 \times d_6} + \\ \frac{\varepsilon_1 \times \varepsilon_2 \times \varepsilon_3 \times \varepsilon_5 \times \varepsilon_6}{d_1 \times d_2 \times d_3 \times d_5 \times d_6} + \frac{\varepsilon_1 \times \varepsilon_2 \times \varepsilon_4 \times \varepsilon_5 \times \varepsilon_6}{d_1 \times d_2 \times d_4 \times d_5 \times d_6} + \\ \frac{\varepsilon_1 \times \varepsilon_3 \times \varepsilon_4 \times \varepsilon_5 \times \varepsilon_6}{d_1 \times d_3 \times d_4 \times d_5 \times d_6} + \frac{\varepsilon_2 \times \varepsilon_3 \times \varepsilon_4 \times \varepsilon_5 \times \varepsilon_6}{d_2 \times d_3 \times d_4 \times d_5 \times d_6} \end{array} \right)}{\left( \frac{\varepsilon_1}{d_1} \times \frac{\varepsilon_2}{d_2} \times \frac{\varepsilon_3}{d_3} \times \frac{\varepsilon_4}{d_4} \times \frac{\varepsilon_5}{d_5} \times \frac{\varepsilon_6}{d_6} \right)} \tag{225}$$

The resistance of each of the cell types is equal to the product of the dissipation factor of the cell type and the capacitive reactance of the cell type, as follows:

$$R_i = df_i \times X_{Ci} \tag{226}$$

where $R_i$=resistance of cell type in ohms
$df_i$=dissipation factor of cell type
$X_{Ci}$=capacitive reactance of cell type in ohms.

Using the capacitive reactance of each of the cell types derived above, the resistance of each of the cell types is:

$$R_1 = \frac{17,716 \times df_1 \times d_1}{\varepsilon_1} \text{ohms} \tag{227}$$

$$R_2 = \frac{17,716 \times df_2 \times d_2}{\varepsilon_2} \text{ohms} \tag{228}$$

$$R_3 = \frac{17,716 \times df_3 \times d_3}{\varepsilon_3} \text{ohms} \tag{229}$$

$$R_4 = \frac{17,716 \times df_4 \times d_4}{\varepsilon_4} \text{ohms} \tag{230}$$

$$R_5 = \frac{17,716 \times df_5 \times d_5}{\varepsilon_5} \text{ ohms} \quad (231)$$

$$R_6 = \frac{17,716 \times df_6 \times d_6}{\varepsilon_6} \text{ ohms} \quad (232)$$

Then, the total resistance of all six cell types is obtained by adding equations (227) to (232), as follows:

$$R = 17,716 \left( \frac{df_1 d_1}{\varepsilon_1} + \frac{df_2 d_2}{\varepsilon_2} + \frac{df_3 d_3}{\varepsilon_3} + \frac{df_4 d_4}{\varepsilon_4} + \frac{df_5 d_5}{\varepsilon_5} + \frac{df_6 d_6}{\varepsilon_6} \right). \quad (233)$$

The current passing between the electrodes through the six cell types is represented by the following equation:

$$I = \frac{V}{\sqrt{X_C^2 + R^2}} \quad (234)$$

where

I=current in amperes
V=voltage between the electrodes in volts
$X_C$=total capacitive reactance of six cell types in ohms
R=total resistance of six cell types in ohms.

Using the total capacitive reactance and total resistance of the six cell types derived above, the current passing between the six cell types is:

$$I = \frac{(V \times 56.44 \times 10^{-6} \times \varepsilon_1 \varepsilon_2 \varepsilon_3 \varepsilon_4 \varepsilon_5 \varepsilon_6)}{\sqrt{\begin{array}{c}(\varepsilon_1\varepsilon_2\varepsilon_3\varepsilon_4\varepsilon_5 d_6 + \varepsilon_1\varepsilon_2\varepsilon_3\varepsilon_4\varepsilon_6 d_5 + \varepsilon_1\varepsilon_2\varepsilon_3\varepsilon_5\varepsilon_6 d_4 + \\ \varepsilon_1\varepsilon_2\varepsilon_4\varepsilon_5\varepsilon_6 d_3 + \varepsilon_1\varepsilon_3\varepsilon_4\varepsilon_5\varepsilon_6 d_2 + \varepsilon_2\varepsilon_3\varepsilon_4\varepsilon_5\varepsilon_6 d_1)^2 + \\ (df_1 d_1 \varepsilon_2\varepsilon_3\varepsilon_4\varepsilon_5\varepsilon_6 + df_2 d_2 \varepsilon_1\varepsilon_3\varepsilon_4\varepsilon_5\varepsilon_6 + df_3 d_3 \varepsilon_1\varepsilon_2\varepsilon_4\varepsilon_5\varepsilon_6 + \\ df_4 d_4 \varepsilon_1\varepsilon_2\varepsilon_3\varepsilon_5\varepsilon_6 + df_5 d_5 \varepsilon_1\varepsilon_2\varepsilon_3\varepsilon_4\varepsilon_6 + df_6 d_6 \varepsilon_1\varepsilon_2\varepsilon_3\varepsilon_4\varepsilon_5)^2\end{array}}}$$

The power that is dissipated in each of the six cell types due to the application of the dielectric field is expressed by the following equation:

$$P_i = R_i \times I^2 \quad (236)$$

where $P_i$=power in cell type in watts due to the dielectric field
$R_i$=resistance of cell type in ohms
I=current in amperes.

Using the resistance of each cell type derived above, the power dissipated in each cell type due to the electric field is expressed as:

$$P_1 = \frac{17,716 \times df_1 \times d_1 \times I^2}{\varepsilon_1} = \frac{df_1 \times d_1}{\varepsilon_1} \times k1 \quad (237)$$

$$P_2 = \frac{17,716 \times df_2 \times d_2 \times I^2}{\varepsilon_2} = \frac{df_2 \times d_2}{\varepsilon_2} \times k1 \quad (238)$$

$$P_3 = \frac{17,716 \times df_3 \times d_3 \times I^2}{\varepsilon_3} = \frac{df_3 \times d_3}{\varepsilon_3} \times k1 \quad (239)$$

$$P_4 = \frac{17,716 \times df_4 \times d_4 \times I^2}{\varepsilon_4} = \frac{df_4 \times d_4}{\varepsilon_4} \times k1 \quad (240)$$

$$P_5 = \frac{17,716 \times df_5 \times d_5 \times I^2}{\varepsilon_5} = \frac{df_5 \times d_5}{\varepsilon_5} \times k1 \quad (241)$$

$$P_6 = \frac{17,716 \times df_6 \times d_6 \times I^2}{\varepsilon_6} = \frac{df_6 \times d_6}{\varepsilon_6} \times k1 \quad (242)$$

It should be understood that the constant k1 (i.e., 17,716× $I^2$) is the same for each of equations (237) to (242).

The increase in temperature of each of the cell types during the application of the dielectric field is represented by the following equation:

$$\Delta T_i = \frac{P_i \times t}{16.387(h_i \times \rho_i \times d_i)} \quad (243)$$

where $\Delta T_i$=increase in temperature of cell type in ° C.
$P_i$=power in cell type in watts due to the dielectric field
t=heating time of cell type in seconds
$h_i$=specific heat of cell type in J/g ° C.
$\rho_i$=specific gravity of cell type in g/cm$^3$
$d_i$=thickness of cell type in inches.

Using the power in each cell type derived above, the increase in temperature of each cell type during the application of the dielectric field is expressed as follows:

(235)

$$\Delta T_1 = \frac{df_1 \times d_1 \times k1 \times t}{\varepsilon_1 \times 16.387 \times h_1 \times \rho_1 \times d_1} = \frac{df_1}{\varepsilon_1 \times h_1 \times \rho_1} \times k2 \times t \quad (244)$$

$$\Delta T_2 = \frac{df_2 \times d_2 \times k1 \times t}{\varepsilon_2 \times 16.387 \times h_2 \times \rho_2 \times d_2} = \frac{df_2}{\varepsilon_2 \times h_2 \times \rho_2} \times k2 \times t \quad (245)$$

$$\Delta T_3 = \frac{df_3 \times d_3 \times k1 \times t}{\varepsilon_3 \times 16.387 \times h_3 \times \rho_3 \times d_3} = \frac{df_3}{\varepsilon_3 \times h_3 \times \rho_3} \times k2 \times t \quad (246)$$

$$\Delta T_4 = \frac{df_4 \times d_4 \times k1 \times t}{\varepsilon_4 \times 16.387 \times h_4 \times \rho_4 \times d_4} = \frac{df_4}{\varepsilon_4 \times h_4 \times \rho_4} \times k2 \times t \quad (247)$$

$$\Delta T_5 = \frac{df_5 \times d_5 \times k1 \times t}{\varepsilon_5 \times 16.387 \times h_5 \times \rho_5 \times d_5} = \frac{df_5}{\varepsilon_5 \times h_5 \times \rho_5} \times k2 \times t \quad (248)$$

$$\Delta T_6 = \frac{df_6 \times d_6 \times k1 \times t}{\varepsilon_6 \times 16.387 \times h_6 \times \rho_6 \times d_6} = \frac{df_6}{\varepsilon_6 \times h_6 \times \rho_6} \times k2 \times t \quad (249)$$

It should be understood that the constant k2 (i.e., k1/16.387) is the same for each of equations (244) to (249).

The ratio of the change in temperature of the target cells to the change in temperature of each of the non-target cells is then expressed by dividing equation (249) and each of equations (244) through (248), as follows:

$$\frac{\Delta T_6}{\Delta T_1} = \frac{df_6 \times \varepsilon_1 \times h_1 \times \rho_1}{df_1 \times \varepsilon_6 \times h_6 \times \rho_6} \tag{250}$$

$$\frac{\Delta T_6}{\Delta T_2} = \frac{df_6 \times \varepsilon_2 \times h_2 \times \rho_2}{df_2 \times \varepsilon_6 \times h_6 \times \rho_6} \tag{251}$$

$$\frac{\Delta T_6}{\Delta T_3} = \frac{df_6 \times \varepsilon_3 \times h_3 \times \rho_3}{df_3 \times \varepsilon_6 \times h_6 \times \rho_6} \tag{252}$$

$$\frac{\Delta T_6}{\Delta T_4} = \frac{df_6 \times \varepsilon_4 \times h_4 \times \rho_4}{df_4 \times \varepsilon_6 \times h_6 \times \rho_6} \tag{253}$$

$$\frac{\Delta T_6}{\Delta T_5} = \frac{df_6 \times \varepsilon_5 \times h_5 \times \rho_5}{df_5 \times \varepsilon_6 \times h_6 \times \rho_6} \tag{254}$$

Thus, it can be seen that each of equations (250) through (254) is the same as equation (184) set forth above. As discussed above, even though the treatment region includes five different types of non-target cells in this example, it is only necessary to focus on the non-target cell type that heats at the fastest rate. If the non-target cell type that heats at the fastest rate is not killed, then none of the other non-target cell types will be killed by the dielectric heating.

As an example, the dielectric constant, dissipation factor, specific heat and density of various cell types are summarized in the table below (assuming that the same amount of current is passing between each organ or cell type), wherein the power and change of temperature are calculated using the equations set forth above:

| | Dielectric Constant | Dissipation Factor | Specific Heat | Density | Power | Change of Temperature |
|---|---|---|---|---|---|---|
| Blood | 71 | 2.1 | 3.816 | 1.055 | 1.012 | 0.896 × t |
| Brain | 73.5 | 1.98 | 3.68 | 1.035 | 0.922 | 0.863 × t |
| Bone | 23 | 0.45 | 1.26 | 2.1 | 0.670 | 0.902 × t |
| Kidney | 80.5 | 2.05 | 3.89 | 1.05 | 0.871 | 0.760 × t |
| Spleen | 77 | 2.25 | 3.816 | 1.054 | 1.000 | 0.886 × t |
| Liver | 73.5 | 1.65 | 3.411 | 1.06 | 0.768 | 0.757 × t |
| Muscle | 77 | 2.25 | 3.47 | 1.027 | 1.000 | 1.000 × t |
| Fat | 11 | 1.1 | 1.93 | 0.918 | 3.422 | 6.883 × t |

It can be seen that fat will heat at the fastest rate, followed by muscle, bone, blood, spleen, brain, kidney and liver. Thus, if a treatment region contains a substantial amount of fat, then the adipose cell type would be considered in equation (184) in relation to the target cells. However, if a treatment region does not contain a substantial amount of fat, then the muscle cell type would be considered in equation (184) in relation to the target cells (or the cell type with the fastest heating rate that is contained within the treatment region). Of course it may be desirable to eliminate adipose cells in a treatment region such that the cell type with the next fastest heating rate would be considered in equation (184) in relation to the target cells.

A. Target Cells Naturally Heat at Faster Rate Relative to Non-Target Cells

In cases where the target cells and non-target cells have dissimilar dielectric constants, dissipation factors, specific heats, and densities, or combinations thereof, the target cells and non-target cells naturally heat at different rates. For example, it is estimated that many cells in the human body have a dielectric constant of about 71, a dissipation factor of about 1.8, a specific heat of about 3.47 J/g ° C., and a density of about 1.027 g/cm³ when placed in a dielectric field having a frequency of 40 MHz. In contrast, adipose cells (which contain large amounts of fat) have a dielectric constant of about 11, a dissipation factor of about 1.1, a specific heat of about 1.93 J/g ° C., and a density of about 0.918 g/cm³ when placed in a dielectric field having a frequency of 40 MHz. Using these values in equation (184), the ratio of the change in temperature of the adipose cells (i.e., the target, cells) to the change in temperature of the other cells in the human body (i.e., the non-target cells) is expressed by the following equation:

$$\frac{\Delta T_{adipose\ cells}}{\Delta T_{other\ cells}} = \frac{1.1 \times 71 \times 3.47 \times 1.027}{1.8 \times 11 \times 1.93 \times 0.918} = 7.93 \tag{255}$$

As such, adipose cells naturally heat approximately 7.93 times faster than the other cells in the human body upon application of the dielectric field. Thus, the adipose cells reach higher temperatures than the other cells in the human body at the end of the dielectric heating treatment such that the adipose cells may be selectively killed compared to non-adipose cell types that heat at much lower rates. Of course, it should be understood that the dissipation factor, dielectric constant, specific heat, and density of the adipose cells and the other cells in the human body vary with temperature. As such, it would be preferable to calculate the ratio in equation (184) at regular time intervals using a computer programmed to perform these calculations in order to obtain a more exact ratio, although 7.93 is a good approximation of this ratio.

B. Heating Rate of Target Cells Increased Relative to Non-Target Cells

In cases where the target cells and non-target cells have similar dielectric constants, dissipation factors, specific heats, and densities, or combinations thereof, the target cells and non-target cells naturally heat at substantially the same or similar rates. That is, the ratio of the change in temperature of the target cells to the change in temperature of the non-target cells as set forth in equation (184) is not large enough to be able to kill the target cells without damaging the non-target cells. In accordance with the present invention, and as discussed in greater detail above, the heating rate of the target cells relative to the non-target cells can be increased by introducing into the treatment region a dielectric heating modulator (which may be or may not be associated with a targeting moiety) prior to the application of the dielectric field. The dielectric heating modulator increases the dissipation factor of the target cells. As such, upon application of the dielectric field, the target cells heat at a faster rate than the non-target cells such that the target cells may be selectively killed.

Various methods may be used to determine the amount of dielectric heating modulator that is needed for a particular application. For example, with reference to equation (184), one skilled in the art will appreciate that the values for the dielectric constant, specific heat, and density of the target cells (with modulator) and non-target cells are substantially the same in this case. That is, the difference between the dielectric constant of the target cells (with modulator) compared to the dielectric constant of the non-target cells is negligible, the difference between the specific heat of the target cells (with modulator) compared to the specific heat of the non-target cells is negligible, and the difference between the density of the target cells (with modulator) compared to the density of the non-target cells is negligible. As such, equation (184) may be simplified as follows:

$$\frac{\Delta T_2}{\Delta T_1} \cong \frac{df_2}{df_1} \quad (256)$$

where $\Delta T_1$=increase in temperature of non-target cells in ° C.

$\Delta T_2$=increase in temperature of target cells (with modulator) in ° C.

$df_1$=dissipation factor of non-target cells $df_2$=dissipation factor of target cells (with modulator).

Thus, if it is desired to increase the heating rate of the target cells (with modulator) by a factor of X compared to the heating rate of the non-target cells, then the dissipation factor of the target cells (with modulator) must be X times greater than the dissipation factor of the non-target cells. It is assumed that the dissipation factor of the non-target cells is known (e.g., a value of Y). Thus, the dissipation factor of the target cells (with modulator) must have a value that is X times Y. It is possible to ascertain the dissipation factor of the target cells (with modulator) as a function of the amount of the dielectric heating modulator. For example, with reference to FIG. 12 (discussed in greater detail below), a graph is provided in which the dissipation factor of ground beef liver mixed with nanogold is plotted as a function of the amount of nanogold. Using such a graph, the required amount of the dielectric heating modulator may be determined by selecting the amount that corresponds to a dissipation factor of X times Y on the graph. Of course, other methods may be used to determine the amount of dielectric heating modulator that is needed for a particular application.

The value of X (i.e., the factor by which the heating rate of the target cells (with modulator) is increased compared to the heating rate of the non-target cells) will vary depending on the types of target and non-target cells. Preferably, the value of X is in the range of 1.5 to 8.0, is more preferably in the range of 2.0 to 6.0, and is most preferably in the range of 2.5 to 4.0. Of course, one skilled in the art will understand that there is a limit on the amount of dielectric heating modulator that may be introduced into a subject. As such, there is a practical limit on the value of X depending on the subject and the types of target and, non-target cells within the treatment region of the subject.

The desired temperature of the biological targets compared to the desired temperature of the non-targets at the end of the dielectric heating treatment will depend on the nature of the biological targets and non-targets. For example, normal non-cancerous cells in the human body are typically maintained at about 37° C. (98.5° F.) while cancer cells have a slightly elevated temperature of about 37.5° C. (99.5° F.) in the absence of any external heating. Normal non-cancerous cells are killed at about 46.5° C. (about 9.5° C. increase in the temperature) while cancer cells are killed at about 45.5° C. (about 8° C. increase, in the temperature). At lower temperatures, cell death may occur in some of the cancer cells but not all of the cancer cells. It will also be appreciated to those skilled in the art that the temperature at which a cell is killed depends on the time for which the temperature is elevated. The present invention, however, contemplates dielectric heating times of only a few minutes (e.g., 5, 4, 3, 2, or 1 minutes), and preferably for only a few seconds (e.g., 60, 50, 40, 30, 25, 20, 15, 14, 13, 12, 11, 10, 9, 8, 7, 6, 5, 4, 3, 2, 1 seconds or less). Under such circumstances, the dielectric field is applied until the temperature of the target cells (e.g., the cancer cells). is preferably elevated to about 45.5° C. or more (e.g., about 46, 47, 48, 49, 50, 51, 52, 53, 54, 55, 56, 57, 58° C. or more). Further, the dielectric field is applied so that the temperature of the non-target cells remains under 46.5° C. (e.g., 46 45, 44, 43, 42, 41, 40, 39, 38° C. or less) during the treatment. After the application of the dielectric field, the target cells cool down relatively slowly, but are maintained at elevated temperatures long enough to kill most, and preferably all, of the target cells. It will be appreciated that the dielectric field may also be applied in a cyclical manner. For example, the dielectric field may be applied for only a few seconds sufficient to bring the cancer cells to a temperature at which they will be killed. The cancer cells will then undergo cooling from that temperature once the dielectric field is removed. If the temperature, of the cancer cells is not maintained above the temperature at which the cancer cells can be killed for a sufficient period of time, another round of dielectric heating may be applied in order to increase the temperature of the cancer cells again. Such cycles of dielectric heating may be repeated. Importantly, it is preferable that the temperature of the non-targets cells will not reach a temperature for a sufficient period of time in which the non-targets are killed.

As discussed above, in certain embodiments, the present invention is directed to a method for selectively heating adipose cells in subjects via the application of a dielectric field. The treatment region contains both adipose cells (to be killed) and non-target cells (which are not adipose cells). The desired temperature of the adipose cells at the end of the dielectric heating treatment is preferably about 46° C. or more (e.g., about 46, 47, 48, 49, 50, 51, 52, 53, 54, 55, 56, 57, 58° C. or more), and the desired temperature of the non-target cells at the end of the dielectric heating treatment is preferably about 46° C. or less (e.g., about 46, 45, 44, 43, 42, 41, 40, 39, 38° C. or less). In such an embodiment, the present invention contemplates dielectric heating times of only a few minutes (e.g., 4, 3, 2, or 1 minutes), and preferably for only a few seconds (e 60, 50, 40, 30, 25, 20, 15, 14, 13, 12, 11, 10, 9, 8, 7, 6, 5, 4, 3, 2, 1 seconds or less), depending upon the voltage applied and the area and thickness of the adipose cells. If the temperature of the adipose cells is not maintained above the temperature at which the adipose cells can be killed for a sufficient period of time, another round of dielectric heating may be applied in order to increase the temperature of the adipose cells again. Such cycles of dielectric heating may be repeated. Importantly, it is preferable that the temperature of the non-targets cells will not reach a temperature for a sufficient period of time in which the non-targets are killed.

Tests on the Temperature Effects of Dielectric Heating Modulators in Fresh Ground Beef Liver or Solution Tests were performed in which the test materials comprised ground beef liver alone or mixed with different amounts of several dielectric heating modulators. The beef liver was first ground, then mixed with an amount of a dielectric heating modulator using a ⅜" Mini Micro tip attached to a Silverson mixer L4 RT-A. Other tests were performed in which the test materials comprised various dielectric heating modulators in a carrier solution having properties similar to the blood. The following dielectric heating modulators were investigated: (1) Black Pearl 2000 (Cabot Corporation); (2) Dynalyst 50KR1 (Cabot Corporation); (3) 10 nm gold particles; (4) 20 nm gold particles; (5) 50 nm gold particles; and (6) glucose.

In each test, the various test materials were placed into a mold formed of silicone rubber with a polypropylene frame. The mold contained four molding cavities, with each cavity about 0.395 inches in diameter and having a depth of 0.525 inches. The frame was about 5.9×1.3×1.5 inches. The mold was placed inside a dielectric heater (Compo Industries Model 1025-L). One end of a fiber optic cable was inserted into the middle of each molding cavity (in each case, to a depth of about one-half the thickness of the test material), and the other end of each fiber optic cable was connected to a computerized temperature recording device (Neoptix Fibcroptic Temperature Sensor: Reflex-4 and NeoLink Pro Ver. 1.3) using data acquisition software (NeoLink Pro Ver. 1.3). The mold was closed, and the test materials were heated with a dielectric field having a frequency of 27.12 MHz, wherein the voltage between the electrodes was 8,000 volts. The temperature of each of the test materials was monitored and recorded using infrared signals sent over the fiber optic cables to the temperature recording device.

Figure 8:
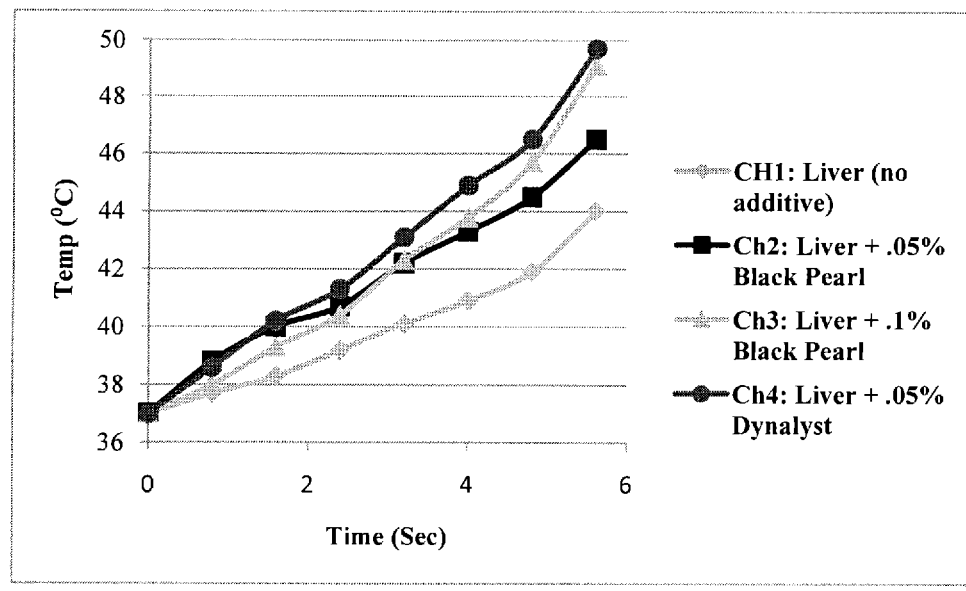
FIG. 8 shows the temperature of ground beef liver with and without various dielectric heating modulators as a function of time.

In a first test, the ground beef liver was mixed with various dielectric heating modulators to form mixtures having various concentrations, namely, 0.05 wt/wt % Black Pearl 2000, 0.1 wt/wt % Black Pearl 2000, and 0.05 wt/wt % Dynalyst 50KR1. Three of the mold cavities were filled with the test materials, and the fourth mold cavity contained ground beef liver with no dielectric heating modulator as a control. The results are shown in FIG. 8. As shown in that figure, the change in temperature was about 1.36 times faster than the control for the 0.05 wt/wt % Black Pearl, about 1.73 times faster than the control for the 1.0 wt/wt % Black. Pearl, and about 1.81 times faster than the control for the 0.05 wt/wt % Dynalyst 50KR1.

Figure 9:
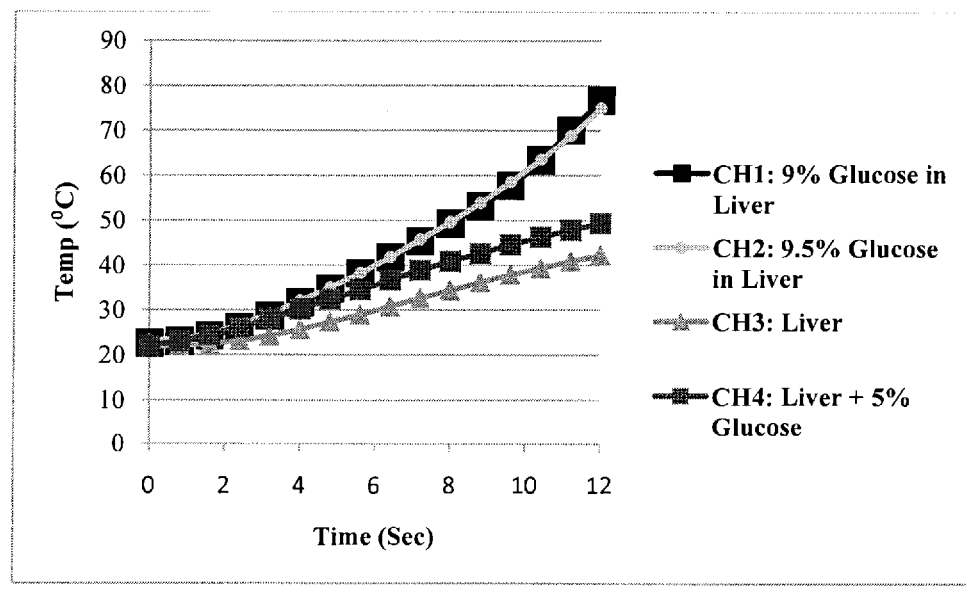
FIG. 9 shows the temperature of ground beef liver with and without glucose as the dielectric heating modulator as a function of time.

In a second test, the ground beef liver was mixed with varying amounts of glucose as the dielectric heating modulator to form mixtures having various concentrations, namely, 5, 9, and 9.5 wt/wt % glucose (e.g., 5 g of glucose per 100 g of ground beef liver). The glucose was not added to the ground beef liver in solution. Three of the mold cavities were filled with the test materials, and the fourth mold cavity contained ground beef liver with no dielectric heating modulator as a control. The results are shown in FIG. 9. As shown in that figure, the change in temperature was about 1.33, 2.64, and 2.52 times faster than the control for the 5, 9, and 9.5 wt/wt % glucose samples, respectively.

Figure 10:
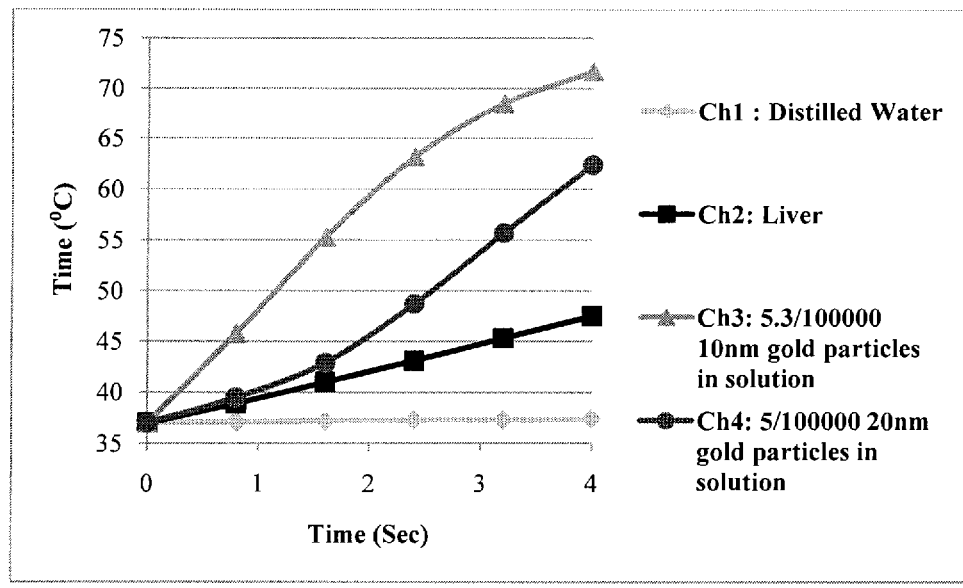
FIG. 10 shows the temperature of ground beef liver and two exemplary nanogold solutions as dielectric heating modulators as a function of time.

In a third test, the dielectric heating modulators comprised gold nanoparticles mixed in a carrier solution having properties similar to the body to form mixtures having various concentrations, namely, 0.0053 wt/vol % of 10 nm particles and 0.005 wt/vol % of 20 nm particles (e.g., 53 mg of solid particles per 1 L of solution). Two of the mold cavities were filled with the two gold nanoparticle solutions (not mixed with any beef liver), a third mold cavity was filled with distilled water, and the fourth mold cavity contained ground beef liver with no dielectric heating modulator. The results are shown in FIG. 10. As shown in that figure, the change in temperature was about 4.81 times faster than the ground beef liver for the 0.0053 wt/vol % 10 nm gold particles and about 3.37 times faster than the ground beef liver for the 0.005 wt/vol % 20 m gold particles.

Figure 11:
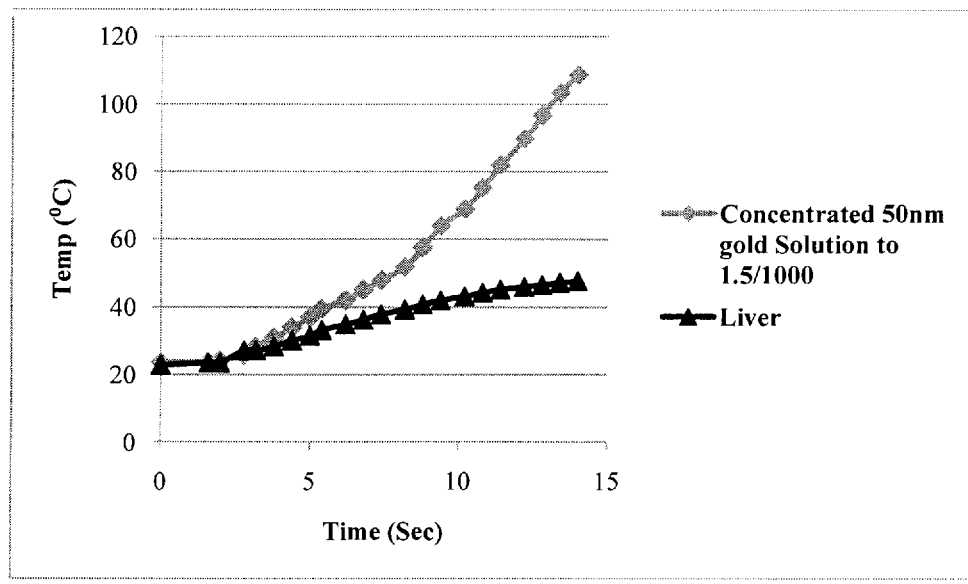
FIG. 11 shows the temperature of ground beef liver with and without a concentrated gold nanoparticle solution as a function of time.

In a fourth test, the ground beef liver was mixed with gold nanoparticles to form a mixture having a concentration of 0.15 wt/wt % of 50 nm particles (e.g., 0.15 g of solid particles per 99.85 g of ground beef liver). The 50 nm gold nanoparticles were provided in a concentrated solution of about 1:3 wt ratio of solid to carrier solution. One mold cavity was filled with the liver/nanogold test material, and another mold cavity was filled with ground beef liver with no dielectric heating modulator as a control. The results are shown in FIG. 11. As shown in that figure, the change in temperature was about 3.42 times faster than the control for the 0.15 wt/wt % 50 nm gold nanoparticles mixed with the ground beef liver.

Test to Determine the Dissipation Factor of Target Cells (with Modulator) as a Function of the Amount of Modulator In this test, the dissipation factor of ground beef liver mixed with varying concentrations of gold nanoparticles as the dielectric heating modulator was determined. A dielectric analyzer (HP 4291A RF Impedance and Material Analyzer) was used to measure the dissipation factor of each test material at 37° C. The results are summarized in the following table:

| Concentration of 10 nm gold nanoparticles (g of nanogold per 100,000 g of ground beef liver) | Dissipation Factor |
| --- | --- |
| 0 | 1.65 |
| 2 | 2.64 |
| 5.3 | 4.62 |
| 10 | 7.58 |

Figure 12:
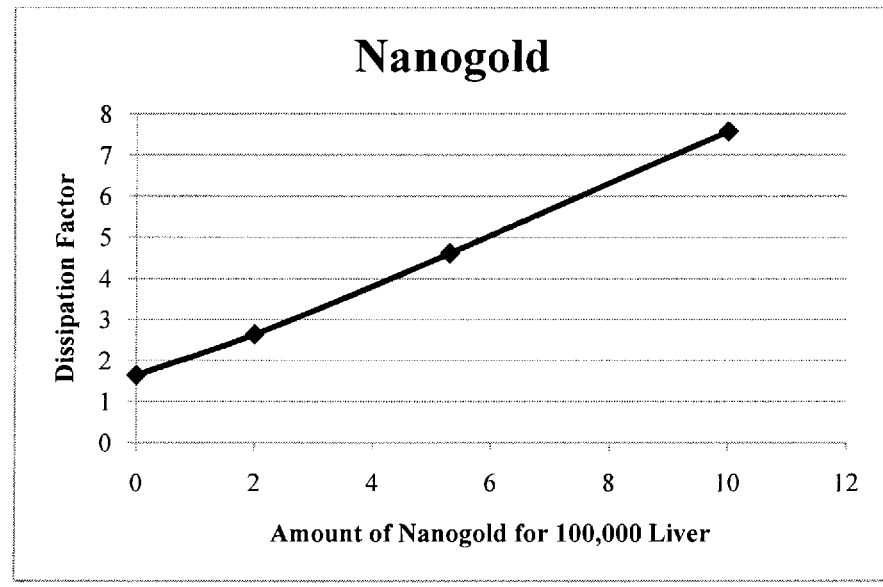
FIG. 12 shows the dissipation factor of ground beef liver mixed with concentrated gold nanoparticle solution as a function of the amount of the concentrated gold nanoparticle solution.

This data is graphically shown in FIG. 12. For simplicity, it is assumed that the dissipation factor of ground beef liver mixed with gold nanoparticles (as set forth in the table above) is comparable to the dissipation factor of cancer cells in the liver associated with gold nanoparticles. Of course, in practice, it would be desirable to determine the dissipation factor of actual cancer cells with varying concentrations of gold nanoparticles.

It will be appreciated that the information shown in FIG. 12 can be used to determine the amount of dielectric heating modulator required to heat target cells (in this case, liver cells that simulate cancer cells in the liver) to a predetermined temperature at which they will be killed (e, 50 C). It is assumed that the surrounding muscle tissue (which has a dissipation factor of about 2.25) will heat at the fastest rate of all of the cell, types in the treatment region. The muscle tissue should reach temperatures of no greater than 42.2° C. (108° F.); otherwise, the normal muscle cells will be killed.

With reference to equation (256), the ratio of the change in temperature of the liver cells mixed with gold nanoparticles (i.e., the target cells) to the change in temperature of the muscle cells (i.e., the non-target cells) is expressed by the following equation:

$$\frac{\Delta T_l}{\Delta T_m} \cong \frac{df_l}{df_m} \tag{257}$$

where $\Delta T_m$=increase in temperature of muscle cells in ° C.

$\Delta T_1$=increase in temperature of liver cells (with nanogold) in ° C.

$df_m$=dissipation factor of muscle cells $df_2$=dissipation factor of liver cells (with nanogold).

It is assumed that the starting temperature of both the liver cells (with nanogold) and muscle cells is 37° C., that the desired temperature of the liver cells (with nanogold) is 50, that the desired temperature of the muscle cells is 42.2° C., and that the dissipation factor of the muscle cells is 2.25. As such, equation (257) can be written as follows:

$$\frac{50-37}{42.2-37} \cong \frac{df_2}{2.25} \tag{258}$$

Thus, the required dissipation factor of the liver cells (with nanogold) is about 5.6. Using FIG. 12, one can determine that the dissipation factor of the liver cells is about 5.6 when about 6.5 g of 10 nm gold nanoparticles are added to 100,000 g of the ground beef liver. Thus, the amount of dielectric heating modulator that should be added can be readily determined. Again, it should be understood that the liver cells in this example are used to simulate cancer cells in the liver (which would likely be the actual target cells in practice).

Test on Fresh Bacon

A test was performed in which the test material comprised a piece of fresh bacon consisting of about 50/50 wt % meat/fat. The fatty portion and meat portion of the bacon were layered on top of one another and placed into a mold. A small piece of silicon-coated paper was placed on the top layer of the bacon and the two layers were pressed together in order to remove any air. The mold was placed inside a dielectric heater (Compo Industries Model 1025-L). One end of a fiber optic cable was inserted into the middle of each of the meat and fat portions of the bacon (in each case, to a depth of about one-half the thickness of the meat portion or fat portion), and the other end of each fiber optic cable was connected to a computerized temperature recording device (Neoptix Fiberoptic Temperature Sensor: Reflex-4 and NeoLink Pro Ver. 1.3) using data acquisition software (NeoLink Pro Ver. 1.3). The mold was closed, and the bacon was heated with a dielectric field having a frequency of 27.12 MHz, wherein the voltage between the electrodes was 8,000 volts. The temperature of the meat and fat portions of the bacon was monitored and recorded using infrared signals sent over the fiber optic cables to the temperature recording device. The following table identifies the temperatures of the meat and fat portions of the bacon at specific time intervals:

| Time (sec) | Meat Portion (° C.) | Fat Portion (° C.) |
|---|---|---|
| 0 | 37 | 37 |
| 0.6 | 38.2 | 43.6 |
| 1.0 | 39.3 | 51.5 |
| 1.4 | 41.9 | 65.2 |

Figure 13:
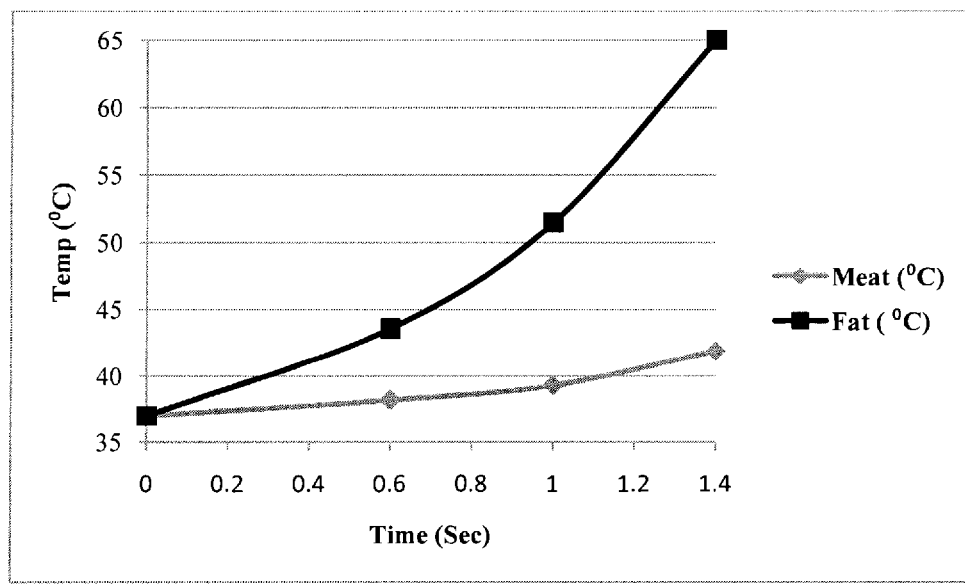
FIG. 13 shows the temperature of a meat portion and a fat portion of bacon as a function of time.

These results are graphically shown in FIG. 13. Thus, in 1.4 seconds, the change in temperature of the meat portion was 4.9° C. (41.9–37) and the change in temperature of the fat portion was 28.2° C. (65.2–37). Also, the ratio of the change in temperature of the meat portion to the change in temperature of the fat portion was about 5.76 (28.2/4.9). In other words, the fat portion heated about 5.76 times faster than the meat portion. It can be appreciated that the fat portion heated at a faster rate than the meat portion due mainly to the relatively low dielectric constant of the fat in comparison to the relatively high dielectric constant of the meat. Further, the fat portion has a lower specific heat and a lower density compared to the meat portion so that the fat portion takes less energy to heat. The dissipation factor of the fat portion is lower which will slow down the rate of heating, but overall the fat portion still heats faster than the meat portion as discussed above.

While the present invention has been described and illustrated hereinabove with reference to various exemplary apparatuses and methodologies, it should be understood that various modifications could be made to these apparatuses and methodologies without departing from the scope of the invention. Therefore, the invention is not to be limited to the exemplary apparatuses and methodologies described and illustrated hereinabove, except insofar as such limitations are included in the following claims.

What is claimed and desired to be secured by Letters Patent is as follows:

1. A method for heating a treatment region of a subject via the application of an alternating electric field, comprising:
positioning a treatment region of a subject between a first high voltage electrode and a second ground electrode, wherein said first electrode is parallel to said second electrode, wherein said treatment region comprises all or a portion of a human body that includes a plurality of cells having at least one specified cell type, and wherein said treatment region has a plurality of thicknesses extending between said first and second electrodes, wherein the plurality of thicknesses comprises a first thickness and a second thickness, wherein the first thickness is greater than the second thickness;
displacing any air located between said treatment region and said first and second electrodes with one or more flowable materials contained within one or more bladders that conform to said treatment region, wherein the first thickness is positioned such that it directly abuts the first and second electrodes, while one or more flowable materials are positioned between the second thickness and the first and second electrodes; and
activating a generator connected to said first and second electrodes, wherein said generator is operable to generate a sinusoidal signal so as to apply an alternating electric field between said first and second electrodes and across said treatment region to thereby heat said treatment region, wherein each flowable material is a mixture of at least two substances having relative concentrations calculated to optimize a dielectric constant and dissipation factor of the mixture and which cause said cells having said specified cell type to heat at a substantially same rate in either the first and second thicknesses and throughout said treatment region between said first and second electrodes.

2. The method of claim 1 wherein said first and second electrodes are sized to extend across said treatment region.

3. The method of claim 1 wherein said alternating electric field causes movement of polar molecules in said treatment region whereby friction resulting from said molecular movement translates into heat throughout said treatment region.

4. The method of claim 1 wherein said alternating electric field is generated at a frequency in the range of 1 MHz to 100 MHz.

5. The method of claim 1 wherein said alternating electric field is generated at a frequency of 27.12 MHz or 40.68 MHz.

6. The method of claim 1 wherein a difference between a voltage provided at a point on said first electrode compared to each of a plurality of additional voltages provided at each of a plurality of additional points on said first electrode is less than ±10%.

7. The method of claim 6 wherein said signal generated by said generator has a wavelength $\lambda$, and wherein said point on said first electrode is located a distance of $\frac{1}{4}\lambda$ or $\frac{1}{4}\lambda$ plus a multiple of $\frac{1}{2}\lambda$ from said single output of said generator.

8. The method of claim 1 wherein a difference between a first current passing between said first and second electrodes and through a first portion of said treatment region compared to each of a plurality of additional currents passing between said first and second electrodes and through each of a plurality of additional portions of said treatment region is less than ±25%.

9. The method of claim 8 wherein the composition of each flowable material allows said first current and said additional currents to pass between said first and second electrodes and through said treatment region.

10. A method for heating a treatment region of a subject via the application of an alternating electric field, comprising:
  positioning a treatment region of a subject comprising a first sub-region and a second sub-region between a first high voltage electrode and a second ground electrode, wherein said first and second electrodes are each sized to extend across said first and second sub-regions, wherein each of said first and second sub-regions comprises a portion of a human body that includes a plurality of cells having at least one specified cell type, wherein said first sub-region has a first thickness extending between said first and second electrodes and said second sub-region has a second thickness extending between said first and second electrodes, wherein said first thickness is less than said second thickness;
  displacing any air located between said first and second sub-regions and said first and second electrodes with one or more flowable materials; and
  activating a generator connected to said first and second electrodes, wherein said generator is operable to generate a sinusoidal signal so as to apply an alternating electric field between said first and second electrodes and across said first and second sub-regions to thereby heat said first and second sub-regions, wherein each flowable material is a mixture of at least two substances having relative concentrations calculated to optimize a dielectric constant and dissipation factor of the mixture and which cause said cells having said specified cell type to heat at a substantially same rate throughout the first and second thicknesses of said first and second sub-regions, respectively, between said first and second electrodes.

11. The method of claim 10 wherein said alternating electric field causes movement of polar molecules in said sub-regions whereby friction resulting from said molecular movement translates into heat throughout said sub-regions.

12. The method of claim 10 wherein said alternating electric field is generated at a frequency in the range of 1 MHz to 100 MHz.

13. The method of claim 10 wherein said alternating electric field is generated at a frequency of 27.12 MHz or 40.68 MHz.

14. The method of claim 10 wherein a difference between a voltage provided at a point on said first electrode compared to each of a plurality of additional voltages provided at each of a plurality of additional points on said first electrode is less than ±10%.

15. The method of claim 14 wherein said signal generated by said generator has a wavelength $\lambda$, and wherein said point on said first electrode is located a distance of $\frac{1}{4}\lambda$ or $\frac{1}{4}\lambda$ plus a multiple of $\frac{1}{2}\lambda$ from said single output of said generator.

16. The method of claim 10 wherein a difference between a first current passing between said first and second electrodes and through said first sub-region compared to a second current passing between said first and second electrodes and through said second sub-region is less than ±25%.

17. The method of claim 16 wherein the composition of each flowable material allows said first current and said second current to pass between said first and second electrodes and through said first and second sub-regions, respectively.

* * * * *

UNITED STATES PATENT AND TRADEMARK OFFICE
CERTIFICATE OF CORRECTION

PATENT NO.         : 9,901,742 B2
APPLICATION NO.    : 13/103638
DATED              : February 27, 2018
INVENTOR(S)        : Michel Marc Page 1 of 3

It is certified that error appears in the above-identified patent and that said Letters Patent is hereby corrected as shown below:

In the Specification

Column 6,
Line 46, delete "*pncumoniae*" and insert -- *pneumoniae* -- therefor.

Column 6,
Line 48, delete "*Entcrobacter*" and insert -- *Enterobacter* -- therefor.

Column 6,
Line 49, delete "*acrogenes*" and insert -- *aerogenes* -- therefor.

Column 8,
Line 22, delete "submandibilar" and insert -- submandibular -- therefor.

Column 9,
Line 57, delete "e.g., a polar" and insert -- (e.g., a polar -- therefor.

Column 12,
Line 17, delete "cuprous-sulfide" and insert -- cuprous sulfide -- therefor.

Column 12,
Line 19, delete "agetate" and insert -- acetate -- therefor.

Column 13,
Line 20, delete "arabiniose" and insert -- arabinose -- therefor.

Column 15,
Line 42, delete "fins" and insert -- fms -- therefor.

Signed and Sealed this
Seventeenth Day of September, 2019

Andrei Iancu
*Director of the United States Patent and Trademark Office*

Column 18,
Line 40, delete "Biol." and insert -- J. Biol. -- therefor.

Column 19,
Line 48, delete "heating-modulator" and insert -- heating modulator -- therefor.

Column 20,
Line 10, delete "case-magnets" and insert -- case magnets -- therefor.

Column 21,
Line 8, delete "one-skilled" and insert -- one skilled -- therefor.

Column 23,
Line 33, delete "human-body" and insert -- human body -- therefor.

Column 25,
Line 4, delete "e.g., polyalky-" and insert -- (e.g., polyalky- -- therefor.

Column 25,
Line 18, delete "e.g., a relatively" and insert -- (e.g., a relatively -- therefor.

Column 30,
Line 7, delete "region-derived" and insert -- region derived -- therefor.

Column 30,
Line 30, delete "212267 watts" and insert -- 212.67 watts -- therefor.

Column 36,
Line 47, delete "294.8x" and insert -- 294.81x -- therefor.

Column 38,
Line 3, delete "29481 × 0.8342" and insert -- 294.81 × 0.8342 -- therefor.

Column 39,
Line 18, delete "0:2544" and insert -- 0.2544 -- therefor.

Column 48,
Line 44, delete "*(0.89(1–x))*" and insert -- *(1.89(1-x))* -- therefor.

Column 50,
Line 32, delete "39.32 × $t_2$" and insert -- 39.32 × $t_3$ -- therefor.

Column 53,
Line 38, delete "2.857 × $d_1$." and insert -- 2.857.6 × $d_1$ -- therefor.

CERTIFICATE OF CORRECTION (continued)
U.S. Pat. No. 9,901,742 B2

Column 60,
Line 31, delete "16.87(3.47x" and insert -- 16.387(3.47x -- therefor.

Column 74,
Line 35, delete "seconds (e 60," and insert -- seconds (e.g. 60, -- therefor.

Column 75,
Lines 8 and 9, delete "Fibcroptic" and insert -- Fiberoptic -- therefor.

Column 76,
Line 39, delete "killed (e, 50 C)" and insert -- killed (e.g., 50 C) -- therefor.

Column 76,
Line 64, delete "50," and insert -- 50°C -- therefor.